United States Patent
Ohta et al.

(10) Patent No.: US 6,939,537 B2
(45) Date of Patent: Sep. 6, 2005

(54) COMPOSITION FOR BLENDING TO HAIR TREATING AGENTS AND A HAIR TREATING AGENT

(75) Inventors: Toshio Ohta, Tokyo (JP); Michihiro Aga, Tokyo (JP); Katsuhiro Watanabe, Tokyo (JP)

(73) Assignee: San-Ei Kagaku Co., Ltd., Tokyo (JP)

( * ) Notice: Subject to any disclaimer, the term of this patent is extended or adjusted under 35 U.S.C. 154(b) by 0 days.

(21) Appl. No.: 10/094,712

(22) Filed: Mar. 12, 2002

(65) Prior Publication Data

US 2003/0086897 A1 May 8, 2003

(30) Foreign Application Priority Data

| Mar. 12, 2001 | (JP) | 2001-068709 |
| Mar. 12, 2001 | (JP) | 2001-068710 |
| Mar. 12, 2001 | (JP) | 2001-068711 |
| Mar. 12, 2001 | (JP) | 2001-068712 |
| Mar. 12, 2001 | (JP) | 2001-068713 |
| Mar. 29, 2001 | (JP) | 2001-095359 |
| May 7, 2001 | (JP) | 2001-136300 |
| Aug. 2, 2001 | (JP) | 2001-234638 |

(51) Int. Cl.$^7$ .............................................. A61K 7/09
(52) U.S. Cl. .................... 424/70.31; 424/70.19; 424/70.27; 424/70.28
(58) Field of Search ............................. 424/70.31, 70.27, 424/70.28, 70.19, 90.11, 70.12, 90.1, 70.1, 70.2, 70.6, 70.21

(56) References Cited

U.S. PATENT DOCUMENTS 5,911,979 A * 6/1999 Midha et al. ............. 424/70.12
6,419,962 B1 * 7/2002 Yokoyama et al. ......... 424/725

OTHER PUBLICATIONS

Harry's Cosmeticology by Ralph Harry, pp431–441, 1982.*
Skin Care and Cosmetic Ingrdients Dictionary, p. 90, 1994.*

* cited by examiner

*Primary Examiner*—Jyothsna Venkat
(74) *Attorney, Agent, or Firm*—Sherman & Shalloway

(57) ABSTRACT

The present invention provides compositions blended in hair treating agents which can prepare a hair conditioner, a coloring agent, a waving agent, a finishing agent, a feeling improving agent, a perfume dispersing agent, a refreshner or a thickning agent easily and by lower price, further provides a hair treating agent which is excellent in hair treating feature, such as moist feel, slippery feel, wetting feeling, smooth feel, soft feel, slightly oily feel, rustle feeling, luster, supple, no stickiness, smooth combing, setting ability by containing alcohols.

30 Claims, No Drawings

COMPOSITION FOR BLENDING TO HAIR TREATING AGENTS AND A HAIR TREATING AGENT

FIELD OF THE INVENTION

The present invention relates to compositions blended in hair treating agents, and also the hair treating agents. Especially, the present invention relates to a compositions to be blended in hair treating agents, and also the present invention relates to the hair treating agents prepared therefrom as hair conditioners such as hair treatments (including so called "non rinsing treatments") and rinses, hair colorings, waving agents, finishing agents, color fixing agents, and another hair treating agents such as permanent waving iron sliding improvers.

DESCRIPTION OF THE PRIOR ART

Recently, the requirement to hair and a hair treating agents are becoming more serious. The moist feel, slippery feel, wetting feeling, smooth feel, soft feel, slightly oily feel, rustle feeling, luster, supple, no stickiness, non congealing of hair top, setting ability, maintaining (or keeping) ability of hair styling, prevention of loss of color after hair colorings operation (prevention of loss of dye), brightness of color developing of color wax, smooth wave formation with waving agents, no waving unevenness, prevention of hair damage, well spread of cream, salt resistance of hair treating agents of hair treating agents, easy removing of wax by shampoo, natural hair line (increased volume feel or decreased volume feel), smooth combing, low irritation and no liquid dropping are strongly required.

For the purpose to satisfy the above-mentioned requirement of the consumer, hair treating agents [e.g., hair conditioners such as hair treatments (including so called "non rinsing treatments") and rinses, hair colorings, waving agents, finishing agents, color fixing agents or another hair treating agents such as permanent waving iron sliding improvers], in which various ingredients are contained, are proposed.

However, at the preparation of the conventional hair treating agents, the processes are complicated and take long time and high cost because each ingredients must be respectively weighed, added and blended, and these processes are considered as a serious problem.

Further, in the conventional hair treating agents, the specific ingredients, for example, esters, alcohols, surfactants, fats and oils, fatty acids or silicones are blended to the hair treating agents.

However, these compounds are not popular because they have specific chemical structures. Therefore, these materials have a problem that they are difficult to purchase in the market and are expensive. Further, these materials have also a problem that the hair treatments effects are not sufficient.

SUMMARY OF THE INVENTION

The object of the present invention is to provide compositions blended in hair treating agents, which can prepare hair treating agents [for example, hair conditioners such as hair treatments (including so called "non rinsing treatments") and rinses, hair colorings, waving agents, finishing agents, color fixing agents or another hair treating agents such as permanent waving iron sliding improvers], easily and by lower cost. Further, the object of the present invention is to provide the hair treating agents which are excellent at the view point of the moist feel, slippery feel, wetting feeling, smooth feel, soft feel, slightly oily feel, rustle feeling, luster, supple, no stickiness, non congealing of hair top, setting ability, maintaining ability of hair styling, prevention of loss of color after hair colorings operation (prevention of loss of dye), brightness of color developing of color wax, smooth wave formation with waving agents, no waving unevenness, prevention of hair damage, well spread of cream, salt resistance of hair treating agents, easy removing of wax by shampoo, natural hair line (increased volume feel or decreased volume feel), smooth combing, low irritation and no liquid dropping.

For the purpose to dissolve above-mentioned problems, the inventors of the present invention have conduced an ardent study and have found out that the use of compositions blended in hair treating agents, in which esters were contained, can prepare a hair treating agents having an excellent hair treating effect easily and by lower cost, and accomplished the present invention.

That is, the present invention provides compositions blended in hair treating agents, which contain esters.

Further, the present invention provides the hair treating agents in which the above-mentioned compositions are blended.

The present inventions are detailed according to the Examples.

DETAILED DESCRIPTION OF PREFERRED EMBODIMENTS

The First Embodiment

In this embodiment, esters are contained in the compositions blended in hair treating agents of the present invention.

As esters, fatty esters of polyhydric alcohols (e.g. glycols glycerols, pentaerythritols etc.), higher fatty esters, polybasic acid esters and natural fatty esters may be exemplified.

Concretely, one to three compounds selected from the group consisting of propylene glycol dicaprate, polyethylene glycol distearate, caprylic capric acid triglyceride, triglyceryl cocoate, dipentaerythritol fatty ester, isopropyl palmitate, 2hexyldecyl isostearate, isopropyl linoleate, diisostearyl malate, diisopropyl adipate, diisobutyl adipate and lanolin fatty acid octyldodecyl ester may be exemplified.

Concretely, in the compositions blended in waving agents, for example, isopropyl linoleate may be contained.

In the compositions blended in hair treating agents of the present invention, any kind of additives may be contained in accordance with the kinds and the purposes of hair treating agents.

For example, in the compositions blended in hair treating agents, one or two surfactants selected from the group consisting of nonionic surfactants, anionic surfactants, and natural surfactants may be contained as additives.

Concretely, in the compositions blended in waving agents, in the compositions blended in finishing agents and in the compositions blended in permanent waving iron sliding improvers, nonionic surfactants may be contained. In the compositions blended in hair conditioners and in the compositions blended in waving agents, anionic surfactants may be contained. In the compositions blended in waving agents, natural surfactants may be contained.

As nonionic surfactants, polyoxyethylene alkyl (or alkenyl) ethers, or polyoxyethylene derivatives prepared from natural fatty acids, and sorbitan fatty acid esters may be exemplified. Addition polymerization degrees of EO (ethylene oxide) in the above-mentioned polyoxyethylene may be 5 to 70 mole (i. e. 5 to 70 mole EO adducts).

Concretely, one to three compounds selected from the group consisting of polyoxyethylene lauryl ether, polyoxyethylene oleyl ether, polyoxyethylene lanolin, polyoxyethylene hydrogenated castor oil, cocodimethyl amine oxide, sorbitan monooleate, sorbitan sesquioleate and sorbitan trioleate may be exemplified.

As anionic surfactants, polyoxyethylene fatty acid alkylolamide sulfates may be exemplified as the concrete example. Concretely, polyoxyethylene coconut fatty acid monoethanolamide sodium sulfate may be exemplified.

As natural surfactantsoybean phospholipid may be exemplified as the concrete example.

Further, in the compositions blended in hair treating agents of the present invention, fats and oils may be contained. Concretely, in the compositions blended in hair conditioners, in the compositions blended in waving agents, in the compositions blended in finishing agents and in the compositions blended in permanent waving iron sliding improvers, fats and oils may be contained.

As the fats and oils, vegetable oils and animal oils may be exemplified as the concrete example. Concretely, one or two compound selected from the group consisting of rice germ oil, wheat germ oil, shear butter, avocado oil, safflower oil, castor oil and meadowfoam oil may be exemplified.

Further, in the compositions blended in hair treating agents of the present invention, two or four kinds selected from the groups consisting of acid, alkali, hydrocarbon and water may be contained.

Concretely, in the compositions blended in waving agents and in the compositions blended in finishing agents, two or four selected from the groups consisting of acids, alkali, hydrocarbons and water may be contained.

Organic acids and inorganic acids may be exemplified as acids. As the substantial example of acids, one to three compounds selected from the group consisting of lactic acid, sorbic acid, oleic acid and phosphoric acid may be exemplified. Inorganic alkali (e.g. sodium hydroxide) may be exemplified as alkali. As hydrocarbons, liquid petrolatum may be exemplified as the concrete example.

Further, in the compositions blended in hair treating agents of the present invention, additives such as silicones (i.e. compounds containing Si element), parabens, polyethers, antioxidants and perfumes may be contained.

Concretely, in the compositions blended in hair treating agents of the present invention, one to two compounds selected from the group consisting of dimethylsiloxane.methylstearoxysiloxane copolymer, decamethyl cyclopentasiloxane, methyl parahydroxybenzoate, polyoxypropylene butyl ether [addition polymerization degrees of PO (propylene oxide) may be 30 to 80 mole (i. e. 30 to 80 mole PO adducts)], dibutylhydroxytoluene and perfumes may be contained.

For example, in the compositions blended in hair conditioners and in the compositions blended in permanent waving iron sliding improvers, silicones may be contained. In the compositions blended in hair conditioners, for example, parabens, and polyethers may be contained. In the compositions blended in permanent waving iron sliding improvers, for example, antioxidants may be contained. In the compositions blended in waving agents and in the compositions blended in finishing agents, for example, perfumes and water may be contained.

In the formulations of the compositions blended in hair treating agents of the present invention, esters may be contained, for example, more than 0.1 wt. %. Concretely, when the respective contents of esters in the compositions blended in hair conditioners, in the compositions blended in waving agents, in the compositions blended in finishing agents and in the compositions blended in permanent waving iron sliding improvers are A, B, C and D (wt. %), it is desirable for A–D to be within following ranges; $3 \leq A \leq 100$, $0.1 \leq B \leq 5$, $0.1 \leq C \leq 5$, $0.1 \leq D \leq 10$.

When A–D is smaller than the each minimum, the moist feel may be diminished. When A–D is larger than the each maximum, oil rich feel may be too strong.

As the substantial method to prepare the compositions blended in hair treating agents of this embodiment, following method may be exemplified. That is, esters and ingredients such as additives are mixed, heated (if necessary) and stirred until completely dissolved. The heating temperature is desirably lower than the decomposition temperatures of the mixture, for example, lower than 100° C.

In another preparation method of the compositions blended in hair treating agents, for example, esters and other oiliness materials are mixed, heated and homogeneously dissolved. This homogeneously dissolved mixture is added to hot water with constant stirring and emulsified, and then cooled.

On the other hand, nonionic surfactants and water are mixed with constant stirring under heating to prepare stabilizer by homogeneously dissolving, and then cooled. The cooled stabilizer, acids and alkalis etc. are added with constant stirring to the above-mentioned cooled emulsion and mixed homogeneously to prepare the present compositions blended in hair treating agents. The heating temperature is desirably lower than the decomposition temperatures of the mixture, for example, lower than 100° C.

The hair treating agents of the present invention contain the compositions blended in hair treating agents of the present invention. As the hair treating agents, hair conditioners, waving agents, finishing agents and permanent waving iron sliding improvers are illustrated below.

The hair conditioners of the present invention contain above-mentioned compositions blended in hair conditioners. As the compositions blended in hair conditioners, one or more kinds may be used.

Further, in the hair conditioners of the present, invention, additive compositions, preservatives, perfumes and water may be contained as additives.

As additive compositions, for example, mixtures of esters, fats and oils and nonionic surfactants may be exemplified. As preservatives, parabens such as methylparaben or propylparaben may be exemplified. As perfumes, any kinds of perfumes, which are generally used to the hair conditioners, may be exemplified.

In the formulations of the hair conditioners of the present invention, the contents of the compositions blended in hair conditioners are, for example, from 0.1 to 10 wt. %.

In the preparing method of the hair conditioners of the present invention, for example, additive compositions and preservatives etc. are added to the compositions blended in hair conditioners and then homogeneously dissolved under heating. This dissolved material is added to hot water with stirring to emulsify. And then, followed by cooling, perfumes etc. are added to this emulsion to prepare the hair conditioners of the present invention. The heating temperature of water and the compositions blended in hair conditioners are desirably lower than the decomposition temperatures of the mixture, for example, desirably lower than 90° C.

As waving agents of the present invention, permanent waving agents may be exemplified. The permanent waving agents are generally composed of No. 1 agents and No. 2 agents (in the present invention, both No. 1 agents alone and No. 2 agents alone are also comprised in the hair colorings of the present invention).

No. 1 agents of the permanent waving agents of the present invention may contain reducing agents, alkaline agents and water besides the compositions blended in waving agents of the present invention. As reducing agents, thioglycolic acid and cysteine or salts (ammonium salt, MEA salt, hydrogen chloride salt etc.) of them may be exemplified. As alkaline agents, ammonia, amines (MEA, isopropanolamine etc.), ammonium salts (ammonium bicarbonate etc.) and basic amino acid may be exemplified.

In the formulations of No. 1 agents of the permanent waving agents, the contents of the compositions blended in waving agents are, for example, from 1 to 25 wt. %, desirably 1 to 10 wt. %.

As the substantial method to prepare No. 1 agents of the permanent waving agents, following method may be exemplified. That is, for example, the compositions blended in waving agents are added to water at room temperature, and further, reducing agents and alkaline agents may be added with stirring to prepare No. 1 agents of the permanent waving agents.

In No. 2 agents of the permanent waving agents of the present invention, oxidizing agents and/or water etc. may be contained besides the compositions blended in waving agents of the present invention. As oxidizing agents, salts of bromic acid or hydrogen peroxide may be exemplified.

In the formulations of No. 2 agents of the permanent waving agents, the contents of the compositions blended in waving agents are, for example, from 1 to 25 wt. %.

As the substantial method to prepare No. 2 agents of the permanent waving agents, for example, the compositions blended in waving agents are added to water, and further, oxidizing agents etc. may be added to this mixture with stirring to prepare No. 2 agents of the permanent waving agents.

The permanent waving agents of the present invention contain at least one selected from the group consisting of No. 1 agents (of permanent waving agents) of the present invention and No. 2 agents (of permanent waving agents) of the present invention. For example, the permanent waving agents of the present invention are one consisting of No. 1 agents of permanent waving agents of the present invention and No. 2 agents of permanent waving agents of the present invention, one consisting of No. 1 agents of permanent waving agents of the present invention and No. 2 agents of permanent waving agents except the above-mentioned ones and another one consisting of No. 1 agents of permanent waving agents except the above-mentioned ones and No. 2 agents of permanent waving agents of the present invention.

As "No. 1 agents of permanent waving agents except the above-mentioned ones" and "No. 2 agents of permanent waving agents except the above-mentioned ones", the No. 1 and No. 2 agents which are ordinary used in the conventional waving agents may be exemplified.

The finishing agents of the present invention contain the compositions blended in finishing agents, and generally further contain water. And, as additives, the compounds indicated in hair conditioners may be voluntarily added.

In the formulations of the finishing agents of the present invention, the contents of the compositions blended in finishing agents are, for example, from 1 to 10 wt. %.

In the preparation method of the finishing agents of the present invention, for example, the compositions blended in finishing agents, additives and water may be mixed with stirring under heating (if necessary) to emulsify.

Permanent waving iron sliding improvers of the present invention may contain additives such as perfumes and colors besides the compositions blended in permanent waving iron sliding improvers. As perfumes, any kinds of perfumes that are generally used to the permanent waving iron sliding improver may be exemplified. As colors, tar colors may be exemplified.

In the formulations of the permanent waving iron sliding improver of the present invention, the contents of the compositions blended in permanent waving iron sliding improvers may be, for example, more than 80 wt. %.

In the preparation method of the permanent waving iron sliding improver of the present invention, for example, the compositions blended in the permanent waving iron sliding improver and additives may be mixed with stirring under heating (if necessary) to homogeneous mixture.

The Second Embodiment

In this embodiment, alcohols besides esters are contained in the compositions blended in hair treating agents.

fatty Esters of polyhydric alcohols (e.g. glycerols, pentaerythritols etc.) and higher fatty esters may be exemplified as esters.

Concretely one or two compounds selected from the group consisting of mono and diglyceryl oleate and stearate (i. e. mixtures of monoglyceride and diglyceride of mixed acid of oleic acid and stearic acid), lipophilic glyceryl monostearate, lipophilic glyceryl monooleate, isopropyl myristate, octyl palmitate, cetyl palmitate and 2hexyldecyl isostearate may be exemplified.

For example, in the compositions blended in hair conditioners and in the compositions blended in finishing agents, lipophilic glyceryl monostearate may be contained. In the compositions blended in hair conditioners, for example, cetyl palmitate may be contained.

Further, in the compositions blended in hair treating agents of the present invention, alcohols are contained. As alcohols, for example, lower and higher alcohols and polyhydric alcohols etc. may be exemplified.

As the substantial example, one to three compounds selected from the group consisting of myristyl alcohol, cetanol, octyldodecanol, behenyl alcohol, ethanol and dipropylene glycol may be exemplified.

For example, in the compositions blended in hair conditioners, in the compositions blended in hair colorings, in the compositions blended in waving agents and in the compositions blended in finishing agents, cetanol may be contained. In the compositions blended in hair conditioners, for example, behenyl alcohol may be contained.

Further, in the compositions blended in hair treating agents of the present invention, any kind of additives may be contained in accordance with the kind and the purposes of hair treating agents.

For example, in the compositions blended in hair treating agents, fats and oils, anionic surfactants, organic acids, hydrocarbons, waxes, fatty acid amides of alkylaminoalkylamines, silicones and/or water may be contained as additives.

Concretely, one to five compounds selected from the group consisting of hydrogenated oils (hydrogenated palm oil fatty acid triglyceride, hydrogenated tallow acid triglyceride etc.), persic oil, lanolin, olive oil, sodium cetyl sulfate, sodium N-myristoyl N-methyl taurate, myristic acid, stearic acid, lanolin fatty acid, paraffin, beeswax, candelilla wax, stearamidoethyl diethylamine, stearamidopropyl dimethylamine, methylphenyl polysiloxane and water may be contained.

For example, in the compositions blended in hair conditioners, fats and oils may be contained. In the compositions blended in hair conditioners, in the compositions blended in hair colorings and in the compositions blended in waving agents, for example, anionic surfactants may be contained. In the compositions blended in hair conditioners, in the compositions blended in hair colorings, in the compositions blended in waving agents and in the compositions blended in finishing agents, for example, organic acids may be contained. In the compositions blended in hair colorings and in the compositions blended in waving agents, for example, hydrocarbons may be contained.

In the compositions blended in hair conditioners and in the compositions blended in finishing agents, for example, waxes may be contained. In the compositions blended in hair conditioners, for example, fatty acid amides of alkylaminoalkylamines and silicones may be contained. In the compositions blended in hair conditioners, in the compositions blended in hair colorings and in the compositions blended in waving agents, for example, water may be contained.

In the formulations of the compositions blended in hair treating agents of the present invention, when the respective contents of esters and alcohols are E and F (wt. %) respectively, it is desirable for E and F to be within following ranges; $10 \leq E \leq 35$, $10 \leq F \leq 70$, and $E+F \leq 100$.

In a case of the compositions blended in hair conditioners, E and F may be $10 \leq E \leq 35$, $50 \leq F \leq 70$, and $E+F \leq 100$.

In a case of the compositions blended in hair colorings and in the compositions blended in waving agents, E and F may be $10 \leq E \leq 20$ and $55 \leq F \leq 70$.

In a case of the compositions blended in finishing agents, E and F may be $15 \leq E \leq 25$ and $15 \leq F \leq 30$.

As the substantial method to prepare the compositions blended in hair treating agents of this embodiment, following method may be exemplified. That is, esters, alcohols and ingredients such as additives (if necessary) are mixed and stirred under heating until completely dissolved. The heating temperature is desirably lower than the decomposition temperatures of the mixture, for example, lower than 95° C. The adding order of each ingredients are not limited.

The hair treating agents of the present invention contain the compositions blended in hair treating agents of the present invention. Hair conditioners, hair colorings, waving agents and finishing agents are illustrated below as the hair treating agents.

The hair conditioners of the present invention contain above-mentioned compositions blended in hair conditioners. As the compositions blended in hair conditioners, one or more kinds may be used.

Further, in the hair conditioners of the present invention, preservatives, organic acids, additive compositions, alcohols, anionic surfactants, perfumes and water may be contained as additives.

As preservatives, parabens such as methylparaben or propylparaben may be exemplified. As organic acids, lactic acid and dl-malic acid may be exemplified. As additive compositions, mixture which contain, for example, esters, and fats and oils etc. may be exemplified. As alcohols, aromatic alcohols (e.g. phenoxyethanol etc.), higher alcohols (stearyl alcohol and behenyl alcohol etc.), glycols (polyethylene glycol etc.) may be exemplified. As anionic surfactants, salts of alkyl sulfuric acids (e.g. sodium cetyl sulfate etc.) may be exemplified. As perfumes, any kinds of perfumes, which are generally used to the hair conditioners, may be exemplified.

In the formulations of the hair conditioners of the present invention, contents of the compositions blended in hair conditioners are, for example, from 1 to 20 wt. %.

The preparing method of the hair conditioners of the present invention is not limited. For example, preservatives, organic acids and/or anionic surfactants etc., if necessary, are added to water and mixed, and then heated. On the other hand, organic acids, additive compositions and/or alcohols, if necessary, are added to the compositions blended in hair conditioners, and mixed, then heated to dissolve homogeneously.

This homogeneous dissolved material is added to the above-mentioned hot water (or hot aqueous solution) with stirring to emulsify. After cooling, perfumes or organic acids etc., if necessary, is added to the cooled mixture. The heating temperature of water and the compositions blended in hair conditioners are desirably lower than the decomposition temperatures of the ingredients, for example, more desirably lower than 95° C.

As hair colorings of the present invention, oxidizing hair coloring agents may be exemplified. The oxidizing hair coloring agents are composed of No. 1 agents and No. 2 agents (in the present invention, No. 1 agents alone and No. 2 agents alone are also comprised in the hair colorings of the present invention). No. 1 agents of the oxidizing hair coloring agents of the present invention may contain dye intermediates, alkaline agents, antioxidants, sequestering agents and/or water besides the compositions blended in hair colorings of the present invention.

As dye intermediates, for example, phenylene diamines (e.g. ortho, meta, para phenylene diamine), phenols (e.g. ortho, meta, para aminophenol, nitrophenols) and aminocresols may be exemplified. As alkaline agents, ammonia solution and MEA (monoethanolamine) may be exemplified. As antioxidants, the compounds, which are used to the ordinary oxidizing hair coloring agents, such as sodium sulfite, ammonium thioglycolate, ascorbic acid and/or cysteine may be exemplified. As the sequestering agents, e.g. EDTA may be exemplified.

In the formulations of No. 1 agents of oxidizing hair coloring agents, the contents of the compositions blended in hair colorings are, for example, from 10 to 35 wt. %, desirably from 20 to 30 wt. %.

As the substantial method to prepare No. 1 agents of oxidizing hair coloring agents, following method may be exemplified. That is, for example, dye intermediates and antioxidants are poured into hot water and prepare homogeneous aqueous solution, then the compositions blended in hair colorings, which are heated and dissolved homogeneously, are added and mixed. After cooled down, additives such as alkaline agents and/or sequestering agents may be added to the mixture by constant stirring. The heating temperature of water and the compositions blended in hair colorings are desirably lower than decomposition temperatures of the ingredients, for example, lower than 95° C.

No. 2 agents of oxidizing hair coloring agents may contain phenacetium, oxidizing agents, sequestering agents, pH adjustors, and/or water may be contained besides the compositions blended in hair colorings of the present invention. As oxidizing agents, hydrogen peroxide may be exemplified. As sequestering agents, e.g. disodium edetate may be exemplified. As pH adjustors, phosphoric acid and this salts (for example, dibasic sodium phosphate) may be exemplified.

In formulations of No. 2 agents of oxidizing hair coloring agents, the compositions blended in hair colorings may be contained, for example, from 1 to 20 wt. %.

As the substantial method to prepare No. 2 agents of oxidizing hair coloring agents, following method may be exemplified. That is, for example, the compositions blended in hair colorings of the present invention, which are heated and dissolved homogeneously, are added to hot water and dissolved homogeneously, stirred and emulsified. After cooled down, additives such as sequestering agents, pH adjustors and oxidizing agents may be added. The heating temperature of water and the compositions blended in hair colorings are desirably lower than the decomposition temperatures of the ingredients, for example, lower than 95° C.

The oxidizing hair coloring agents of the present invention contain at least one selected from the group consisting of No. 1 agents of oxidizing hair coloring agents of the present invention and No. 2 agents of oxidizing hair coloring agents of the present invention. For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones, and the hair colorings consisting of No. 1 agents of oxidizing hair coloring agents except the above-mentioned ones and No. 2 agents of oxidizing hair coloring agents of the present invention are included.

As "No. 1 agents of oxidizing hair coloring agents except the above-mentioned ones" and "No. 2 agents of oxidizing hair coloring agents except the above-mentioned ones", No. 1 agents and No. 2 agents which are generally used for the usual hair colorings may be exemplified.

As another hair colorings of the present invention, acidic hair coloring materials may be exemplified. The acidic hair coloring materials may contain tar colors, organic solvents, organic and inorganic acids, sequestering agents and water besides the present compositions blended in hair colorings. As organic solvents, benzyl alcohol and N-methl-2-pyrrolidone (NMP) may be exemplified. As organic acids, lactic acid, glycolic acid, tartaric acid and citric acid may be exemplified. As inorganic acids, phosphoric acid and hydrochloric acid may be exemplified. As sequestering agents, salts of ethylenediamine tetraacetic acid (EDTA) may be exemplified.

In formulations of the acidic hair coloring materials, the contents of the compositions blended in hair colorings are, for example, from 10 to 30 wt. %, desirably from 15 to 25 wt. %.

As the substantial method to prepare the acidic hair coloring materials, following method may be exemplified. That is, for example, the compositions blended in hair colorings of the present invention, which are heated and dissolved homogeneously, are added to hot water in which tar colors are dissolved and stirred. After cooled down, organic solvents etc. may be added with stirring. The heating temperature of water and the compositions blended in hair colorings are desirably lower than the decomposition temperatures of the ingredients, for example, lower than 95° C.

As another hair colorings, decolorizing agents may be exemplified. The decolorizing agents are generally composed of No. 1 agents and No. 2 agents (decolorizing agents, No. 1 agents alone, and No. 2 agents alone are comprised in the hair colorings of the present invention). No. 1 agents of the decolorizing agents of the present invention may contain alkaline agents, sequestering agents and water besides the compositions blended in hair colorings of the present invention. As alkaline agents, e.g. ammonia and MEA may be exemplified, and as sequestering agents, salt of EDTA may be exemplified.

In formulations of No. 1 agents of decolorizing agents, the desirable contents of the compositions blended in hair colorings are, for example, from 10 to 20 wt. %.

The preparing method of No. 1 agents of decolorizing agents are illustrated as follows. For example, the compositions blended in hair colorings, which are heated and homogeneously dissolved, are added to hot water with constant stirring and emulsified. After cooled down, additives such as alkaline agents and/or sequestering agents may be added. The heating temperature of water and the compositions blended in hair colorings are desirably lower than the decomposition temperatures of the mixture, for example, lower than 95° C.

The ingredients, formulations and preparing method of No. 2 agents of the decolorizing agents of the present invention may be the same as the case of No. 2 agents of the oxidizing hair coloring agents of the present invention.

The decolorizing agents of the present invention contain at least one selected from the group consisting of No. 1 agents of decolorizing agents of the present invention and No. 2 agents of decolorizing agents of the present invention. For example, in the decolorizing agents of the present invention, the hair colorings consisting of No. 1 agents of decolorizing agents of the present invention and No. 2 agents of decolorizing agents of the present invention, the hair colorings consisting of No. 1 agents of decolorizing agents of the present invention and No. 2 agents of decolorizing agents except the above-mentioned ones, and the hair colorings consisting of No. 1 agents of decolorizing agents except the above-mentioned ones and No. 2 agents of decolorizing agents of the present invention are included.

As "No. 1 agents of decolorizing agents except the above-mentioned ones" and "No. 2 agents of decolorizing agents except the above-mentioned ones", the No. 1 and No. 2 agents, which are ordinary used in the conventional decolorizing agents, may be exemplified.

As waving agents of the present invention, one which are composed of No. 1 agents and No. 2 agents may be exemplified (in the present invention, both No. 1 agents alone and No. 2 agents alone are also comprised in the waving agents of the present invention).

No. 1 agents of the waving agents of the present invention may contain reducing agents, alkaline agents and water besides the compositions blended in waving agents of the present invention. As reducing agents, thioglycolic acid and cysteine and/or salts (ammonium salt, MEA salt, hydrochloric acid salts etc.) of them may be exemplified. As alkaline agents, ammonia, amines (MEA, isopropanolamine etc.), ammonium salts (ammonium bicarbonate etc.) and basic amino acid may be exemplified.

In formulations of No. 1 agents of the present waving agents, the contents of the compositions blended in waving agents are, for example, from 10 to 25 wt. %, desirably 5 to 20 wt. %.

As the substantial method to prepare No. 1 agents of the present waving agents, following method may be exemplified. That is, for example, the compositions blended in waving agents, which are heated and dissolved homogeneously, are added to hot water, stirred and emulsified. After cooled down, reducing agents and alkaline agents may be added with stirring. The heating temperature of water and the compositions blended in waving agents are desirably lower than the decomposition temperatures of the ingredients, for example, lower than 90° C.

In No. 2 agents of the waving agents of the present invention, oxidizing agents and/or water etc. may be contained besides the compositions blended in waving agents of the present invention. As oxidizing agents, salts of bromic acid and/or hydrogen peroxide may be exemplified.

In the formulations of No. 2 agents of the waving agents, the contents of the compositions blended in waving agents are, for example, from 5 to 25 wt. %.

As the substantial method to prepare No. 2 agents of the present waving agents, following method may be exemplified. That is, for example, the compositions blended in waving agents, which are heated and dissolved homogeneously, are added to hot water, stirred and emulsified. After cooled down, oxidizing agents etc. may be added with stirring. The heating temperature of water and the compositions blended in waving agents are desirably lower than the decomposition temperatures of the ingredients, for example, lower than 90° C.

As another No. 2 agents of the waving agents of the present invention, No. 2 agents of the cream type waving agents may be exemplified. In No. 2 agents of the cream type waving agents of the present invention, phenacetium, sequestering agents, oxidizing agents, pH adjustors and/or water may be contained. As oxidizing agents, salts of bromic acid and/or hydrogen peroxide may be exemplified. As sequestering agents, e.g. disodium edetate may be exemplified.

In formulations of No. 2 agents of the present cream type waving agents, the contents of the compositions blended in waving agents are, for example, from 10 to 25 wt. %.

In the preparation method of No. 2 agents of the cream type waving agents of the present invention, for example, sequestering agents are added to water and heated to prepare aqueous solution. On the other hand, the compositions blended in the waving agents of the present invention and phenacetium are mixed under heating to prepare homogeneous dissolved material. The homogeneous dissolved material are added to the above-mentioned hot aqueous solution with constant stirring to emulsify. After the emulsion is cooled, oxidizing agents and pH adjustors are added to the cooled emulsion. The heating temperature of water and the compositions blended in waving agents are desirably lower than the decomposition temperatures of the ingredients, for example, lower than 90° C.

The waving agents of the present invention contain at least one selected from the group consisting of No. 1 agents of waving agents of the present invention and No. 2 agents of waving agents of the present invention. For example, the waving agents of the present invention is one consisting of No. 1 agents of waving agents of the present invention and No. 2 agents of waving agents of the present invention, one consisting of No. 1 agents of waving agents of the present invention and No. 2 agents of waving agents except the above-mentioned ones, and another one consisting of No. 1 agents of waving agents except the above-mentioned ones and No. 2 agents of waving agents of the present invention.

As "No. 1 agents of waving agents except the above-mentioned ones" and "No. 2 agents of waving agents except the above-mentioned ones", the No. 1 and No. 2 agents, which are ordinary used in the conventional waving agents, may be exemplified respectively.

The finishing agents of the present invention contain the compositions blended in finishing agents, and generally further contain water. Further, as additives, hydrocarbons, silicones, alcohols, organic alkaline agents, coloring materials, preservatives, esters, gum substances, organic acids, fats and oils, pigments and anionic surfactants may be contained.

As hydrocarbons, squalane may be exemplified. As silicones, methyl polysiloxane whose viscosity, for example, has 1–200 cs may be exemplified. As alcohols, behenyl alcohol, 1,3-butylene glycol, 3-methyl-1,3-butandiol and glycerin may be exemplified. As organic alkaline agents, triethanolamine (TEA) and 2-amino-2-methyl-1-propanol may be exemplified.

As coloring materials, kaolin may be exemplified. As preservatives, parabens may be exemplified. As esters, fatty esters such as isocetyl isononanoate and isopropyl myristate may be exemplified. As gum substances, xanthan gum may be exemplified. As organic acids, lactic acid may be exemplified. As fats and oils, castor oil may be exemplified. As colors, pearl color may be exemplified. As anionic surfactants, sodium tetradecen sulfonate may be exemplified.

In formulations of the finishing agents of the present invention, the contents of the compositions blended in finishing agents are, for example, from 1 to 35 wt. %.

As the substantial method to prepare the finishing agents of the present invention, following method may be exemplified. That is, for example, organic alkaline agents and gum substances are dissolved in water and heated. On the other hand, esters and preservatives are added to the compositions blended in finishing agents and dissolved homogeneously with constant stirring under heating. And, this homogeneous dissolved material is added to the above-mentioned hot aqueous solution with constant stirring to emulsify. After this emulsion is cooled down, alcohols and organic acids are added to this emulsion. The heating temperature of water and the compositions blended in finishing agents are desirably lower than the decomposition temperatures of the ingredients, for example, lower than 90° C.

As another substantial method to prepare the finishing agents of the present invention, following method may be exemplified. That is, for example, the compositions blended in finishing agents and additives, if necessary, such as hydrocarbons, alcohols, fats and oils, silicones, preservatives and pigments are mixed and dissolved or dispersed homogeneously under heating. On the other hand, initial purified water and additives, if necessary, such as coloring materials, organic alkaline agents and anionic surfactants are mixed homogeneously under heating.

Then, this homogeneous aqueous mixture is added to the above-mentioned homogeneous oiliness mixture with constant stirring to emulsify. After this emulsion is cooled down, alcohols etc. are added to this emulsion. The heating temperature of aqueous mixture and the oiliness mixture are desirably lower than the decomposition temperatures of the ingredients, for example, lower than 90° C.

The Third Embodiment

In this embodiment, alcohols and nonionic surfactants besides esters are contained in the compositions blended in hair treating agents.

As esters, fatty esters of polyhydric alcohols (e.g. glycerin, pentaerythritols etc.), higher fatty esters and polybasic acid esters may be exemplified.

Concretely one to three compounds selected from the group consisting of fatty acid glyceryl ester (e.g. mixture of glyceryl mono, di and tristearate, mixture of mono and diglyceryl of mixed acid of stearic acid and oleic acid), lipophilic glyceryl monostearate, lipophilic glyceryl monooleate, pentaerithritol tetra-2-ethylhexanoate, isopropyl myristate, myristyl myristate, isopropyl palmitate, butyl stearate, di (2-ethylhexyl) succinate and diisobutyl adipate may be exemplified.

For example, in the compositions blended in hair conditioners, in the compositions blended in hair colorings and in the compositions blended in waving agents, isopropyl myristate may be contained.

Further, in the compositions blended in hair treating agents of the present invention, alcohols are contained. As alcohols, for example, lower and higher alcohols, aromatic alcohols and polyhydric alcohols etc. may be exemplified.

Concretely, one to three compounds selected from the group consisting of myristyl alcohol, hexyldecanol, cetanol, oleyl alcohol, behenyl alcohol, lanolin alcohol, ethanol, benzyl alcohol, 1,3-butylene glycol and dipropylene glycol may be exemplified.

For example, in the compositions blended in hair colorings and in the compositions blended in waving agents, cetanol may be contained.

Further, in the compositions blended in hair treating agents of the present invention, nonionic surfactants are contained. As nonionic surfactants, for example, polyoxyethylene alkyl ether, polyoxyethylene derivatives prepared from natural fatty acids, fatty acid alkylolamides and/or higher aliphatic tertiary amines may be exemplified. As the above-mentioned polyoxyethylene ether, e.g. 3 to 65 mole EO may be exemplified.

Concretely, one to three compounds selected from the group consisting of polyoxyethylene lauryl ether, polyoxyethylene cetyl ether, polyoxyethylene hydrogenated castor oil, lauric acid diethanolamide, coconut fatty acid diethanolamide and dimethyl stearylamine may be exemplified.

For example, in the compositions blended in hair conditioners, in the compositions blended in hair colorings, in the compositions blended in waving agents and in the compositions blended in finishing agents, polyoxyethylene cetyl ether may be contained.

Further, in the compositions blended in hair treating agents of the present invention, any kind of additives may be contained in accordance with the kind and the purposes of hair treating agents.

For example, in the compositions blended in hair treating agents of the present invention, additives such as fats and oils, anionic surfactants, hydrocarbons, waxes, amphoteric surfactants, polyglycerin derivatives, organic acids, silicones, fatty aminoalkylamides and water may be contained.

Concretely, one to five compounds selected from the group consisting of hydrogenated oil (e.g. hydrogenated palm oil fatty acid triglyceride, hydrogenated tallow acid triglyceride etc.), mink oil, olive oil, castor oil, shea butter, sodium cetyl sulfate, sodium palmitoyl N-methyl taurate, sodium tetradecen sulfonate, sodium polyoxyethylene oleyl ether phosphate, triethanolamine N-cocoyl-L-glutamate, α-olefin oligomer, squalane, microcrystalline wax, liquid petrolatum, ceresin, candelilla wax, beeswax, hydrochloric acid salt of N-[3-alkyl(12, 14)oxy-2-hydroxypropyl]-L-arginine ("alkyl (12, 14)" designates C12–C14 alkyl), polyglyceryl diisostearate, lactic acid, methyl polysiloxane, stearamidopropyl dimethylamine and purified water may be contained.

For example, in the compositions blended in hair conditioners, in the compositions blended in hair colorings and in the compositions blended in waving agents, fats and oils and/or anionic surfactants may be contained. For example, in the compositions blended in hair conditioners and in the compositions blended in finishing agents, hydrocarbons may be contained.

For example, in the compositions blended in hair conditioners, in the compositions blended in hair colorings and in the compositions blended in finishing agents, waxes may be contained. For example, in the compositions blended in hair conditioners, amphoteric surfactants, polyglycerin derivatives, lactic acid, fatty aminoalkylamides may be contained. For example, in the compositions for blending hair colorings and in the compositions blended in waving agents, silicones may be contained. For example, in the compositions for blending hair colorings, water may be contained.

In the formulations of the compositions blended in hair treating agents of the present invention, when the respective contents of esters, alcohols and nonionic surfactants are g, H and I (wt. %) respectively, it is desirable for G, H and I to be within following ranges; $3 \leq G \leq 35$, $5 \leq H \leq 70$, $1 \leq I \leq 40$, and $G+H+I \leq 100$.

In a case of the compositions blended in hair conditioners, G, H and I may be $3 \leq G \leq 35$, $5 \leq H \leq 45$, $5I \leq 40$, and $G+H+I \leq 100$.

In a case of the compositions blended in hair colorings, G, H and I may be $5 \leq G \leq 15$, $50 \leq H \leq 70$, $3 \leq I \leq 25$, and $G+H+I \leq 100$.

In a case of the compositions blended in waving agents, G, H and I may be $10 \leq G \leq 20$, $50 \leq H \leq 65$, $1 \leq I \leq 25$, and $G+H+I \leq 100$.

In a case of the compositions blended in finishing agents, G, H and I may be $20 \leq G \leq 30$, $5 \leq H \leq 15$, $30 \leq I \leq 45$, and $G+H+I \leq 100$.

As the substantial method to prepare the compositions blended in hair treating agents of this embodiment, following method may be exemplified. That is, esters, alcohols, nonionic surfactants and ingredients such as additives (if necessary) are mixed and stirred under heating until completely dissolved. The heating temperature is desirably lower than the decomposition temperatures of the mixture, for example, lower than 95° C. The adding order of each ingredients are not limited.

The hair treating agents of the present invention contain the compositions blended in hair treating agents of the present invention. Hair conditioners, hair colorings, waving agents and finishing agents are illustrated below as the hair treating agents.

The hair conditioners of the present invention contain above-mentioned compositions blended in hair conditioners. As the compositions blended in hair conditioners, one or more kinds may be used.

Further, to the hair conditioners of the present invention, water, additive compositions, preservatives, perfumes, colors, anionic surfactants, alcohols, organic acids, amino acids, higher fatty acids, waxes, silicones, esters, alkaline agents, polymers and fats and oils may be contained.

As additive compositions, for example, mixture of esters, fats and oils, and silicones may be exemplified. As preservatives, parabens such as methylparaben or propylparaben may be exemplified. As perfumes, any kinds of perfumes, which are generally used to the hair conditioners, may be exemplified. As colors, tar colors may be exemplified. As anionic surfactants, amino acid derivatives may be exemplified.

As alcohols, aromatic alcols (e.g. phenoxyethanol etc.), higher alcohols (stearyl alcoho etc.), glycols (polyethylene glycol etc.) may be exemplified. As organic acids, glycolic acid, lactic acid and citric acid may be exemplified. As amino acids, glutamic acid may be exemplified. As higher fatty acids, stearic acid and hydroxystearic acid may be exemplified. As waxes, candelilla wax may be exemplified.

As silicones, methyl polysiloxane may be exemplified. Fatty esters, polybasic acid esters and oligoesters may be exemplified as esters. Concretely, as esters, N-acyl glutamic acid esters, isopropyl palmitate, dioctyl succinate and polypropylene glycol oligosuccinate may be exemplified.

As alkaline agents, organic alkaline agents [e.g. triethanolamine (TEA) etc.] and inorganic alkaline agents (e.g. sodium hydroxide etc.) may be exemplified. As polymers, polyethylene glycol [average molecular weight (A. M. W) 1 million to 4 million] and polyvinylpyrrolidone (PVP)-vinyl acetate (VA) copolymer (A. M. W 1 million to 3 million)

may be exemplified. As fats and oils, hydrogenated oil may be exemplified.

In the formulations of the hair conditioners of the present invention, the compositions blended in hair conditioners are, for example, from 3 to 65 wt. %.

The preparing method of the hair conditioners of the present invention is not limited. For example, organic acids and alkaline agents etc., if necessary, are added to water and mixed, and then heated. On the other hand, additive compositions, preservatives, anionic surfactants, alcohols, organic acids, waxes, silicones and esters, if necessary, are added to the compositions blended in hair conditioners, and mixed, then heated to dissolve homogeneously.

This homogeneous dissolved material is added to the above-mentioned hot water (or hot aqueous solution) with stirring to emulsify. After cooling, perfumes and/or colors etc., if necessary, are added to the cooled mixture. The heating temperature of water and the compositions blended in hair conditioners is desirably lower than the decomposition temperatures of the ingredients, for example, lower than 95° C.

As another preparing method of the hair conditioners of the present invention is, for example, silicones, fats and oils, and esters are added to the compositions blended in hair conditioners, and mixed with stirring under heating, if necessary, to dissolve homogeneously. Then water is added to the solution.

As hair colorings of the present invention, oxidizing hair coloring agents may be exemplified. The oxidizing hair coloring agents are composed of No. 1 agents and No. 2 agents (in the present invention, No. 1 agents alone and No. 2 agents alone are also comprised in the hair colorings of the present invention). No. 1 agents of the oxidizing hair coloring agents of the present invention may contain dye intermediates, antioxidants, alkaline agents, sequestering agents, alcohols, solvents and/or water besides the compositions blended in hair colorings of the present invention.

As dye intermediates, for example, phenylene diamines (e.g. ortho, meta, para phenylene diamine), phenols (e.g. ortho, meta, para aminophenol, nitrophenols) and aminocresols may be exemplified. The compounds, which are used to the ordinary oxidizing hair coloring agents, such as sodium sulfite, ammonium thioglycolate, ascorbic acid and/or cysteine may be exemplified as antioxidants.

As alkaline agents, monoethanolamine (MEA) and ammonia may be exemplified. As the sequestering agents, e.g. salt of EDTA and hydroxyethane diphosphonic acid may be exemplified. As alcohols, cetanol may be exemplified. As solvents, N-methl-2-pyrrolidone (NMP) may be exemplified.

In the formulations of No. 1 agents of oxidizing hair coloring agents, the contents of the compositions blended in hair colorings are, for example, from 10 to 35 wt. %, desirably from 20 to 30 wt. %.

As the substantial method to prepare No. 1 agents of oxidizing hair coloring agents, following method may be exemplified. That is, for example, dye intermediates, antioxidants and the sequestering agents are poured into hot water and prepare homogeneous aqueous solution, then the compositions blended in hair colorings, which are heated and dissolved homogeneously, are added and mixed. After cooled down, additives such as alkaline agents may be added to the mixture by constant stirring. The heating temperature of water and the compositions blended in hair colorings is lower than decomposition temperatures of the ingredients, for example, desirably lower than 90° C.

No. 2 agents of oxidizing hair coloring agents of present invention may contain equestering agents, pH adjustors, oxidizing agents and/or water may be contained besides the compositions blended in hair colorings of the present invention. As sequestering agents, e.g. hydroxyethane diphosphonic acid may be exemplified. As pH adjustors, the salt of phosphoric acid (for example, dibasic sodium phosphate) may be exemplified. As oxidizing agents, hydrogen peroxide may be exemplified.

In formulations of No. 2 agents of oxidizing hair coloring agents, the compositions blended in hair colorings may be contained, for example, from 1 to 15 wt. %, desirably from 2 to 10 wt. %.

As the substantial method to prepare No. 2 agents of oxidizing hair coloring agents, following method may be exemplified. That is, for example, the compositions blended in hair colorings of the present invention, which are heated and dissolved homogeneously, are added to hot water and stirred to emulsify. After cooled down with constant stirring, additives such as sequestering agents, pH adjustors and oxidizing agents may be added. The heating temperature of water and the compositions blended in hair colorings is desirably lower than the decomposition temperatures of the ingredients, for example, lower than 90° C.

The oxidizing hair coloring agents of the present invention contain at least one selected from the group consisting of No. 1 agents of oxidizing hair coloring agents of the present invention and No. 2 agents of oxidizing hair coloring agents of the present invention. For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones, and the hair colorings consisting of No. 1 agents of oxidizing hair coloring agents except the above-mentioned ones and No. 2 agents of oxidizing hair coloring agents of the present invention are included.

As "No. 1 agents of oxidizing hair coloring agents except the above-mentioned ones" and "No. 2 agents of oxidizing hair coloring agents except the above-mentioned ones", No. 1 agents and No. 2 agents which are generally used for the usual hair colorings may be exemplified.

As another hair colorings of the present invention, acidic hair coloring materials may be exemplified. The acidic hair coloring materials may contain waxes, preservatives, gum substances, colors, organic solvents, ethers, organic and inorganic acids and the salts (e.g. ammonium salt) of them, perfumes and water may be contained besides the compositions blended in hair colorings.

As waxes, preservatives, colors, organic acids and perfumes, those compounds that indicated in the compositions blended in hair conditioners may be exemplified respectively. As gum substances, xanthan gum may be exemplified. As organic solvents, benzyl alcohol may be exemplified. As ethers, diethylene glycol monoethyl ethers may be exemplified. As inorganic acids, phosphoric acid may be exemplified.

In formulations of the acidic hair coloring materials, the contents of the compositions blended in hair colorings are, for example, from 10 to 30 wt. %, desirably from 10 to 20 wt. %.

As the substantial method to prepare the acidic hair coloring materials, following method may be exemplified. That is, for example, the compositions blended in hair colorings, waxes, and preservatives are mixed, and dissolved homogeneously under heating. Then, this homogeneous solution is added to hot water which contain gum substances and tar colors, and then emulsified with stirring. After cooled down, organic solvents, organic and/or inorganic acids and the salts of them etc. may be added. The heating temperature of water and the compositions blended in hair colorings are desirably lower than the decomposition temperatures of the ingredients, for example, lower than 90° C.

As another hair colorings, decolorizing agents may be exemplified. The decolorizing agents are generally composed of No. 1 agents and No. 2 agents. As No. 1 agents of the decolorizing agents of the present invention, for example, No. 1 agents of oxidizing hair coloring agents in which dye intermediates are not contained may be exemplified. The contents of the the compositions blended in hair colorings in No. 1 agents of the decolorizing agents and the preparation method of No. 1 agents of the decolorizing agents may be the same as the case of No. 1 agents of oxidizing hair coloring agents. As No. 2 agents of the decolorizing agents, No. 2 agents of oxidizing hair coloring agents may be used.

As waving agents of the present invention, one which are composed of No. 1 agents and No. 2 agents may be exemplified (in the present invention, both No. 1 agents alone and No. 2 agents alone are also comprised in the waving agents of the present invention).

No. 1 agents of the waving agents of the present invention may contain reducing agents, alkaline agents and water besides the compositions blended in waving agents of the present invention. As reducing agents, thioglycolic acid, cysteine and/or salts (ammonium salt, MEA salt, hydrochloric acid salts etc.) of them may be exemplified. As alkaline agents, ammonia, amines (MEA, isopropanolamine, etc.), ammonium salts (ammonium bicarbonate etc.) and basic amino acid may be exemplified.

In formulations of No. 1 agents of the present waving agents, the contents of the compositions blended in waving agents are, for example, from 5 to 25 wt. %, desirably 5 to 20 wt. %.

As the substantial method to prepare No. 1 agents of the present waving agents, following method may be exemplified. That is, for example, the compositions blended in waving agents, which are heated and dissolved homogeneously, are added to hot water, stirred and emulsified. After cooled down, reducing agents and alkaline agents may be added with stirring. The heating temperature of water and the compositions blended in waving agents are desirably lower than the decomposition temperatures of the ingredients, for example, lower than 90° C.

In No. 2 agents of the waving agents of the present invention, oxidizing agents, surfactants, organic acids, inorganic acids, sequestering agents and/or water may be contained. As oxidizing agents, salts of bromic acid and/or hydrogen peroxide may be exemplified. As surfactants, lauryl trimethyl ammonium halide (lauryl trimethyl ammonium chloride, lauryl trimethyl ammonium bromide etc.) may be exemplified. As organic acids, citric acid and/or tartaric acid may be exemplified. As inorganic acids, phosphoric acid and/or dibasic sodium phosphate may be exemplified. Further, as sequestering agents, e.g. hydroxyethane diphosphonic acid may be exemplified.

In formulations of No. 2 agents of the waving agents, the contents of the compositions blended in waving agents are, for example, from 5 to 25 wt. %.

As the substantial method to prepare No. 2 agents of the present waving agents, following method may be exemplified. That is, for example, the compositions blended in waving agents, which are heated and dissolved homogeneously, are added to hot water, stirred and emulsified. After cooled down, oxidizing agents and surfactants may be added with stirring. The heating temperature of water and the compositions blended in waving agents are lower than the decomposition temperatures of the ingredients, for example, desirably lower than 90° C.

The waving agents of the present invention contain at least one selected from the group consisting of No. 1 agents of waving agents of the present invention and No. 2 agents of waving agents of the present invention. For example, the waving agents of the present invention is one consisting of No. 1 agents of waving agents of the present invention and No. 2 agents of waving agents of the present invention, one consisting of No. 1 agents of waving agents of the present invention and No. 2 agents of waving agents except the above-mentioned ones, and another one consisting of No. 1 agents of waving agents except the above-mentioned ones and No. 2 agents of waving agents of the present invention.

As "No. 1 agents of waving agents except the above-mentioned ones" and "No. 2 agents of waving agents except the above-mentioned ones", the No. 1 and No. 2 agents, which are ordinary used in the conventional waving agents, may be exemplified respectively. Concretely, as No. 2 agents of waving agents except the above-mentioned ones, the mixture prepared by dissolving oxidizing agents and surfactants homogeneously in water may be exemplified.

The finishing agents of the present invention contain the compositions blended in finishing agents, and generally further contain water. Further, as additives, alcohols, silicones, esters, waxes, fatty acids, preservatives, polymers, alkaline agents, additive compositions and the compounds indicated as additives in hair conditioners As alcohols, stearyl alcohol may be exemplified. As silicones, dimethyl polysiloxane(50–150 cs). As esters, pentaerithritol tetra-2-ethylhexanoate may be exemplified. As waxes, candelilla wax may be exemplified. As fatty acids, stearic acid may be exemplified.

As preservatives, parabens may be exemplified. As polymers, polyethylene glycol (A. M. W 1 million to 4 million etc.) may be exemplified. As alkaline agents, triethanolamine (TEA) etc. may be exemplified. As additives compositions, mixtures with solvents, glycols and amphoteric surfactants may be exemplified.

In formulations of the finishing agents of the present invention, the contents of the compositions blended in finishing agents are, for example, from 1 to 35 wt. %.

As the substantial method to prepare the finishing agents of the present invention, following method may be exemplified. That is, for example, polymers and alkaline agents are dissolved in water and heated. On the other hand, alcohols, silicones, esters, waxes, fatty acids and preservatives are added to the compositions blended in finishing agents and dissolved homogeneously with constant stirring under heating.

And, this homogeneous dissolved material is added to the above-mentioned hot aqueous solution with constant stirring to emulsify. And then, additives compositions are added to this emulsion. After this emulsion is cooled down, perfumes etc., if necessary, are added to this emulsion. The heating temperature of water and the compositions blended in finishing agents are lower than the decomposition temperatures of the ingredients, for example, desirably lower than 95° C.

The Fourth Embodiment

In this embodiment, alcohols, nonionic surfactants and fatty acids besides esters are contained in the compositions blended in hair treating agents.

As esters, fatty esters of polyhydric alcohols (e.g. glycerin etc.), higher fatty esters and polybasic acid esters may be exemplified. Concretely, one or two compounds selected from the group consisting of mono and diglyceryl oleate and stearate (i. e. mono and diglyceride prepared from mixed acid of oleic acid and stearic acid), lipophilic glyceryl monostearate, glyceryl monooleate, isononyl isononanoate, isopropyl myristate, isopropyl palmitate, stearyl stearate and diisobutyl adipate may be exemplified.

For example, in the compositions blended in hair conditioners, in the compositions blended in hair colorings, in the compositions blended in waving agents, and in the compositions blended in finishing agents, lipophilic glyceryl monostearate and/or isopropyl myristate may be contained.

Further, in the compositions blended in hair treating agents of the present invention, alcohols are contained. As alcohols, for example, higher alcohols, polyhydric alcohols and natural alcohos etc. may be exemplified. Concretely, one to three compounds selected from the group consisting of myristyl alcohol, hexyldecanol, cetanol, behenyl alcohol, arachyl alcohol, 1,3-butylene glycol, dipropylene glycol and cetostearyl alcohol may be exemplified.

For example, in the compositions blended in hair conditioners, in the compositions blended in hair colorings, and in the compositions blended in finishing agents, cetanol may be contained. For example, in the compositions blended in hair conditioners and in the compositions blended in finishing agents, behenyl alcohol may be contained. For example, in the compositions blended in hair conditioners, in the compositions blended in hair colorings, in the compositions blended in waving agents, and in the compositions blended in finishing agents, cetostearyl alcohol may be contained.

Further, in the compositions blended in hair treating agents of the present invention, nonionic surfactants are contained. As nonionic surfactants, for example, polyoxyethylene alkyl ether, polyoxyethylene derivatives prepared from natural fatty acid, alkylolamides, sorbitan fatty ester or polyoxyethylene fatty acid amide may be exemplified. As the above-mentioned polyoxyethylene ether, e.g. 3 to 45 mole of EO (ethylene oxide) adducts may be exemplified. Concretely, one or two compounds selected from the group consisting of polyoxyethylene lauryl ether, polyoxyethylene cetyl ether, polyoxyethylene hydrogenated castor oil, coconut fatty acid monoethanolamide, sorbitane monostearete, polyoxyethylene stearic acid amide and dimethyl stearylamine may be exemplified.

For example, in the compositions blended in hair colorings, polyoxyethylene lauryl ether may be contained. For example, in the compositions blended in hair conditioners, in the compositions blended in hair colorings, in the compositions blended in waving agents, and in the compositions blended in finishing agents, polyoxyethylene cetyl ether may be contained. For example, in the compositions blended in hair colorings, coconut fatty acid monoethanolamide may be contained. For example, in the compositions blended in hair conditioners, in the compositions blended in hair colorings, and in the compositions blended in waving agents, polyoxyethylene stearic acid amide may be contained.

Further, in the compositions blended in hair treating agents of the present invention, fatty acids are contained. As fatty acids, for example, higher fatty acids, natural fatty acids etc. may be exemplified. Concretely, one or two compounds selected from the group consisting of lauric acid, myristic acid, stearic acid, oleic acid and lanolin fatty acid may be exemplified.

For example, in the compositions blended in hair colorings, and in the compositions blended in finishing agents, stearic acid may be contained.

Further, in the compositions blended in hair treating agents of the present invention, any kind of additives may be contained in accordance with the kind and the purposes of hair treating agents. For example, in the compositions blended in hair treating agents of the present invention, additives such as anionic surfactants, fats and oils, hydrocarbons, waxes, silicones (i. e. compounds which containi element), oligoesters and water may be contained.

Concretely, one to seven kinds of compounds selected from the groups consisting of sodium tetradecen sulfonate, sodium palmitoyl N-methyl taurate, sulfonated castor oil, triethanolamine N-cocoyl-L-glutamate, mink wax, shea butter, paraffin, liquid petrolatum, rice bran wax, candelilla wax, methyl polysiloxane, polypropylene glycol oligosuccinate and water may be contained.

For example, in the compositions blended in hair conditioners, in the compositions blended in hair colorings, and in the compositions blended in waving agents, anionic surfactants and/or fats and oils may be contained. For example, in the compositions blended in hair conditioners, in the compositions blended in hair colorings, in the compositions blended in waving agents, and in the compositions blended in finishing agents, hydrocarbons may be contained.

For example, in the compositions blended in hair conditioners, in the compositions blended in hair colorings, in the compositions blended in waving agents, and in the compositions blended in finishing agents, waxes may be contained. For example, in the compositions blended in hair colorings, silicones may be contained. For example, in the compositions blended in hair conditioners, oligoesters may be contained. For example, in the compositions blended in hair conditioners, in the compositions blended in hair colorings and in the compositions blended in waving agents, water may be contained.

In the formulations of the compositions blended in hair treating agents of the present invention, when the respective contents of esters, alcohols, nonionic surfactants, and fatty acids are J, K, L and M (wt. %) respectively, it is desirable for J–M to be within following ranges; $3 \leq J \leq 45$, $5 \leq K \leq 80$, $3 \leq L \leq 25$, $1 \leq M \leq 15$ and $J+K+L+M \leq 100$.

For example, in a case of the compositions blended in hair conditioners and the compositions blended in waving agents, J, K, L and M may be $5 \leq J \leq 20$, $50 \leq K \leq 70$, $1 \leq L \leq 25$, $1 \leq M \leq 10$ and $J+K+L+M \leq 100$.

For example, in a case of the compositions blended in hair colorings, J, K, L and M may be $5 \leq J \leq 15$, $45 \leq K \leq 55$, $10 \leq L \leq 20$, $1 \leq M \leq 15$ and $J+K+L+M \leq 100$.

For example, in a case of the compositions blended in finishing agents, J, K, L and M may be $5 \leq J \leq 45$, $5 \leq K \leq 80$, $5 \leq L \leq 25$, $1 \leq M \leq 15$ and $J+K+L+M \leq 100$.

As the substantial method to prepare the compositions of this embodiment blended in hair treating agents, following method may be exemplified. That is, esters, alcohols, nonionic surfactants, fatty acids and ingredients such as additives (if necessary) are mixed and stirred under heating until completely dissolved. The heating temperature is desirably lower than the decomposition temperatures of the mixture, for example, lower than 100° C., desirably lower than 95° C. The adding order of each ingredients is not limited.

The hair treating agents of the present invention contain the compositions blended in hair treating agents of the present invention. As the hair treating agents, hair conditioners, hair colorings, waving agents and finishing agents are illustrated below.

The hair conditioners of the present invention contain above-mentioned compositions blended in hair conditioners. As the compositions blended in hair conditioners, one or more kinds may be used.

Further, to the hair conditioners of the present invention, water, additive compositions, preservatives, perfumes, colors, organic acids, gum substances, antioxidants, sequestering agents, and pH adjustors may be contained.

As additive compositions, for example, mixture of esters, fats and oils, polyethers, silicones, inorganic and organic acids and solvents may be exemplified. As preservatives, parabens such as methylparaben or propylparaben may be exemplified. As colors and perfumes, any kinds of colors and perfumes that are generally used to the hair conditioners may be exemplified.

As organic acids, lactic acid and citric acid may be exemplified. As gum substances, xanthan gum may be exemplified. As antioxidants, dibutylhydroxytoluene, may be exemplified. As sequestering agents, e.g. disodium edetate may be exemplified. As pH adjustors, levulinic acid, citric acid, phosphoric acid and salts of them may be exemplified.

In the formulations of the hair conditioners of the present invention, the contents of the compositions blended in hair conditioners are, for example, from 5 to 30 wt. %.

The preparing method of the hair conditioners of the present invention is not limited. For example, the present compositions blended in the hair conditioners, in which additives, if necessary, such as preservatives, additive compositions and organic acids are dissolved homogeneously under heating, are added with stirring to hot water, in which additives, if necessary, such as organic acids and gum substances are contained, and emulsified. After cooled down, additives such as perfumes, colors and preservatives may be added. The heating temperature of water and the compositions blended in the hair conditioners are desirably lower than the decomposition temperatures of the ingredients, for example, lower than 90° C.

As hair colorings of the present invention, oxidizing hair coloring agents may be exemplified. The oxidizing hair coloring agents are composed of No. 1 agents and No. 2 agents (in the present invention, No. 1 agents alone and No. 2 agents alone are also comprised in the hair colorings of the present invention). No. 1 agents of the oxidizing hair coloring agents of the present invention may containolvents, dye intermediates, antioxidants, alkaline agents, sequestering agents, and/or water besides the compositions blended in hair colorings of the present invention.

As solvents, cetanol and N-methl-2-pyrrolidone (NMP) may be exemplified. As dye intermediates, for example, phenylene diamines (e.g. ortho, meta, para phenylene diamine), phenols (e.g. ortho, meta, para aminophenol, nitrophenols) and aminocresols may be exemplified.

As antioxidants, the compounds used to the ordinary oxidizing hair coloring agents such as sodium sulfite, ammonium thioglycolate, ascorbic acid and/or cysteine may be exemplified. As alkaline agents, monoethanolamine (MEA) and ammonia may be exemplified. As sequestering agents, e.g. salt of EDTA and hydroxyethane diphosphonic acid may be exemplified.

In the formulations of No. 1 agents of oxidizing hair coloring agents, the contents of the compositions blended in hair colorings are, for example, from 10 to 35 wt. %, desirably from 20 to 30 wt. %.

As the substantial method to prepare No. 1 agents of oxidizing hair coloring agents, following method may be exemplified. That is, for example, dye intermediates and antioxidants are poured into hot water and prepare homogeneous aqueous solution, then the compositions blended in hair colorings, which are heated and dissolved homogeneously, are added and mixed. After cooled down, additives such as alkaline agents and sequestering agents may be added to the mixture by constant stirring. The heating temperature of water and the compositions blended in hair colorings is lower than decomposition temperatures of the ingredients, for example, desirably lower than 95° C.

No. 2 agents of oxidizing hair coloring agents may containequestering agents, pH adjustors, oxidizing agents and/or water may be contained besides the compositions blended in hair colorings of the present invention. As sequestering agents, e.g. hydroxyethane diphosphonic acid may be exemplified. As pH adjustors, the salt of phosphoric acid (for example, dibasic sodium phosphate) may be exemplified. As oxidizing agents, hydrogen peroxide may be exemplified.

In formulations of No. 2 agents of oxidizing hair coloring agents, the compositions blended in hair colorings may be contained, for example, from 1 to 15 wt. %, desirably from 2 to 10 wt. %.

As the substantial method to prepare No. 2 agents of oxidizing hair coloring agents, following method may be exemplified. That is, for example, the compositions blended in hair colorings of the present invention, which are heated and dissolved homogeneously, are added to hot water and stirred to emulsify. After cooled down with constant stirring, additives such as sequestering agents, pH adjustors and oxidizing agents may be added. The heating temperature of water and the compositions blended in hair colorings is lower than the decomposition temperatures of the ingredients, for example, desirably lower than 95° C.

The oxidizing hair coloring agents of the present invention contain at least one selected from the group consisting of No. 1 agents of oxidizing hair coloring agents of the present invention and No. 2 agents of oxidizing hair coloring agents of the present invention.

For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones, and the hair colorings consisting of No. 1 agents of oxidizing hair coloring agents except the above-mentioned ones and No. 2 agents of oxidizing hair coloring agents of the present invention are included.

As "No. 1 agents of oxidizing hair coloring agents except the above-mentioned ones" and "No. 2 agents of oxidizing hair coloring agents except the above-mentioned ones", No. 1 agents and No. 2 agents that are generally used for the usual hair colorings may be exemplified respectively.

As another hair colorings of the present invention, acidic hair coloring materials may be exemplified. The acidic hair coloring materials may contain additives compositions, gum substances, organic solvents, preservatives, colors, perfumes and water may be contained besides the present compositions blended in hair colorings. As additives compositions, gum substances, preservatives, color, and perfumes, the compounds indicated in the compositions blended in hair conditioners may be exemplified respectively. As organic solvents, benzyl alcohol may be exemplified.

In formulations of the acidic hair coloring materials, the contents of the compositions blended in hair colorings are, for example, from 10 to 30 wt. %, desirably from 10 to 20 wt. %.

As the substantial method to prepare the acidic hair coloring materials of the present invention, following method may be exemplified. That is, for example, tar colors and gum substances are dissolved in hot water to prepare aqueous solution. On the other hand, additive compositions are added to the compositions blended in hair colorings, and dissolved homogeneously with constant stirring under heating. And, this homogeneous dissolved material is added to the above-mentioned hot aqueous solution with constant stirring to emulsify. After this emulsion is cooled down, organic solvents, perfumes and preservatives etc., if necessary, are added to this emulsion. The heating temperature of water and the compositions blended in hair colorings is lower than the decomposition temperatures of the ingredients, for example, desirably lower than 90° C.

As another hair colorings, decolorizing agents may be exemplified. The decolorizing agents are generally composed of No. 1 agents and No. 2 agents. As No. 1 agents of the decolorizing agents of the present invention, for example, No. 1 agents of oxidizing hair coloring agents in which dye intermediates are not contained may be exemplified. The ingredients of the the compositions blended in hair colorings in No. 1 agents of the decolorizing agents and the preparation method of No. 1 agents of the decolorizing agents may be the same as the case of No. 1 agents of oxidizing hair coloring agents. As No. 2 agents of the decolorizing agents, No. 2 agents of oxidizing hair coloring agents may be used.

As waving agents of the present invention, one that are composed of No. 1 agents and No. 2 agents may be exemplified (in the present invention, both No. 1 agents alone and No. 2 agents alone are also comprised in the treating agents of the present invention). No. 1 agents of the waving agents of the present invention may contain reducing agents, alkaline agents and water besides the compositions blended in waving agents of the present invention.

As reducing agents, thioglycolic acid, cysteine, and/or salts (ammonium salt, MEA salt, hydrochloric acd salts etc.) of them may be exemplified. As alkaline agents, ammonia, amines (MEA, isopropanolamine, etc.), ammonium salts (ammonium bicarbonate etc.) and basic amino acid may be exemplified.

In formulations of No. 1 agents of the present waving agents, the contents of the compositions blended in waving agents are, for example, from 10 to 25 wt. %, desirably 15 to 20 wt. %.

As the substantial method to prepare No. 1 agents of the present waving agents, following method may be exemplified. That is, for example, the compositions blended in waving agents, which are heated and dissolved homogeneously, are added to hot water, stirred and emulsified. After cooled down, reducing agents and alkaline agents may be added with stirring. The heating temperature of water and the compositions blended in waving agents are lower than the decomposition temperatures of the ingredients, for example, desirably lower than 95° C.

In No. 2 agents of the waving agents of the present invention, oxidizing agents, surfactants, organic acids, inorganic acids, sequestering agents and/or water may be contained besides the compositions blended in waving agents of the present invention. As oxidizing agents, salts of bromic acid and/or hydrogen peroxide may be exemplified. As surfactants, lauryl trimethyl ammonium halide (lauryl trimethyl ammonium chloride, lauryl trimethyl ammonium bromide etc.) may be exemplified. As organic acids, citric acid and/or tartaric acid may be exemplified. As inorganic acids, phosphoric acid and/or dibasic sodium phosphate may be exemplified. Further, as sequestering agents, e.g. hydroxyethane diphosphonic acid may be exemplified.

In formulations of No. 2 agents of the waving agents of the present invention, the contents of the compositions blended in waving agents are, for example, from 10 to 25 wt. %.

As the substantial method to prepare No. 2 agents of the present waving agents, following method may be exemplified. That is, for example, the compositions blended in waving agents, which are heated and dissolved homogeneously, are added to hot water, stirred and emulsified. After cooled down, oxidizing agents and cationic surfactants may be added with stirring. The heating temperature of water and the compositions blended in waving agents are lower than the decomposition temperatures of the ingredients, for example, desirably lower than 95° C.

The waving agents of the present invention contain at least one selected from the group consisting of No. 1 agents of waving agents of the present invention and No. 2 agents of waving agents of the present invention. For example, the waving agents of the present invention is one consisting of No. 1 agents of waving agents of the present invention and No. 2 agents of waving agents of the present invention, one consisting of No. 1 agents of waving agents of the present invention and No. 2 agents of waving agents except the above-mentioned ones, and another one consisting of No. 1 agents of waving agents except the above-mentioned ones and No. 2 agents of waving agents of the present invention.

As "No. 1 agents of waving agents except the above-mentioned ones" and "No. 2 agents of waving agents except the above-mentioned ones", the No. 1 and No. 2 agents that are ordinary used in the conventional waving agents may be exemplified respectively. Concretely, as No. 2 agents of waving agents except the above-mentioned ones, the mixtures prepared by dissolving oxidizing agents and surfactants homogeneously in water may be exemplified.

The finishing agents of the present invention contain the compositions blended in finishing agents, and generally further contain water. Further, as additives, silicones, alkaline agents, nonionic surfactants (polyoxyethylene derivatives prepared from natural fats and oils etc.), waxes, glycols, esters (e.g. higher fatty acid esters), and the compounds indicated as additives in hair conditioners may be added.

For example, by adding silicones, hair treating effects such as vanishing ability, well spread of cream, setting ability and feeling effect (luster, smooth feel, slightly oily feel etc.) may be more excellent, and further, flaking may be keeped down.

As such silicones, silicones whose viscosity, for example, have 10–1000 cs, desirably 20–500 cs may be exemplified. Concretely, as silicones, methyl polysiloxane and/or methylphenyl polysiloxane may be used.

As alkaline agents, inorganic and organic alkaline agents may be exemplified. Concretely, as inorganic alkaline agents, sodium hydroxide and potassium hydroxide may be exemplified. As organic alkaline agents, primary amines, secondary amines and tertiary amines may be exemplified. Concretely, as organic alkaline agents, monoethanolamine, triethanolamine (TEA) and 2-amino-2-methyl-1-propanol may be exemplified.

In formulations of the finishing agents of the present invention, the contents of the compositions blended in finishing agents are, for example, from 1 to 35 wt. %.

As the substantial method to prepare the finishing agents of the present invention, following method may be exemplified. That is, for example, inorganic alkaline agents are dissolved in water and heated. On the other hand, additives, if necessary, such as nonionic surfactants, waxes, glycols and preservatives are added to the compositions blended in finishing agents and dissolved homogeneously with constant stirring under heating, and then, silicones and esters, if necessary, are added to this solution to disperse.

And, this homogeneous dispersion is added to the above-mentioned hot alkaline aqueous solution with constant stirring to emulsify. After this emulsion is cooled down, perfumes etc., if necessary, are added to this emulsion. The heating temperature of water and the compositions blended in finishing agents are lower than the decomposition temperatures of the ingredients, for example, desirably lower than 95° C.

The Fifth Embodiment

In this embodiment, alcohols and cationic surfactants besides esters are contained in the compositions blended in hair treating agents.

As esters, fatty esters of polyhydric alcohols, higher fatty esters, and natural fatty esters may be exemplified. Concretely, one to four compounds selected from the group consisting of ethylene glycol monostearate, ethylene glycol distearate, polyethylene glycol distearate, neopentyl glycol dicaprate, lipophilic glyceryl monostearate, lipophilic glyceryl monooleate, cetyl octate, hexyl laurate, isopropyl myristate, isopropyl palmitate, diisopropyl adipate, cetyl lactate and lanolin fatty acid isopropyl ester may be exemplified.

For example, in the compositions blended in hair conditioners, in the compositions blended in hair colorings, in the compositions blended in waving agents, in the compositions blended in finishing agents and in the compositions blended in color fixing agents, lipophilic glyceryl monostearate and/or isopropyl myristate may be contained as esters.

Further, in the compositions blended in hair treating agents of the present invention, alcohols are contained. As alcohols, for example, higher alcohols, polyhydric alcohols and natural alcohos etc. may be exemplified. Concretely, one to three compounds selected from the group consisting of cetanol, stearyl alcohol, oleyl alcohol, octyldodecanol, behenyl alcohol, 1,3-butylene glycol, dipropylene glycol, glycerin (concentrated glycelin etc.), cetostearyl alcohol, lanolin alcohol and phytosterol may be exemplified.

For example, in the compositions blended in hair conditioners, in the compositions blended in hair colorings, in the compositions blended in waving agents, in the compositions blended in finishing agents and in the compositions blended in color fixing agents, one to three compounds selected from the group consisting of cetanol, stearyl alcohol, and oleyl alcohol may be contained as alcohols.

Further, in the compositions blended in hair treating agents of the present invention, cationic surfactants are contained. As the cationic surfactants, e.g. alkyl trimethyl ammonium halide and/or salts of alkyl sulfate/fatty acid amide alkyl ammonium may be exemplified. As the substantial example, one or two compounds selected from the group consisting of lauryl trimethyl ammonium bromide, stearyl trimethyl ammonium chloride, cetyl trimethyl ammonium chloride, cetyl trimethyl ammonium bromide and behenyl trimethyl ammonium chloride may be exemplified.

For example, in the compositions blended in hair conditioners, in the compositions blended in hair colorings, in the compositions blended in waving agents, in the compositions blended in finishing agents and in the compositions blended in color fixing agents, one or two compounds selected from the group consisting of stearyl trimethyl ammonium chroride, cetyl trimethyl ammonium chloride and behenyl trimethyl ammonium chloride may be contained as cationic surfactants.

Further, in the compositions blended in hair treating agents of the present invention, any kind of additives may be contained in accordance with the kind of hair treating agents and the purposes.

For example, in the compositions blended in hair treating agents of the present invention, additives such as fats and oils may be contained. Concretely, as fats and oils, one to three compounds selected from the group consisting of lanolin, hard lanolin, hydrogenated oil (hydrogenated palm oil fatty acid triglyceride, hydrogenated tallow acid triglyceride etc.), mink oil, olive oil, hydrogenated jojoba oil, hydrogenated castor oil and safflower oil may be exemplified.

Concretely, in the compositions blended in hair conditioners, in the compositions blended in hair colorings, in the compositions blended in waving agents, in the compositions blended in finishing agents and in the compositions blended in color fixing agents, hydrogenated oil and/or olive oil may be contained as fats and oils.

As another additives, fatty acids, hydrocarbons, waxes, amphoteric surfactants, sequestering agents, active agents like vitamin, antioxidant, polyethers, and silicones may be contained in the compositions blended in hair treating agents of the present invention, As the above-mentioned fatty acids, stearic acid and isostearic acid may be exemplified. As the above-mentioned hydrocarbons, vegetable squalane, paraffin, liquid petrolatum and vaseline may be exemplified. As the above-mentioned waxes, carnauba wax and beeswax may be exemplified. As the above-mentioned amphoteric surfactants, stearyl dimethyl glycine may be exemplified. As the above-mentioned sequestering agents, disodium edetate may be exemplified. As the above-mentioned active agents like vitamin, γ-oryzanol may be exemplified. As the above-mentioned antioxidants, dibutylhydroxytoluene may be exemplified. As the above-mentioned polyethers, polyoxypropylene (30–50 PO) butyl ether may be exemplified. As the above-mentioned silicones, methylphenyl polysiloxane may be exemplified. In the compositions blended in hair treating agents of the present invention, one to four kinds of compounds selected from them may be contained.

In the formulations of the compositions blended in hair treating agents of the present invention, when the respective contents of esters, alcohols, and cationic surfactants are N, O and P (wt. %) respectively, it is desirable for N–P to be within following ranges; $1 \leq N \leq 55$, $10 \leq O \leq 65$, $5 \leq P \leq 35$, and $N+O+P \leq 100$.

When N is smaller than 1, oil rich feel may be insufficient. Inversely, when N is larger than 55, oil rich feel may be too strong. When O is small than 10, the viscosity may be insufficient. Inversely, when O is larger than 65, the compositions may be too hard. When P is smaller than 5, feel in rinsing may be bad. Inversely, when P is larger than 35, stickiness may be arisen.

As the substantial method to prepare the compositions of this embodiment blended in hair treating agents, following method may be exemplified. That is, esters, alcohols, cationic surfactants, and ingredients (if necessary) such as additives are mixed and stirred under heating until completely dissolved. The heating temperature is desirably lower than the decomposition temperatures of the mixture, for example, lower than 100° C., desirably lower than 90° C. The adding order of each ingredients are not limited.

The hair treating agents of the present invention contain the compositions blended in hair treating agents of the present invention. Hair conditioners, hair colorings, waving agents, finishing agents and color fixing agents are illustrated below as the hair treating agents, .

The hair conditioners of the present invention contain above-mentioned compositions blended in hair conditioners. As the compositions blended in hair conditioners, one or more kinds may be used.

Further, in the hair conditioners of the present invention, water, additive compositions, preservatives, perfumes, aqueous solutions of polypeptide (PPT), colors, glycols, organic acids, humectants, antioxidants, sequestering agents, hydrolysed animal proteins, pH adjustors and aqueous useful substances may be contained.

As additive compositions, for example, mixtures with animal fats and oils (mink oil etc.), fatty esters and silicones may be exemplified. As preservatives, parabens such as methylparaben or propylparaben may be exemplified. As colors and perfumes, any kinds of colors and perfumes that are generally used to the hair conditioners may be exemplified. As glycols, glycerin may be exemplified. As organic acids, lactic acid and citric acid may be exemplified. As humectants, sodium pyrrolidonecarboxylate (PCA soda) may be exemplified. As antioxidants, dibutylhydroxytoluene may be exemplified. As the sequestering agents, e.g. disodium edetate may be exemplified. As pH adjustors, levulinic acid, citric acid and phosphoric acid may be exemplified. As aqueous useful substances, vegetable extracts may be exemplified.

In the formulations of the hair conditioners of the present invention, the compositions blended in hair conditioners are, for example, from 5 to 30 wt. %.

The preparing method of the hair conditioners of the present invention is not limited. For example, the compositions blended in the hair conditioners of the present invention, which are heated and dissolved homogeneously, are added to hot water which contains glycols (if necessary) and stirred to emulsify. After cooled down with constant stirring, additives may be added. The heating temperature of water and the compositions blended in the hair conditioners is lower than the decomposition temperatures of the ingredients, for example, lower than 90° C.

As hair colorings of the present invention, oxidizing hair coloring agents may be exemplified. The oxidizing hair coloring agents are composed of No. 1 agents and No. 2 agents (in the present invention, No. 1 agents alone and No. 2 agents alone are also comprised in the hair colorings of the present invention). No. 1 agents of the oxidizing hair coloring agents of the present invention may contain water, alcohols, solvents, dye intermediates, alkaline agents, antioxidants, and sequestering agents besides the compositions blended in hair colorings of the present invention. As alcohols, cetanol may be exemplified. As solvents, N-methl-2-pyrrolidone (NMP) may be exemplified. As dye intermediates, for example, phenylene diamines (e.g. ortho, meta, para phenylene diamine), phenols (e.g. ortho, meta, para aminophenol, nitrophenols) and aminocresols may be exemplified. As alkaline agents, aqueous ammonia, and MEA (monoethanolamine) may be exemplified. As antioxidants, the compounds that are used to the ordinary oxidizing hair coloring agents such as sodium sulfite, ammonium thioglycolate, ascorbic acid or cysteine may be exemplified. As the sequestering agents, e.g. salt of EDTA and hydroxyethane diphosphonic acid may be exemplified.

In the formulations of No. 1 agents of oxidizing hair coloring agents, the contents of the compositions blended in hair colorings are, for example, from 10 to 35 wt. %, desirably from 20 to 30 wt. %.

As the substantial method to prepare No. 1 agents of oxidizing hair coloring agents, following method may be exemplified. That is, for example, dye intermediates and antioxidants are poured into hot water and prepare homogeneous aqueous solution, then the compositions blended in hair colorings, which are heated and dissolved homogeneously, are added and mixed. After cooled down, additives such as alkaline agents and sequestering agents may be added to the mixture by constant stirring. The heating temperature of water and the compositions blended in hair colorings is lower than decomposition temperatures of the ingredients, for example, desirably lower than 95° C.

No. 2 agents of oxidizing hair coloring agents may contain water, alcohols, oxidizing agents, sequestering agents, and pH adjustors besides the compositions blended in hair colorings of the present invention. As alcohols, cetanol may be exemplified. As oxidizing agents, hydrogen peroxide may be exemplified. As the sequestering agents, e.g. hydroxyethane diphosphonic acid may be exemplified. As pH adjustors, salts of phosphoric acid (for example, dibasic sodium phosphate) may be exemplified.

In formulations of No. 2 agents of oxidizing hair coloring agents, the compositions blended in hair colorings may be contained, for example, from 1 to 15 wt. %, desirably from 2 to 10 wt. %.

As the substantial method to prepare No. 2 agents of oxidizing hair coloring agents, following method may be exemplified. That is, for example, the compositions blended in hair colorings of the present invention, which are heated and dissolved homogeneously, are added to hot water and stirred to emulsify. After cooled down with constant stirring, additives such as sequestering agents, pH adjustors and oxidizing agents may be added. The heating temperature of water and the compositions blended in hair colorings is lower than the decomposition temperatures of the ingredients, for example, desirably lower than 95° C.

The oxidizing hair coloring agents of the present invention contain at least one selected from the group consisting of No. 1 agents of oxidizing hair coloring agents of the present invention and No. 2 agents of oxidizing hair coloring agents of the present invention. For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones, and the hair colorings consisting of No. 1 agents of oxidizing hair coloring agents except the above-mentioned ones and No. 2 agents of oxidizing hair coloring agents of the present invention are included.

As "No. 1 agents of oxidizing hair coloring agents except the above-mentioned ones" and "No. 2 agents of oxidizing hair coloring agents except the above-mentioned ones", No. 1 agents and No. 2 agents which are generally used for the usual hair colorings may be exemplified respectively.

As another hair colorings, decolorizing agents may be exemplified. The decolorizing agents are generally composed of No. 1 agents and No. 2 agents. As No. 1 agents of the decolorizing agents of the present invention, for example, No. 1 agents of oxidizing hair coloring agents in which dye intermediates are not contained may be exemplified. The ingredients of the the compositions blended in hair colorings in No. 1 agents of the decolorizing agents and the preparation method of No. 1 agents of the decolorizing agents may be the same as the case of No. 1 agents of oxidizing hair coloring agents. As No. 2 agents of the decolorizing agents, No. 2 agents of oxidizing hair coloring agents may be used.

As waving agents of the present invention, the cationic waving agents may be exemplified. The cationic waving agents are generally composed of No. 1 agents and No. 2 agents (in the present invention, both No. 1 agents alone and No. 2 agents alone are also comprised in the waving agents of the present invention). No. 1 agents of the cationic waving agents of the present invention may contain water, alcohols, reducing agents, and alkaline agents besides the compositions blended in waving agents of the present invention. As alcohols, cetanol may be exemplified. As reducing agents, thioglycolic acid and cysteine or salts (ammonium salt, MEA salt hydrochloric acid salts etc.) of them may be exemplified. As alkaline agents, ammonia, amines (MEA, isopropanolamine etc.), ammonium salts (ammonium bicarbonate etc.) and basic amino acid may be exemplified.

In formulations of No. 1 agents of the cationic waving agents, the contents of the compositions blended in waving agents are, for example, from 10 to 25 wt. %, desirably 15 to 20 wt. %.

As the substantial method to prepare No. 1 agents of the cationic waving agents, following method may be exemplified. That is, for example, the compositions blended in waving agents, which are heated and dissolved homogeneously, are added to hot water, stirred and emulsified. After cooled down, reducing agents and alkaline agents may be added. The heating temperature of water and the compositions blended in waving agents are lower than the decomposition temperatures of the ingredients, for example, desirably lower than 95° C.

In No. 2 agents of the cationic waving agents of the present invention, water, alcohols, oxidizing agents, organic acids, cationic surfactants, inorganic acids, or sequestering agents may be contained besides the compositions blended in waving agents of the present invention. As alcohols, cetanol may be exemplified. As oxidizing agents, salts of bromic acid or hydrogen peroxide may be exemplified. As organic acids, citric acid or tartaric acid may be exemplified. As cationic surfactants, lauryl trimethyl ammonium halide (lauryl trimethyl ammonium chloride, lauryl trimethyl ammonium bromide etc.) may be exemplified. As inorganic acids, phosphoric acid or dibasic sodium phosphate may be exemplified. Further, as sequestering agents, e.g. hydroxyethane diphosphonic acid may be exemplified.

In formulations of No. 2 agents of the cationic waving agents, the contents of the compositions blended in waving agents are, for example, from 10 to 25 wt. %.

As the substantial method to prepare No. 2 agents of the cationic waving agents of the present invention, following method may be exemplified. That is, for example, the compositions blended in waving agents, which are heated and dissolved homogeneously are added to hot water, stirred and emulsified. After cooled down, oxidizing agents, organic acids, cationic surfactants, inorganic acids and sequestering agents may be added. The heating temperature of water and the compositions blended in waving agents are lower than the decomposition temperatures of the ingredients, for example, desirably lower than 95° C.

The cationic waving agents of the present invention contain at least one selected from the group consisting of No. 1 agents of the present invention of cationic waving agents and No. 2 agents of the present invention of cationic waving agents. For example, the cationic waving agents of the present invention is one consisting of No. 1 agents of cationic waving agents of the present invention and No. 2 agents of cationic waving agents of the present invention, one consisting of No. 1 agents of cationic waving agents of the present invention and No. 2 agents of cationic waving agents except the above-mentioned ones and another one consisting of No. 1 agents of cationic waving agents except the above-mentioned ones and No. 2 agents of cationic waving agents of the present invention.

As "No. 1 agents of waving agents except the above-mentioned ones" and "No. 2 agents of waving agents except the above-mentioned ones", the No. 1 and No. 2 agents that are ordinary used in the conventional waving agents may be exemplified. Concretely, as No. 2 agents of waving agents except the above-mentioned ones, the mixture prepared by dissolving oxidizing agents and cationic surfactants homogeneously in water may be exemplified.

The finishing agents of the present invention contain the compositions blended in finishing agents, and generally further contain water. And, as additives, the compounds indicated in hair conditioners may be voluntarily added.

In formulations of the finishing agents of the present invention, the contents of the compositions blended in finishing agents are, for example, from 1 to 10 wt. %.

The preparation method of the finishing agents of the present invention may be the same as the preparation method of the hair conditioners.

Color fixing agents of the present invention can prevent fading dye. In the color fixing agents of the present invention, additives such as preservatives (parabenes etc.), organic acids (tannic acid, glycolic acid etc.), and inorganic acids (phosphoric acid etc.) and water may be contained besides the compositions blended in color fixing agents.

In formulations of the color fixing agents of the present invention, the contents of the compositions blended in the color fixing agents are, for example, from 10 to 20 wt. %.

As the substantial method to prepare the color fixing agents of the present invention, following method may be exemplified. For example, the homogeneous mixture is prepared by mixing the compositions blended in the color fixing agents with preservatives under heating. Then this mixture is added to hot water with stirring under heating to emulsify. After this emulsion is cooled down with stirring, additives, if necessary, may be added to this. The heating temperature of water and the compositions blended in the color fixing agents are lower than the decomposition temperatures of the ingredients, for example, desirably lower than 95° C.

The Sixth Embodiment

In this embodiment, alcohols, cationic surfactants, and nonionic surfactants besides esters are contained in the compositions blended in hair treating agents.

As esters, fatty esters of polyhydric alcohols (e.g. ethylene glycol, glycerin, pentaerithritol etc.), higher fatty esters and natural fatty esters may be exemplified. Concretely, one to three compounds selected from the group consisting of polyethylene glycol distearate, mono and diglyceryl oleate and stearate, lipophilic glyceryl monostearate, glyceryl cocoate, fatty esters of dipentaerythritol (e.g. the full ester prepared from pentaerithritol and a mixture of fatty acids etc.), hexyl laurate, isopropyl myristate, isopropyl palmitate, octyl palmitate, butyl stearate, diisostearyl malate and diisopropyl adipate may be exemplified.

Concretely, in the compositions blended in hair conditioners, in the compositions blended in waving agents and in the compositions blended in color fixing agents, lipophilic glyceryl monostearate may be contained. In the compositions blended in hair conditioners, in the compositions blended in hair colorings, in the compositions blended in waving agents, and in the compositions blended in finishing agents, isopropyl myristate may be contained.

Further, in the compositions blended in hair treating agents of the present invention, alcohols are contained. As alcohols, for example, lower and higher alcohols, mixture of side chain higher fatty alcohols, polyhydric alcohols and natural alcohols etc. may be exemplified. Concretely, one, two, three, or six kinds of compounds selected from the group consisting of isopropanol, lauryl alcohol, cetanol, stearyl alcohols, oleyl alcohol, octyldodecanol, behenyl alcohol, mixtures of side chain higher fatty alcohols (e.g. C32–C36), propylene glycol, dipropylene glycol, 1,3-butylene glycol, glycerin, cetostearyl alcohol and lanolin alcohol may be exemplified.

For example, in the compositions blended in hair conditioners, in the compositions blended in hair colorings, in the compositions blended in waving agents, and in the compositions blended in finishing agents, cetanol may be contained.

Further, in the compositions blended in hair treating agents of the present invention, cationic surfactants are contained. As the cationic surfactants, e.g. quaternary ammonium salts, which are substituted by hydrocarbon radical and/or polyoxethylene substituting group, and pyridinium salts may be exemplified. In the polyoxyethylene substituting group, addition polymerization degree of ethylene oxide (EO) may be, for example, 2–5 moles. As the substantial example of cationic surfactants, one or two compounds selected from the group consisting of stearyl trimethyl ammonium chloride, cetyl trimethyl ammonium chloride, cetyl trimethyl ammonium bromide, behenyl trimethyl ammonium chloride, distearyl dimethyl ammonium chloride, dipolyoxyethylene oleyl methyl ammonium chloride, benzalkonium chloride, and cetyl pyridinium chloride may be exemplified.

Concretely, in the compositions blended in hair conditioners and in the compositions blended in hair colorings, e.g. stearyl trimethyl ammonium chloride may be contained. In the compositions blended in hair conditioners, in the compositions blended in hair colorings, in the compositions blended in waving agents, and in the compositions blended in finishing agents, for example, cetyl trimethyl ammonium chloride may be contained.

Further, in the compositions blended in hair treating agents of the present invention, nonionic surfactants are contained As an nonionic surfactants, polyoxyethylene alkyl ether, polyoxyethylene alkenyl ether, polyoxyethylene alkyl aryl ether, polyoxyethylene derivatives prepared from natural fatty acid, alkylolamides, sorbitan fatty ester or tertiary amines may be exemplified. As the above-mentioned polyoxyethylene ether, e.g. 2 to 45 moles of ethylene oxide (EO) addition polymerizated product (i. e. 2 to 45 moles EO adducts) may be exemplified.

Concretely, one, two or four kinds of compounds selected from the groups consisting of polyoxyethylene lauryl ether, polyoxyethylene cetyl ether, polyoxyethylene oleyl ether, polyoxyethylene nonylphenyl ether, polyoxyethylene castor oil, polyoxyethylene hydrogenated castor oil, stearic acid monoethanolamide, coconut fatty acid monoethanolamide, sorbitan trioleate and dimethyl stearylamine may be exemplified.

Concretely, in the compositions blended in hair conditioners, in the compositions blended in hair colorings, in the compositions blended in waving agents, and in the compositions blended in color fixing agents, for example, polyoxyethylene cetyl ether may be contained. In the compositions blended in hair conditioners and in the compositions blended in hair colorings, for example, polyoxyethylene oleyl ether may be contained.

Further, in the compositions blended in hair treating agents of the present invention, any kind of additives may be contained in accordance with the kinds of hair treating agents and the purposes.

For example, in the compositions blended in hair treating agents of the present invention, additives such as hydrocarbons may be contained. As hydrocarbons, one or two kinds of compounds selected from the group consisting of paraffin, liquid petrolatum, light liquid isoparaffin, ceresine and α-olefin oligomers may be exemplified. As α-olefin oligomers, side chain hydrocarbons, which are obtained by polymerizing, for example, C4–C12 linear aliphatic α-olefin, and have polymerization degree of, for example, 3–6 of α-olefin, may be exemplified.

For example, in the compositions blended in hair conditioners, in the compositions blended in hair colorings, in the compositions blended in waving agents, in the compositions blended in finishing agents, and in the compositions blended in color fixing agents, paraffin may be contained.

Further, in the compositions blended in hair treating agents of the present invention, one or two kinds of compounds selected from the group consisting of anionic surfactants, fatty acids, waxes, organic acids, silicones and water may be contained as additives. Concretely, as anionic surfactants, sodium lauryl sulfate may be exemplified. As fatty acids, stearic acid or hard lanolin fatty acid may be exemplified. As waxes, carnauba wax may be exemplified. As organic acids, lactic acid may be exemplified. As silicone, methylphenyl polysiloxane may be exemplified.

For example, in the compositions blended in hair conditioners, one or two kinds of compound selected from anionic surfactants, fatty acids, waxes, organic acids, silicones and water may be contained. In the compositions blended in hair colorings, fatty acids may be contained.

In the formulations of the compositions blended in hair treating agents of the present invention, when the respective contents of esters, alcohols, cationic surfactants and nonionic surfactants are Q, R, S and T (wt. %) respectively, it is desirable for Q–T to be within following ranges; $1 \leq Q \leq 30$, $10 \leq R \leq 75$, $0.1 \leq S \leq 30$, $1 \leq T \leq 65$ and $Q+R+S+T \leq 100$.

For example, in the compositions blended in hair conditioners and in the compositions blended in color fixing agents, Q, R, S and T may be $3 \leq Q \leq 30$, $10 \leq R \leq 65$, $0.1 \leq S \leq 30$, $1 \leq T \leq 65$ and $Q+R+S+T \leq 100$.

For example, in the compositions blended in hair colorings, Q, R, S and T may be $5 \leq Q \leq 15$, $20 \leq R \leq 60$, $5 \leq S \leq 25$, $1 \leq T \leq 20$ and $Q+R+S+T \leq 100$.

For example, in the compositions blended in waving agents, and in the compositions blended in finishing agents, Q, R, S and T may be $3 \leq Q \leq 23$, $45 \leq R \leq 75$, $7 \leq S \leq 30$, $1 \leq T \leq 8$ and $Q+R+S+T \leq 100$.

As the substantial method to prepare the compositions of this embodiment blended in hair treating agents, following method may be exemplified. That is, esters, alcohols, cationic surfactants, nonionic surfactants, and ingredients such as additives (if necessary) are mixed and stirred under heating until completely dissolved.

The heating temperature is desirably lower than the decomposition temperatures of the mixture, for example, lower than 100° C., desirably lower than 90° C. The adding order of each ingredients are not limited.

The hair treating agents of the present invention contain the compositions blended in hair treating agents of the present invention. As the hair treating agents, hair conditioners, hair colorings, waving agents, finishing agents, and color fixing agents are illustrated below.

The hair conditioners of the present invention contain above-mentioned compositions blended in hair conditioners. As the compositions blended in hair conditioners, one or more kinds may be used.

Further, in the hair conditioners of the present invention, polyhydric alcohols, additive compositions, preservatives, aqueous solutions of polypeptide (PPT), colors, perfumes, silicones, water, and organic acids may be contained. As polyhydric alcohols, e.g. propylene glycol, buthylene glycol, glycerin etc. may be exemplified. As additive compositions, for example, mixture of fatty esters, alcohols, any type of surfactants and silicones may be exemplified. As preservatives, parabens such as methylparaben or propylparaben may be exemplified. As colors and perfumes, any kinds of colors and perfumes that are generally used to the hair conditioners may be exemplified. As silicones, methyl polysiloxane may be exemplified.

In the formulations of the hair conditioners of the present invention, the contents of the compositions blended in hair conditioners are, for example, from 5 to 40 wt. %.

The preparing method of the hair conditioners of the present invention is not limited. For example, the compositions blended in the hair conditioners of the present invention, which are heated and dissolved homogeneously, are added to hot water with constant stirring to emulsify. After cooled down, additives may be added.

As another preparing method of the hair conditioners of the present invention, for example, any kind of additives is added to the compositions blended in the hair conditioners of the present invention, which are heated and dissolved homogeneously, and then water may be added to emulsify homogeneously.

The heating temperature of water and the compositions blended in the hair conditioners is lower than the decomposition temperatures of the ingredients, for example, lower than 95° C.

As hair colorings of the present invention, oxidizing hair coloring agents may be exemplified. The oxidizing hair coloring agents are composed of No. 1 agents and No. 2 agents (in the present invention, No. 1 agents alone and No. 2 agents alone are also comprised in the hair colorings of the present invention). No. 1 agents of the oxidizing hair coloring agents of the present invention may contain dye intermediates, alkaline agents, antioxidants, sequestering agents, and water besides the compositions blended in hair colorings of the present invention. As dye intermediates, for example, phenylene diamines (e.g. ortho, meta, para phenylene diamine), phenols (e.g. ortho, meta, para aminophenol, nitrophenols) and aminocresols may be exemplified. As alkaline agents, aqueous ammonia, and monoethanolamine (MEA) may be exemplified. As antioxidants, the compounds, that are used to the ordinary oxidizing hair coloring agents, such as sodium sulfite, ammonium thioglycolate, ascorbic acid or cysteine may be exemplified. As the sequestering agents, e.g. EDTA and hydroxyethane diphosphonic acid may be exemplified.

In the formulations of No. 1 agents of oxidizing hair coloring agents, the contents of the compositions blended in hair colorings are, for example, from 10 to 35 wt. %, desirably from 15 to 30 wt. %.

As the substantial method to prepare No. 1 agents of oxidizing hair coloring agents, following method may be exemplified. That is, for example, dye intermediates and antioxidants are poured into hot water and prepare homogeneous aqueous solution, then the compositions blended in hair colorings, which are heated and dissolved homogeneously, are added and mixed. After cooled down, additives such as alkaline agents and sequestering agents may be added to the mixture by constant stirring. The heating temperature of water and the compositions blended in hair colorings is lower than decomposition temperatures of the ingredients, for example, desirably lower than 95° C.

No. 2 agents of oxidizing hair coloring agents of the present invention may contain oxidizing agents, sequestering agents, pH adjustors and water besides the compositions blended in hair colorings of the present invention. As oxidizing agents, hydrogen peroxide may be exemplified. As the sequestering agents, e.g. hydroxyethane diphosphonic acid may be exemplified. As pH adjustors, salts of phosphoric acid (for example, dibasic sodium phosphate) may be exemplified.

In formulations of No. 2 agents of oxidizing hair coloring agents, the compositions blended in hair colorings may be contained, for example, from 1 to 15 wt. %, desirably from 2 to 10 wt. %.

As the substantial method to prepare No. 2 agents of oxidizing hair coloring agents, following method may be exemplified. That is, for example, the compositions blended in hair colorings of the present invention, which are heated and dissolved homogeneously, are added to hot water and stirred to emulsify. After cooled down with constant stirring, additives such as sequestering agents, pH adjustors and oxidizing agents may be added. The heating temperature of water and the compositions blended in hair colorings is lower than the decomposition temperatures of the ingredients, for example, desirably lower than 95° C.

The oxidizing hair coloring agents of the present invention contain at least one selected from the group consisting of No. 1 agents of oxidizing hair coloring agents of the present invention and No. 2 agents of oxidizing hair coloring agents of the present invention. For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones and the hair colorings consisting of No. 1 agents of oxidizing hair coloring agents except the above-mentioned ones and No. 2 agents of oxidizing hair coloring agents of the present invention are included.

As "No. 1 agents of oxidizing hair coloring agents except the above-mentioned ones" and "No. 2 agents of oxidizing hair coloring agents except the above-mentioned ones", No. 1 agents and No. 2 agents which are generally used for the usual hair colorings may be exemplified respectively.

As another hair colorings, decolorizing agents may be exemplified. The decolorizing agents are generally composed of No. 1 agents and No. 2 agents. As No. 1 agents of the decolorizing agents of the present invention, for example, No. 1 agents of oxidizing hair coloring agents in which dye intermediates are not contained may be exemplified. The formulations of the the compositions blended in hair colorings in No. 1 agents of the decolorizing agents and the preparation method of No. 1 agents of the decolorizing agents may be the same as the case of No. 1 agents of oxidizing hair coloring agents. As No. 2 agents of the decolorizing agents, No. 2 agents of oxidizing hair coloring agents may be used.

As waving agents of the present invention, the cationic waving agents may be exemplified. The cationic waving agents are generally composed of No. 1 agents and No. 2 agents (in the present invention, both No. 1 agents alone and No. 2 agents alone are also comprised in the waving agents of the present invention). No. 1 agents of the cationic waving agents of the present invention may contain reducing agents, disulfide compounds, alkaline agents, inorganic acids and water besides the compositions blended in waving agents of the present invention. As reducing agents, thioglycolic acid and cysteine or salts (ammonium salt, MEA salt hydrochloric acid salts etc.) of them may be exemplified. As disulfide compounds, diammonium dithiodiglycolate may be exemplified. As alkaline agents, ammonia, amines (MEA, isopropanolamine etc.), ammonium salts (ammonium bicarbonate etc.) and basic amino acid may be exemplified. As inorganic acids, dibasic sodium phosphate may be exemplified.

In formulations of No. 1 agents of the cationic waving agents, the contents of the compositions blended in waving agents are, for example, from 10 to 20 wt. %.

As the substantial method to prepare No. 1 agents of the cationic waving agents, following method may be exemplified. That is, for example, the compositions blended in waving agents, which are heated and dissolved homogeneously, are added to hot water, stirred and emulsified. After cooled down, reducing agents and alkaline agents may be added with stirring. The heating temperature of water and the compositions blended in waving agents are lower than the decomposition temperatures of the ingredients, for example, desirably lower than 95° C.

In No. 2 agents of the cationic waving agents of the present invention, oxidizing agents, organic acids, cationic surfactants, inorganic acids, sequestering agents, and water may be contained besides the compositions blended in waving agents. As oxidizing agents, salts of bromic acid or hydrogen peroxide may be exemplified. As organic acids, citric acid or tartaric acid may be exemplified. As cationic surfactants, lauryl trimethyl ammonium halide (lauryl trimethyl ammonium chloride, lauryl trimethyl ammonium bromide etc.) may be exemplified. As inorganic acids, phosphoric acid or dibasic sodium phosphate may be exemplified. As sequestering agents, e.g. hydroxyethane diphosphonic acid may be exemplified.

In formulations of No. 2 agents of the cationic waving agents, the contents of the compositions blended in waving agents are, for example, 0.8 to 20 wt. %, desirably 1 to 20 wt. %.

As the substantial method to prepare No. 2 agents of the cationic waving agents of the present invention, following method may be exemplified. That is, for example, the compositions blended in waving agents, which are heated and dissolved homogeneously, are added to hot water, stirred and emulsified. After cooled down, oxidizing agents, organic acids, cationic surfactants, inorganic acids and sequestering agents may be added. The heating temperature of water and the compositions blended in waving agents are lower than the decomposition temperatures of the ingredients, for example, desirably lower than 95° C.

The cationic waving agents of the present invention contain at least one selected from the group consisting of No. 1 agents of the present invention of cationic waving agents and No. 2 agents of the present invention of cationic waving agents. For example, the cationic waving agents of the present invention is one consisting of No. 1 agents of cationic waving agents of the present invention and No. 2 agents of cationic waving agents of the present invention, one consisting of No. 1 agents of cationic waving agents of the present invention and No. 2 agents of cationic waving agents except the above-mentioned ones and another one consisting of No. 1 agents of cationic waving agents except the above-mentioned ones and No. 2 agents of cationic waving agents of the present invention.

As "No. 1 agents of waving agents except the above-mentioned ones" and "No. 2 agents of waving agents except the above-mentioned ones", the No. 1 and No. 2 agents which are ordinary used in the conventional waving agents may be exemplified. Concretely, as No. 2 agents of waving agents except the above-mentioned ones, the mixture prepared by dissolving oxidizing agents and cationic surfactants homogeneously in water may be exemplified.

The finishing agents of the present invention contain the compositions blended in finishing agents, and generally further contain water. And, as additives, the compounds indicated in hair conditioners may be voluntarily added.

In formulations of the finishing agents of the present invention, the contents of the compositions blended in finishing agents are, for example, from 1 to 10 wt. %.

The preparation method of the finishing agents of the present invention may be the same as the preparation method of the hair conditioners.

Color fixing agents of the present invention can prevent fading dye. In the color fixing agents of the present invention, additives such as preservatives (parabenes etc.), organic acids (tannic acid, glycolic acid etc.), and inorganic acids (phosphoric acid etc.) and water may be contained besides the compositions blended in color fixing agents.

In formulations of the color fixing agents of the present invention, the contents of the compositions blended in the color fixing agents are, for example, from 10 to 20 wt. %.

As the substantial method to prepare the color fixing agents of the present invention, following method may be exemplified. For example, the homogeneous mixture is prepared by mixing the compositions blended in the color fixing agents with preservatives under heating. Then this mixture is added to hot water with stirring under heating to emulsify. After this emulsion is cooled down with stirring, additives, if necessary, may be added to this.

The heating temperature of water and the compositions blended in the color fixing agents are lower than the decomposition temperatures of the ingredients, for example, desirably lower than 95° C.

The Seventh Embodiment

In this embodiment, alcohols, cationic surfactants, nonionic surfactants and fats and oils besides esters are contained in the compositions blended in hair treating agents.

As esters, fatty esters of polyhydric alcohols, higher fatty esters and natural fatty esters may be exemplified. Concretely, one to three compounds selected from the group consisting of glycerin fatty ester (e.g. lipophilic glyceryl monostearate, glyceril myristate, mixture of mono and diglyceryl oleate and stearate), isopropyl myristate, isopropyl palmitate, butyl stearate, octyl hydroxystearate and lanolin fatty acid octyldodecyl ester may be exemplified.

Concretely, in the compositions blended in hair conditioners, in the compositions blended in hair colorings and in the compositions blended in waving agents and in the compositions blended in finishing agents, for example, lipophilic glyceryl monostearate and/or isopropyl myristate may be contained.

Further, in the compositions blended in hair conditioners alcohol are contained. As alcohols, for example, higher alcohols, polyhydric alcohols and natural alcohols may be exemplified. As the substantial example, one to five compounds selected from the group consisting of lauryl alcohol, octyldodecanol, oleyl alcohol, stearyl alcohol, dipropylene glycol and cetanol may be exemplified.

Concretely, in the compositions blended in hair conditioners, in the compositions blended in hair colorings, in the compositions blended in waving agents and in the compositions blended in finishing agents, oleyl alcohol and/or cetanol may be contained.

In the compositions for hair treating agents of the present invention, cationic surfactants are contained. As the cationic surfactants, e.g. alkyl trimethyl ammonium halide such as alkyl trimethyl ammonium chloride or fatty acid amidoalkyl alkyl ammonium alkyl sulfates may be exemplified. As the substantial example, one or two compounds selected from the group consisting of cetyl trimethyl ammonium chloride, cetyl trimethyl ammonium bromide, stearyl trimethyl ammonium chloride, behenyl trimethyl ammonium chloride and lanolin aminopropyl ethyl dimethyl ammonium ethylsulfate (or lanolin amidopropyl ethyl dimethyl ammonium ethylsulfate) may be exemplified.

Concretely, in the compositions blended in hair conditioners, in the compositions blended in hair colorings, in the compositions blended in waving agents, in the compositions blended in finishing agents and in the compositions blended in finishing agents cetyl trimethyl ammonium chloride and/or cetyl trimethyl ammonium bromide may be contained as a cationic surfactants.

In the compositions blended in hair treating agents of the present invention, nonionic surfactants are contained. As nonionic surfactants, polyoxyethylene alkyl or alkenyl ether or ethylene oxide (EO) adducts of fatty acid may be exemplified. Concretely, one or two kinds of compounds selected from the groups consisting of polyoxyethylene oleyl ether, polyoxyethylene cetyl ether, polyoxyethylene lauryl ether, polyoxyethylene stearyl ether and polyoxyethylene lanolin may be exemplified. As the above-mentioned polyoxyethylene ethers, e.g. 5 to 50 mole EO adducts may be exemplified.

Concretely, in the compositions blended in hair conditioners, hair colorings, waving agents and finishing agents, polyoxyethylene cetyl ether may be contained as a nonion surfactants.

Further, in the compositions blended in hair treating agents, fats and oils are contained. As the fats and oils, one to three compounds selected from the group consisting of lanolin, hard lanolin, hydrogenated oil (hydrogenated palm oil fatty acid triglyceride, hydrogenated tallow acid fatty acid triglyceride etc.), olive oil and mink oil may be exemplified as the concrete example.

Concretely, in the compositions blended in hair conditioners, lanolin may be contained, further in the compositions blended in hair colorings, waving agents and finishing agents, hydrogenated oil may be contained.

Further, in the compositions blended in hair treating agents of the present invention, any kind of additives may be contained in accordance with the kind of hair treating agents and the purpose.]

For example, in the compositions blended in hair treating agents, amphoteric surfactants may be contained as additives. As amphoteric surfactants, e.g. stearyl dimethyl glycine or lauryl dimethyl glycine may be exemplified.

Concretely, in the compositions blended in hair conditioners, for example, stearyl dimethyl glycine may be contained as an amphoteric surfactants.

Further, in the compositions blended in hair treating agents, hydrocarbons may be contained as additives. As the substantial example of hydrocarbons, one or two compounds selected from the group consisting of liquid petrolatum, vaseline and paraffine may be exemplified.

Still further, in the compositions blended in hair treating agents, fatty acids and/or sequestering agents may be contained as additives. As fatty acids, higher fatty acids such as stearic acid may be exemplified. And as sequestering agents, disodium edetate may be exemplified.

In the compositions blended in hair treating agents, polyoxypropylene butyl ether or methyl polysiloxane may be contained as additives. As the substantial example of the above-mentioned polyoxypropylene ether, e.g. 30 to 50 mole PO adducts may be exemplified.

Concretely, to the compositions blended in hair conditioners, polyoxypropylene butyl ether may be blended. Further, in the compositions blended in hair colorings, waving agents and finishing agents, methyl polysiloxane may be blended.

In formulations of the compositions blended in hair treating agents of the present invention, when the respective contents of esters, alcohols, cationic surfactants, nonionic surfactants, and fats and oils are U, V, W, X and Y (wt. %), it is desirable for U–Y to be within following ranges; $3 \leq U \leq 45$, $15 \leq V \leq 60$, $5 \leq W \leq 25$, $0.1 \leq X \leq 20$, $1 \leq Y \leq 20$, and $U+V+W+X+Y \leq 100$.

In a case of the compositions blended in hair conditioners, U, V, W, X and Y may be $5 \leq U \leq 40$, $15 \leq V \leq 55$, $5 \leq W \leq 25$, $1 \leq X \leq 20$, $1 \leq Y \leq 15$, and $U+V+W+X+Y \leq 100$.

In cases of the compositions blended in hair colorings, waving agents and finishing agents, U, V, W, X and Y may be $10 \leq U \leq 20$, $25 \leq V \leq 60$, $5 \leq W \leq 15$, $1 \leq X \leq 10$, $10 \leq Y \leq 20$, and $U+V+W+X+Y \leq 100$.

In the preparation method of the compositions blended in hair treating agents, for example, fatty esters, alcohols, cationic surfactants, nonionic surfactants, fats and oils and ingredients such as additives are mixed, heated and stirred until completely dissolved. The heating temperature is desirably lower than the decomposition temperatures of the mixture, for example, lower than 100° C., desirably lower than 85° C. The adding order of each ingredients are not limited.

The hair treating agents of the present invention contain the compositions blended in hair treating agents of the present invention. As the hair treating agents, hair conditioners, hair colorings, waving agents and finishing agents are illustrated below.

The hair conditioners of the present invention contain above-mentioned compositions blended in hair conditioners. As the compositions blended in hair conditioners, one or more kinds may be used.

Further, in the hair conditioners of the present invention, oiliness materials, preservatives, PPT (aqueous solutions of polypeptide), colors, perfumes and water may be contained as additives. As oiliness materials, for example, jojoba oil, avocado oil and mink oil may be exemplified. As preservatives, parabens such as methylparaben or propylparaben may be exemplified. As colors and perfumes, any kinds of colors and perfumes that are generally used to the hair conditioners may be used.

In formulations of the hair conditioners of the present invention, the contents of the compositions blended in hair conditioners are, for example, from 5 to 30 wt. %.

The preparing method of the hair conditioners of the present invention is not limited. For example, the compositions blended in hair conditioners which is heated and homogeneously dissolved is added to hot water with constant stirring and emulsified. After cooled down, additives may be added, if necessary. The heating temperature of water and the compositions blended in hair conditioners is lower than the decomposition temperatures of the mixture, for example, desirably lower than 95° C.

As hair colorings of the present invention, oxidizing hair coloring agents may be exemplified. The oxidizing hair coloring agents are composed of No. 1 agents and No. 2 agents (in the present invention, No. 1 agents alone and No. 2 agents alone are also comprised in the hair colorings of the present invention). No. 1 agents of the oxidizing hair coloring agents of the present invention may contain dye intermediates, alkaline agents, antioxidants, sequestering agents and/or water besides the compositions blended in hair colorings of the present invention. As dye intermediates, for example, phenylene diamines (e.g. ortho, meta, para phenylene diamine), phenols (e.g. ortho, meta, para aminophenol, nitrophenols) and aminocresols may be exemplified. As alkaline agents, ammonia solution and MEA (monoethanolamine) may be exemplified. As antioxidants, the compounds, that are used to the ordinary oxidizing hair coloring agents, such as sodium sulfite, ammonium thioglycolate, ascorbic acid and/or cysteine may be exemplified. As the sequestering agents, e.g. EDTA may be exemplified.

In formulations of No. 1 agents of oxidizing hair coloring agents, the contents of the compositions blended in hair colorings are, for example, from 10 to 35 wt. %, desirably from 20 to 30 wt. %. As the substantial method to prepare No. 1 agents of oxidizing hair coloring agents, following method may be exemplified. That is, for example, dye intermediates and antioxidants are poured into hot water and prepare homogeneous aqueous solution, then the compositions blended in hair colorings, which are heated and dissolved homogeneously, are added and mixed. After cooled down, additives such as alkaline agents or sequestering agents may be added to the mixture by constant stirring. The heating temperature of water and the compositions blended in hair colorings is lower than decomposition temperatures of the ingredients, for example, desirably lower than 95° C.

No. 2 agents of oxidizing hair coloring agents of the present invention may contain oxidizing agents, sequestering agents, pH adjustors and/or water may be contained besides the compositions blended in hair colorings of the present invention. As oxidizing agents, hydrogen peroxide may be exemplified. As sequestering agents, e.g. hydroxyethane diphosphoric acid may be exemplified. As pH adjustors, phosphoric acid salt (for example, dibasic sodium phosphate) may be exemplified.

In formulations of No. 2 agents of oxidizing hair coloring agents, the contents of the compositions blended in hair colorings are, for example, from 1 to 15 wt. %, desirably 2 to 10 wt. %.

As the substantial method to prepare No. 2 agents of oxidizing hair coloring agents, following method may be exemplified. That is, for example, the compositions blended in hair colorings of the present invention, which are heated and dissolved homogeneously, are added to hot water and dissolved homogeneously, stirred and emulsified. After cooled down, additives such as sequestering agents, pH adjustors and oxidizing agents may be added. The heating temperature of water and the compositions blended in hair colorings is lower than the decomposition temperatures of the ingredients, for example, desirably lower than 95° C.

The oxidizing hair coloring agents of the present invention contain at least one selected from the group consisting of No. 1 agents of oxidizing hair coloring agents and No. 2 agents of oxidizing hair coloring agents of the present invention. For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones, and the hair colorings consisting of No. 1 agents of oxidizing hair coloring agents except the above-mentioned ones and No. 2 agents of oxidizing hair coloring agents of the present invention are included. As "No. 1 agents of oxidizing hair coloring agents except the above-mentioned ones" and "No. 2 agents of oxidizing hair coloring agents except the above-mentioned ones", No. 1 agents and No. 2 agents which are generally used for the usual hair colorings may be exemplified.

As another hair colorings, decolorizing agents may be exemplified. The decolorizing agents are generally composed of No. 1 agents and No. 2 agents (in the present invention, No. 1 agents alone and No. 2 agents alone are also comprised in the hair colorings of the present invention). No. 1 agents of the decolorizing agents of the present invention may contain alkaline agents, sequestering agents and water besides the compositions blended in hair colorings of the present invention. As alkaline agents, e.g. ammonia and MEA may be exemplified. And as sequestering agents, EDTA may be exemplified.

In formulations of No. 1 agents of decolorizing agents, the desirable contents of the compositions blended in hair colorings are, for example, from 10 to 20 wt. %.

The preparing methods of No. 1 agents of decolorizing agents are illustrated as follows. For example, the compositions blended in hair conditioners that are heated and homogeneously dissolved is added to hot water with constant stirring and emulsified. After cooled down, additives such as alkaline agents or sequestering agents may be added. The heating temperature of water and the compositions blended in hair conditioners is lower than the decomposition temperatures of the mixture, for example, desirably lower than 95° C.

The ingredients and preparing method of No. 2 agents of the decolorizing agents of the present invention may be the same as the case of No. 2 agents of the oxidizing hair coloring agents of the present invention.

The decolorizing agents of the present invention contain at least one selected from the group consisting of No. 1 agents of decolorizing agents and No. 2 agents of decolorizing agents of the present invention. For example, in the decolorizing agents of the present invention, the hair colorings consisting of No. 1 agents of decolorizing agents of the present invention and No. 2 agents of decolorizing agents of the present invention, the hair colorings consisting of No. 1 agents of decolorizing agents of the present invention and No. 2 agents of decolorizing agents except the above-mentioned ones and the hair colorings consisting of No. 1 agents of decolorizing agents except the above-mentioned ones and No. 2 agents of decolorizing agents of the present invention are included.

As "No. 1 agents of decolorizing agents except the above-mentioned ones" and "No. 2 agents of decolorizing agents except the above-mentioned ones", the No. 1 and No. 2 agents that are ordinary used in the conventional decolorizing agents may be exemplified.

As another hair colorings of the present invention, acidic hair coloring materials may be exemplified. The acidic hair coloring materials may contain tar colors, organic solvents, organic and inorganic acids, sequestering agents and water besides the compositions blended in hair colorings. As organic solvents, benzyl alcohol and N-methl-2-pyrrolidone (NMP) may be exemplified. As organic acids, lactic acid, glycolic acid, tartaric acid and citric acid may be exemplified. As inorganic acids, phosphoric acid and hydrochloric acid may be exemplified. As sequestering agents, EDTA may be exemplified.

In formulations of the acidic hair coloring materials, the contents of the compositions blended in hair colorings are, for example, from 15 to 30 wt. %, desirably from 20 to 25 wt. %.

As the substantial method to prepare the acidic hair coloring materials, following method may be exemplified. That is, for example, the compositions blended in hair colorings of the present invention, which are heated and dissolved homogeneously, are added to hot water in which tar color is dissolved and stirred. After cooled down, organic solvents, organic acids and inorganic acids may be added. The heating temperature of water and the compositions blended in hair colorings is lower than the decomposition temperatures of the ingredients, for example, desirably lower than 95° C.

As waving agents of the present invention, the cationic waving agents may be exemplified. The cationic waving agents are generally composed of No. 1 agents and No. 2 agents (in the present invention, both No. 1 agents alone and No. 2 agents alone are also comprised in the hair colorings of the present invention). No. 1 agents of the cationic waving agents of the present invention may contain reducing agents, alkaline agents and water besides the compositions blended in waving agents of the present invention. As reducing agents, thioglycolic acid and cysteine or salts (ammonium salt, MEA salt etc.) of them may be exemplified. As alkaline agents, ammonia, amines (MEA, isopropanolamine etc.), ammonium salts (ammonium bicarbonate etc.) and basic amino acid may be exemplified.

In formulations of No. 1 agents of the cationic waving agents, the contents of the compositions blended in waving agents are, for example, from 10 to 25 wt. %, desirably 15 to 25 wt. %.

As the substantial method to prepare No. 1 agents of the cationic waving agents following method may be exemplified. That is, for example, the compositions blended in waving agents, which are heated and dissolved homogeneously, are added to hot water, stirred and emulsified. After cooled down, reducing agents and alkaline agents may be added. The heating temperature of water and the compositions blended in waving agents are lower than the decomposition temperatures of the ingredients, for example, desirably lower than 95° C.

In No. 2 agents of the cationic waving agents of the present invention, oxidizing agents, organic acids, cationic surfactants, inorganic acids, sequestering agents and/or water may be contained besides the compositions blended in waving agents of the present invention. As oxidizing agents, bromates and/or hydrogen peroxide may be exemplified. As organic acids, citric acid and/or tartaric acid may be exemplified. As cationic surfactants, lauryl trimethyl ammonium halide may be exemplified. As inorganic acids, phosphoric acid and/or dibasic sodium phosphate may be exemplified. Further, as sequestering agents, e.g. hydroxyethane diphosphoric acid may be exemplified.

In formulations of No. 2 agents of the cationic waving agents, the contents of the compositions blended in waving agents are, for example, from 10 to 25 wt. %.

As the substantial method to prepare No. 2 agents of the cationic waving agents of the present invention, following method may be exemplified. That is, for example, the compositions blended in waving agents, which are heated and dissolved homogeneously, are added to hot water, stirred and emulsified. After cooled down, oxidizing agents, organic acids, cationic surfactants, inorganic acids and sequestering agents may be added. The heating temperature of water and the compositions blended in waving agents are lower than the decomposition temperatures of the ingredients, for example, desirably lower than 95° C.

The cationic waving agents of the present invention contain at least one selected from the group consisting of No. 1 agents of cationic waving agents and No. 2 agents of cationic waving agents of the present invention. For example, the cationic waving agents of the present invention is one consisting of No. 1 agents of cationic waving agents of the present invention and No. 2 agents of cationic waving agents of the present invention, one consisting of No. 1 agents of cationic waving agents of the present invention and No. 2 agents of cationic waving agents except the above-mentioned ones and another one consisting of No. 1 agents of cationic waving agents except the above-mentioned ones and No. 2 agents of cationic waving agents of the present invention.

As No. 1 agents of waving agents except the above-mentioned ones and No. 2 agents of waving agents except the above-mentioned ones No. 2 agents, the No. 1 and No. 2 agents which are ordinary used in the conventional waving agents may be exemplified. Concretely, as No. 2 agents of waving agents except the above-mentioned ones No. 2 agents, the mixture prepared by dissolving oxidizing agents and cationic surfactants homogeneously in water may be exemplified.

As another waving agents of the present invention, the curling cream type waving agents may be exemplified. The curling cream type waving agents are also generally composed of No. 1 agents and No. 2 agents (in the present invention, both No. 1 agents alone and No. 2 agents alone are also comprised in the hair colorings of the present invention). No. 1 agents of the curling cream type waving agents of the present invention may contain reducing agents, alkaline agents and water besides the compositions blended in waving agents of the present invention. As reducing agents, sodium sulfite may be exemplified. As alkaline agents, e.g. MEA may be exemplified.

In formulations of No. 1 agents of the curling cream type waving agents, the contents of the compositions blended in waving agents are, for example, from 5 to 20 wt. %, desirably 6 to 15 wt. %.

As the substantial method to prepare No. 1 agents of the curling cream type waving agents following method may be exemplified. That is, for example, the compositions blended in waving agents, which are heated and dissolved homogeneously are added to hot water, stirred and emulsified. After cooled down, reducing agents and alkaline agents may be added. The heating temperature of water and the compositions blended in waving agents are lower than the decomposition temperatures of the ingredients, for example, desirably lower than 95° C.

The ingredients and preparing method of No. 2 agents of the curling cream type agents of the present invention may be the same as the case of No. 2 agents of the oxidizing hair coloring agents of the present invention.

The curling cream type waving agents of the present invention contain at least one selected from the group consisting of No. 1 agents of curling cream type waving agents and No. 2 agents of curling cream type waving agents of the present invention. For example, the curling cream type waving agents of the present invention is one consisting of No. 1 agents of curling cream type waving agents of the present invention and No. 2 agents of curling cream type waving agents of the present invention, one consisting of No. 1 agents of curling cream type waving agents of the present invention and No. 2 agents of curling cream type waving agents except the above-mentioned ones and another one consisting of No. 1 agents of curling cream type waving agents except the above-mentioned ones and No. 2 agents of curling cream type waving agents of the present invention.

As "No. 1 agents of curling cream type waving agents except the above-mentioned ones" and "No. 2 agents of curling cream type waving agents except the above-mentioned ones", the No. 1 and No. 2 agents that are ordinary used in the conventional waving agents may be exemplified. Concretely, as No. 2 agents of curling cream type waving agents except the above-mentioned ones No. 2 agents, the solution prepared by dissolving organic acids in water may be exemplified.

The finishing agents of the present invention contain the compositions blended in finishing agents, and generally further contain water. And, as additives, the compounds indicated in hair conditioners may be voluntarily added.

In formulations of the finishing agents of the present invention, the contents of the compositions blended in finishing agents are, for example, from 1 to 10 wt. %.

The preparation method of the finishing agents of the present invention may be the same as the preparation method of the hair conditioners.

EXAMPLE

Example of the First Embodiment

The first embodiment of the present invention is illustrated more concretely according to the Examples.
(Preparation of the Compositions Blended in Hair Treating Agents)

Examples 1–6

The amounts (kg) shown in Table 1 of the ingredients were poured into a vessel and mixed, and the mixture was heated to the temperature shown in Table 1, then stirred and dissolved completely. Thus, the compositions blended in hair treating agents (Examples 1–6) of the present invention were prepared.

Example 7

Polyoxyethylene oleyl ether [0.19 kg (30 EO)+4.85 kg (13 EO)], sorbitan monooleate, isopropyl linoleate, safflower oil, oleic acid, and liquid petrolatum were heated to the temperature shown in Table 1, and mixed with stirring to prepare homogeneous dissolved material. This dissolved material was added with stirring to 47.24 L. of water, that was heated to the temperature shown in Table 1, and emulsion was prepared. Then proper amount of ice was added to the emulsion, and cooled below 45° C.

On the other hand, polyoxyethylene oleyl ether [0.63 kg (30 EO)+0.33 kg (50 EO)] was heated to 80–90d° C. to prepare homogeneous dissolved material. This dissolved material was added with stirring to 4.53 kg of water that was heated to 80–90° C., and dissolved to prepare stabilizer. Then the stabilizer was cooled below 40° C.

To the above-mentioned cooled emulsion, the cooled stabilizer, sorbic acid, sodium hydroxide, phosphoric acid and water etc. were added with stirring to prepare 100 kg of the composition blended in a hair treating agent. The ingredients, contents (kg) and heating temperature are shown in Table 1.

Example 8

Emulsion was prepared under the condition shown in Table 2 by the same process as Example 7 except that polyoxyethylene oleyl ether [0.147 kg (30 EO)+3.59 kg (13 EO)] and 33.46 L. of water were used instead of polyoxyethylene oleyl ether [0.1 kg (30 EO)+4.85 kg (13 EO)] and 47.24 L. of water. Then the emulsion was cooled.

On the other hand, stabilizer was prepared under the condition shown in Table 2 by the same process as Example 7 except that polyoxyethylene oleyl ether [2.83 kg (30 EO)+1.43 kg (50 EO)] and 9.84 kg of water were used instead of polyoxyethylene oleyl ether [0.63 kg (30 EO)+0.33 kg (50 EO)] and 4.53 kg of water. Then the emulsion was cooled.

Then, by the same process as Example 7, 100 kg of the composition blended in a hair treating agent was prepared. The ingredients, contents (kg), and the heating temperature to prepare the emulsion are shown in Table 2.

Example 9

The emulsion was prepared under the condition shown in Table 2 by the same process as Example 7 except that avocado oil was further added. And then, the emulsion was cooled.

On the other hand, stabilizer was prepared under the condition shown in Table 2 by the same process as Example 7, and then cooled. Next, by the same process as Example 7, 100 kg of the composition blended in a hair treating agent was prepared. The ingredients, contents (kg), and the heating temperature to prepare the emulsion are shown in Table 2.

Example 10

Emulsion was prepared under the condition shown in Table 2 by the same process as Example 7 except that polyoxyethylene (30 EO) oleyl ether was not used, and polyoxyethylene (13 EO) oleyl ether [5.04 kg] and 47.54 L. water were used instead of polyoxyethylene(13 EO) oleyl ether [4.85 kg (13 EO)] and 47.24 L. of water, and wheat germ oil was further added. Then the emulsion was cooled.

On the other hand, stabilizer was prepared under the condition shown in Table 2 by the same process as Example 7 except that polyoxyethylene oleyl ether [0.64 kg (30 EO)+0.32 kg (50 EO)] and 4.92 kg of water were used instead of polyoxyethylene oleyl ether [0.63 kg (30 EO)+0.33 kg (50 EO)] and 4.53 kg of water. Then the stabilizer was cooled.

Next, 100 kg of the composition blended in a hair treating agent was prepared by the same process as Example 7. The ingredients, contents (kg), and the heating temperature to prepare the emulsion are shown in Table 2.

Example 11

Each of all ingredients shown in Table 2 except sorbic acid, phosphoric acid, sodium hydroxide, and water were mixed and heated to the temperature shown in Table 2, and dissolved homogeneously. This dissolved material was added with stirring to water that was heated to the temperature shown in Table 2 to prepare emulsion.

Then proper amount of ice was added to the emulsion. After the emulsion was cooled below 45° C., sorbic acid, sodium hydroxide, phosphoric acid and water were added to the emulsion and stirred homogeneously to prepare 100 kg of the composition blended in a hair treating agents. The ingredients, contents (kg) and the heating temperature to prepare the emulsion are shown in Table 2.

Example 12

Emulsion was prepared under the condition shown in Table 2 by the same process as Example 7 except that polyoxyethylene (30 EO) oleyl ether was not used. Then the emulsion was cooled.

On the other hand, stabilizer was prepared under the condition shown in Table 2 by the same process as Example 7 except that polyoxyethylene lanolin and 6.89 kg of water was used instead of polyoxyethylene oleyl ether and 4.53 kg of water. Then the stabilizer was cooled.

To the aforementioned cooled emulsion, the above-mentioned cooled stabilizer, sorbic acid, sodium hydroxide, phosphoric acid and water etc. were added with stirring to prepare the emulsified 100 kg of the composition blended in a hair treating agents. The ingredients, contents (kg) and the heating temperature to prepare the emulsion are shown in Table 2.

Example 13

0.315 kg of polyoxyethylene (13 EO) oleyl ether was heated to 45–50° C. 0.39 kg of perfumes[trade name, "BOIS DE ROSE" (Meiji-Koryo co.)] was added to this and dispersed homogeneously. Then, 4.08 kg of water was added with stirring homogeneously to prepare an agents for solbilizing perfumes.

After the above agents cooled below 27° C., the cooled agents was added with stirring to 94.75 kg of the composition blended in a hair treating agents prepared in Example 9 (which had been cooled below 27° C.). Thus, 100 kg of the composition blended in a hair treating agents was prepared. The ingredients, contents (kg), and the heating temperature are shown in Table 2.

Example 14

The amounts (kg) shown in Table 2 of the ingredients were poured into a vessel and mixed, and the mixture was heated to the temperature shown in Table 2, then stirred and dissolved completely. Thus, the compositions blended in a hair treating agents of the present invention were prepared.

TABLE 1

| | Example | | | | | | |
|---|---|---|---|---|---|---|---|
| | 1 | 2 | 3 | 4 | 5 | 6 | 7 |
| | heating temp (° C.) | | | | | | |
| Ingredient (kg) | 80 | 60~70 | 80 | 80 | 70 | 80 | 91~93 |
| propylene glycol dicaprate | 75 | — | — | — | — | — | — |
| polyethylene glycol distearate | — | — | — | — | — | 4 | — |
| caprylic capric acid triglyceride | 12.5 | — | 33 | — | — | — | — |
| triglyceryl cocoate | — | — | — | 30 | — | — | — |
| dipentaerythritol fatty acid ester[1] | — | — | — | 50 | — | — | — |
| isopropyl palmitate | — | — | — | 10 | — | — | — |
| 2-hexyldecyl isostearate | — | — | — | — | 10 | — | — |
| isopropyl linoleate | — | — | — | — | — | — | 2 |
| diisostearyl malate | — | — | — | — | — | — | — |
| diisopropyl adipate | — | 25 | — | — | — | — | — |
| diisobutyl adipate | — | 25 | — | 10 | — | — | — |
| lanolin fatty acid octyldodecyl ester | — | — | 34 | — | — | — | — |
| polyoxyethylene lauryl ether[2] | — | — | — | — | — | 4 | — |
| polyoxyethylene oleyl ether | — | — | — | — | — | — | 6 |
| polyoxyethylene lanolin | — | — | — | — | — | — | — |
| polyoxyethylene hydrogenated castor oil[3] | — | — | — | — | — | — | — |
| cocodimethyl amine oxide | — | — | — | — | — | 20 | — |
| sorbitan monooleate | — | — | — | — | — | — | 3 |
| sorbitan sesquioleate | — | — | — | — | — | — | — |
| sorbitan trioleate | — | — | — | — | — | — | — |
| polyoxyethylene coconut fatty acid monoethanolamide sodium sulfate[4] | — | — | — | — | — | 40 | — |
| soybean phospholipid | — | — | — | — | — | — | — |
| rice germ oil | — | — | — | — | 45 | — | — |
| wheat germ oil | — | — | — | — | — | — | — |
| shea butter | — | — | 33 | — | 45 | — | — |
| avocado oil | — | — | — | — | — | — | — |
| safflower oil | — | — | — | — | — | — | 8 |
| castor oil | — | — | — | — | — | — | — |
| meadowfoam oil | — | — | — | — | — | — | — |
| lactic acid[8] | — | — | — | — | — | 1 | — |
| sorbic acid[9] | — | — | — | — | — | — | 0.26 |
| oleic acid | — | — | — | — | — | — | 5 |
| phosphoric acid[9] | — | — | — | — | — | — | 0.04 |
| sodium hydroxide | — | — | — | — | — | — | 0.11 |
| liquid petrolatum | — | — | — | — | — | — | 20 |
| dimethylsiloxane · methylstearoxysiloxane copolymer | — | 50 | — | — | — | — | — |
| decamethyl cyclopentasiloxane | — | — | — | — | — | — | — |
| methyl parahydroxybenzoate | — | — | — | — | — | 0.1 | — |
| polyoxypropylene butyl ether[5] | 12.5 | — | — | — | — | — | — |
| dibutylhydroxytoluene | — | — | — | — | — | — | — |
| perfume | — | — | — | — | — | — | — |
| water | — | — | — | — | — | 30.9 | 55.59 |

TABLE 2

| Ingredient (kg) | Example 8 | 9 | 10 | 11 | 12 | 13 | 14 |
|---|---|---|---|---|---|---|---|
| heating temp (° C.) | 90~92 | 87~89 | 84~86 | 94~98 | 85~87 | 45~50 | 40~50 |
| propylene glycol dicaprate | — | — | — | — | — | — | — |
| polyethylene glycol distearate | — | — | — | — | — | — | — |
| caprylic capric acid triglyceride | — | — | — | — | — | — | — |
| triglyceryl cocoate | — | — | — | — | — | — | — |
| dipentaerythritol fatty acid ester[1] | — | — | — | 1.5 | — | — | — |
| isopropyl palmitate | — | — | — | — | — | — | — |
| 2-hexyldecyl isostearate | — | — | — | — | — | — | — |
| isopropyl linoleate | 1 | 2 | 2 | — | 2 | 2 | — |
| diisostearyl malate | — | — | — | — | — | — | 3 |
| diisopropyl adipate | — | — | — | — | — | — | — |
| diisobutyl adipate | — | — | — | — | — | — | — |
| lanolin fatty acid octyldodecyl ester | — | — | — | — | — | — | — |
| polyoxyethylene lauryl ether[2] | — | — | — | — | — | — | — |
| polyoxyethylene oleyl ether | 8 | 6 | 6 | 7.5[7] | 5 | 6 | — |
| polyoxyethylene lanolin | — | — | — | — | 3.5[6] | — | — |
| polyoxyethylene hydrogenated castor oil[3] | — | — | — | — | — | — | 10 |
| cocodimethyl amine oxide | — | — | — | — | — | — | — |
| sorbitan monooleate | 2 | 3 | 3 | — | 3 | 3 | — |
| sorbitan sesquioleate | — | — | — | 2.5 | — | — | — |
| sorbitan trioleate | — | — | — | 2 | — | — | — |
| polyoxyethylene coconut fatty acid monoethanolamide sodium sulfate4) | — | — | — | — | — | — | — |
| soybean phospholipid | — | — | — | — | 0.1 | — | — |
| rice germ oil | — | — | — | — | — | — | — |
| wheat germ oil | — | — | 1 | — | — | — | — |
| shea butter | — | — | — | — | — | — | — |
| avocado oil | — | 4 | — | — | — | 4 | — |
| safflower oil | 5 | 4 | 7 | — | 8 | 4 | 5 |
| castor oil | — | — | — | — | — | — | 78.95 |
| meadowfoam oil | — | — | — | 8 | — | — | — |
| lactic acid[8] | — | — | — | — | — | — | — |
| sorbic acid[9] | 0.17 | 0.26 | 0.26 | 0.26 | 0.26 | 0.26 | — |
| oleic acid | 0.35 | 0.5 | 0.5 | 0.5 | 0.5 | — | — |
| phosphoric acid[9] | 0.03 | 0.04 | 0.04 | 0.8 | 0.04 | 0.04 | — |
| sodium hydroxide | 0.07 | 0.11 | 0.11 | 0.1 | 0.11 | 0.11 | — |
| liquid petrolatum | 13 | 20 | 20 | 14.5 | 20 | 20 | — |
| dimethylsiloxane · methylstearoxysiloxane copolymer | — | — | — | — | — | — | — |
| decamethyl cyclopentasiloxane | — | — | — | — | — | — | 3 |
| methyl parahydroxybenzoate | — | — | — | — | — | — | — |
| polyoxypropylene butyl ether[5] | — | — | — | — | — | — | — |
| dibutylhydroxytoluene | — | — | — | — | — | — | 0.05 |
| perfume | — | — | — | — | — | 0.39 | — |
| water | 70.38 | 60.09 | 60.09 | 62.34 | 57.49 | 60.2 | — |

1)–9) in Tables 1 and 2 indicating,
1) the full esters prepared from dipentaerythritol and mixed acid (12-hydroxystearic acid:stearic acid:rosin=4:15:0.5),
2) 5 EO,
3) 10 EO,
4) 3 EO,
5) 52 PO,
6) 70 EO, containing 1.5 wt. % of lecithin,
7) 2.5kg (5 EO)+4 kg(13 EO)+1 kg(30 EO),
8) containing 10 wt. % of water,
9) containing 15 wt. % of water.

(Preparation of Hair Conditioners)

Examples 15–19

Initial purified water was heated to the temperature of 80–85° C. On the other hand, the composition blended in a hair conditioner obtained above (Examples 1–5), additive composition, and parabens were mixed and heated to the temperature of 80–85° C., and then dissolved homogeneously.

The homogeneous dissolved material was added to the above-mentioned hot water with constant stirring and emulsified. Then the emulsion was cooled down to the temperature of 48° C. with constant stirring. Next, perfume was added, and finally purified water (add water) was added so as to adjust the total weight to be 100 kg and then mixed homogeneously. Thus, the hair conditioners of the present invention (Examples 15–19) were prepared. The ingredients and contents (kg) are shown in Table 3.

TABLE 3

| ingredient (kg) | Example 15 | 16 | 17 | 18 | 19 |
|---|---|---|---|---|---|
| composition blended in hair conditioner | Example 1 1 | Example 2 1 | Example 3 1 | Example 4 1 | Example 5 1 |

TABLE 3-continued

| ingredient (kg) | Example | | | | |
|---|---|---|---|---|---|
| | 15 | 16 | 17 | 18 | 19 |
| additive composition[1)] | 12 | 12 | 12 | 12 | 12 |
| parabens | 0.15 | 0.15 | 0.15 | 0.15 | 0.15 |
| purfume | proper amount | proper amount | proper amount | proper amount | proper amount |
| initial water | 70 | 70 | 70 | 70 | 70 |

1) in Tables 3 are indicating,
1) ingredients (wt. %); stearyl alcohol(45), mixture of monoglyceryl and diglyceryl prepared from mixed acid of oleic acid and stearic acid (8), butyl stearate (5), mink oil (5), dipropylene glycol (5), polyoxyethylene (23 EO) lauryl ether (2), lanolin amidopropyl ethyl dimethyl ammonium ethylsulfate (5), 60 wt. % stearyl trimethyl ammonium chloride (25).

(Preparation of Permanent Waving Agents)

Examples 20–25

Preparation of No. 1 Agents

To initial water, 50 wt. % ammonium thioglycolate (ATG) aqueous solution, strong ammonia solution and the composition blended in a waving agent (Example 7, 9–13) were added in order. Further, purified water (add water) was added so as to adjust the total weight to be 100 kg. Thus No. 1 agent was prepared(Example 20–25). Following way performed the above addition in order. Namely, after it was confirmed that the previous ingredients was mixed homogeneously, following ingredients was added. Ingredients and contents (kg) are shown in Table 4.

Preparation of No. 2 Agents

To initial water, sodium bromate and the composition blended in a waving agent (Example 8) were added in order. Further, purified water (add water) was added so as to adjust the total weight to be 100 kg. Thus No. 2 agent was prepared. Following way performed the above in order addition. Namely, after it was confirmed that the previous ingredients was mixed homogeneously, following ingredients was added. Ingredients and contents (kg) are shown in Table 4.

(Preparation of Finishing Agents)

Example 26

1 kg of the composition blended in a finishing agent (Example 11) was added to 99 kg of water with stirring at room temperature, and then mixed homogeneously to prepare a finishing agent.

(Preparation of Permanent Waving Iron Sliding Improvers)

Example 27

About 99 kg of the composition blended in a permanent waving iron sliding improver (Example 14), proper amount of perfume, and proper amount of pigment aqueous solution were mixed homogeneously at room temperature, to prepare 100 kg of the permanent waving iron sliding improver.

(The Organoleptic Tests About Hair Treating Effects of the Hair Treating Agents)

Hair treatings were carried out to 50 monitors by the following methods. And the results of the organoleptic tests about hair treating effects (i. e. feel when used) of the hair treating agents were obtained. The results of organoleptic tests were summarized in Table 5.

The Method for Hair Treating with Hair Conditioners

After ordinary shampoo, a specimen of each hair conditioners (Examples 15–19) was applied to hair and spread by combing, and then rinsed and dried using a dryer.

The Method for Hair Treating with Waving Agents

No. 1 agent of the waving agents (Example 20–25) was coated to hair and spread by combing, and the hair was wound to a rod and heated for 7 minutes at 45° C. Then No. 2 agents was coated by an applicator and left for 7 minutes. After the rod was removed, the hair was rinsed and dried using a dryer.

The Method for Hair Treating with Finishing Agents

The finishing agent (Example 2–6) was sprayed and coated to hair with pumpsprayer.

The Method for Hair Treating with Permanent Waving Iron Sliding Improvers

The permanent waving iron sliding improver (Example 27) was coated to hair, and then finished to predetermined hair style with iron.

TABLE 4

| ingredient (kg) | Example | | | | | |
|---|---|---|---|---|---|---|
| | 20 | 21 | 22 | 23 | 24 | 25 |
| No. 1 agent | | | | | | |
| composition blended in waving agent | Example 7 3 | Example 9 3 | Example 10 3 | Example 11 3 | Example 12 3 | Example 13 3 |
| 50% ATG | 13 | 13 | 13 | 13 | 13 | 13 |
| strong ammonia solution | proper amount | proper amount | proper amount | proper amount | proper amount | proper amount |
| initial water | about 65 | about 65 | about 65 | about 65 | about 65 | about 65 |
| No. 2 agent | | | | | | |
| composition blended in waving agent | Example 8 5 | Example 8 5 | Example 8 5 | Example 8 5 | Example 8 5 | Example 8 5 |
| sodium bromate | 8 | 8 | 8 | 8 | 8 | 8 |
| initial water | about 65 | about 65 | about 65 | about 65 | about 65 | about 65 |

TABLE 5

| feel when used and function of hair treatig agent | hair treating agent (Example) | | | | | | | | | | | | |
|---|---|---|---|---|---|---|---|---|---|---|---|---|---|
| | 15 | 16 | 17 | 18 | 19 | 20 | 21 | 22 | 23 | 24 | 25 | 26 | 27 |
| moist feel | ◎ | ○ | ◎ | ◎ | ◎ | ○ | ○ | ○ | ○ | ○ | ○ | ○ | — |
| slippery feel | ◎ | Δ | Δ | Δ | Δ | Δ | Δ | Δ | Δ | Δ | Δ | Δ | — |
| wet feel | ◎ | Δ | ○ | ○ | ○ | Δ | Δ | Δ | Δ | Δ | Δ | ○ | — |
| smooth feel | ◎ | ◎ | Δ | Δ | ◎ | Δ | Δ | Δ | Δ | Δ | Δ | Δ | ◎ |
| soft feel | Δ | ◎ | ◎ | ○ | ◎ | ○ | ◎ | ◎ | ◎ | ◎ | ○ | ○ | — |
| slightly oily feel | ○ | ○ | ◎ | Δ | ○ | ◎ | ◎ | ◎ | ◎ | ○ | ○ | ◎ | ◎ |
| rustle feeling | Δ | ○ | Δ | ◎ | Δ | ○ | ○ | ○ | ○ | ○ | ○ | Δ | — |
| adsorptiveness | Δ | Δ | ○ | ○ | ◎ | Δ | Δ | Δ | ○ | Δ | Δ | Δ | — |
| luster | Δ | ○ | Δ | Δ | ○ | Δ | Δ | Δ | Δ | Δ | Δ | ◎ | — |
| prevention of hair damage | — | — | — | — | — | ◎ | ◎ | ◎ | ◎ | ◎ | ◎ | — | ○ |
| smooth wave formation | — | — | — | — | — | ◎ | ◎ | ◎ | ◎ | ◎ | ◎ | — | ○ |
| firmly rooted wave | — | — | — | — | — | ◎ | ◎ | ◎ | ◎ | ◎ | ◎ | — | ○ |
| no unevenness of waving finish | — | — | — | — | — | ◎ | ◎ | ◎ | ◎ | ◎ | ◎ | — | Δ |
| pleasant touch after waving | — | — | — | — | — | ◎ | ◎ | ○ | ○ | ◎ | ◎ | — | ◎ |
| less mercapto odor | — | — | — | — | — | Δ | Δ | Δ | Δ | Δ | ◎ | — | — |

In Table 5, ◎ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as moist feel, slippery feel, wet feel, smooth feel, soft feel, slightly oily feel, rustle feeling, luster, smooth completion of wave formation, no unevenness of wave, prevention of hair damage etc. Further, in the preparation process of hair treating agent since it is possible by using the compositions blended in a hair treating agents of the present invention to blend plural ingredients at a time, the production process may be remarkably simplified.

Example of the Second Embodiment

The second embodiment of the present invention is illustrated more concretely according to the Examples.

(Preparation of the Compositions Blended in Hair Treating Agents)

Examples 28–34

The amounts (kg) shown in Table 6 of ingredients were poured into a vessel and mixed, and the mixture was heated to the temperature shown in Table 6, then stirred and dissolved completely. Thus, the compositions blended in a hair treating agents (Examples 28–34) of the present invention were prepared.

TABLE 6

| | Example | | | | | | |
|---|---|---|---|---|---|---|---|
| | 28 | 29 | 30 | 31 | 32 | 33 | 34 |
| ingredient (kg) | | | | heating temp (° C.) | | | |
| | 80 | 80 | 85 | 70~75 | 90 | 55~60 | 75 |
| mono and diglyceryl oleate and stearate | — | 10 | — | — | — | — | — |
| lipophilic glyceryl monostearate | 5 | — | — | — | 22 | 19 | — |
| lipophilic glyceryl monooleate | — | — | — | — | — | — | 3.6 |
| isopropyl myristate | — | — | — | — | — | — | 10.8 |
| octyl palmitate | 10 | — | — | — | — | — | — |
| cetyl palmitate | — | — | 29 | 15 | — | — | — |
| 2-hexyldecyl isostearate | — | 16 | — | — | — | — | — |
| myristyl alcohol | — | — | — | — | — | 28 | — |
| cetanol | — | — | — | 64 | 16 | — | 56.6 |
| octyldodecanol | — | — | — | — | — | — | 0.9 |
| behenyl alcohol | 60 | 56 | 57 | — | — | — | — |
| ethanol | — | — | — | 2 | — | — | — |
| dipropylene glycol | — | — | — | — | — | — | 3.5 |
| hydrogenated oil | 2 | — | — | — | — | — | — |
| persic oil | 1 | — | — | — | — | — | — |
| lanolin | — | — | — | 2 | — | — | — |
| olive oil | — | — | — | — | — | 10 | — |
| sodium cetyl sulfate | — | — | — | 9 | — | — | — |
| sodium N-myristoyl N-methyl tau | — | — | — | — | — | — | 10.8 |
| myristic acid | 2 | — | — | — | — | — | — |
| stearic acid | — | — | — | — | 24 | 19 | — |
| lanolin fatty acid | — | — | — | — | — | — | 3.5 |
| paraffin | — | — | — | — | — | — | 3.5 |
| beeswax | — | — | — | 0.5 | — | — | — |
| candelilla wax | — | — | — | — | 38 | 24 | — |
| stearamidoethyl diethylamine | — | — | 14 | — | — | — | — |
| stearamidopropyl dimethylamine | 20 | 18 | — | — | — | — | — |
| methylphenyl polysiloxane | — | — | — | 0.1 | — | — | — |
| water | — | — | — | 7.4 | — | — | 6.8 |

(Preparation of Hair Conditioners)

Examples 35–37

To initial water, additives such as lactic acid, preservatives, and sodium cetyl sulfate etc. were, if necessarily, added and heated to the temperature shown in Table 7. On the other hand, the composition blended in hair conditioner obtained above (Examples 28, 30, or 31), additives such as behenyl alcohol, phenoxyethanol, additive composition, and preservative were, if necessarily, mixed and heated to the temperature shown in Table 7, and then dissolved homogeneously.

The homogeneous dissolved material was added to the above-mentioned hot water (or hot aqueous solution) with constant stirring and emulsified. Then the emulsion was cooled down to the temperature shown in Table 7 with constant stirring. Next, perfume and, if necessarily, dl-malic acid were added, then purified water (add water) was added so as to adjust the total weight to be 100 kg, and mixed homogeneously. Thus, the hair conditioners of the present invention (Examples 35–37) were prepared. The ingredients and contents (kg) are shown in Table 7.

TABLE 7

|  | Example | | |
| --- | --- | --- | --- |
|  | 35 | 36 | 37 |
|  | heating temp (° C.) | | |
|  | 80~85 | 85~88 | 87~89 |
|  | cooling temp (° C.) | | |
| ingredient (kg) | 50 | 50 | 65 |
| composition blended in hair conditioner | Example 28 9 | Example 30 12 | Example 31 5 |
| preservative | 0.1[1] | — | 0.15[3] |
| lactic acid | 0.6 | 0.65 | — |
| dl-malic acid | — | — | 0.2 |
| additive composition | — | 1[2] | — |
| behenyl alcohol | — | 6 | — |
| phenoxyethanol | — | 0.4 | — |
| sodium cetyl sulfate | — | — | 0.6 |
| perfume | proper amount | proper amount | proper amount |
| initial water | 80 | 80 | 80 |

1)–3) in Tables 7 are indicating,
1) trade name "CAE" (Ajinomoto co.),
2) ingredients(wt. %); dipentaerythritol fatty ester[full esters prepared from dipentaerythritol and mixed acid (wt. % ratio of 12hydroxystearic acid:stearic acid:rosin= 4:1.5:0.5)] (50), coconut oil (30), isopropyl palmitate (10), diisobutyl adipate (10),
3) Parpbens.

(Preparation of Oxidizing Hair Coloring Agents)

Example 38

Preparation of No. 1 Agents

To 50 kg of initial purified water that was heated to the temperature of 80–85° C., 0.5 kg of anhydrous sodium sulfite, 3.0 kg of propylene glycol and a proper amount of dye intermediates (resorcinol, phenylene diamine, m-aminophenol, p-aminophenol) were added and mixed homogeneously. To the obtained mixture, 20 kg of the composition blended in hair coloring (Example 34) that was dissolved homogeneously at the temperature of 80–85° C. was added, stirred and emulsified. Then the emulsion was cooled down to the temperature of 50–55° C. with constant stirring, 8 kg of hydrochloric acid-MEA solution, 0.2 kg of EDTA and a proper amount of MEA were added. And further purified water (add water) was added so as to adjust the total weight to be 100 kg. Thus No. 1 agent was prepared.

Preparation of No. 2 Agents 60 kg of initial purified water and 0.1 kg of EDTA were mixed and heated to the temperature of 80–85° C. On the other hand, 15 kg of the composition blended in hair coloring (Example 34), and 0.1 kg of phenacetium were mixed and heated to the temperature of 80–85° C., and then dissolved homogeneously. Then, the homogeneous dissolved material was added to the above-mentioned hot aqueous solution with constant stirring and emulsified.

After the emulsion was cooled down to the temperature of 65° C. with constant stirring, 17 kg of 35 wt. % hydrogen peroxide was added. Further, after cooled down to the temperature of 45° C. with constant stirring, 0.25 kg of 85 wt. % phosphoric acid, 0.9 kg of dibasic sodium phosphate (12 hydrate) were added. And finally purified water (add water) was added so as to adjust the total weight to be 100 kg. Thus No. 2 agent was prepared.

(Preparation of Acidic Hair Coloring Materials)

Example 39

25 kg of the composition blended in hair coloring (Example 34) was heated to 80–85° C. and homogeneously dissolved. On the other hand, proper amount of initial purified water, 0.3 kg of black No. 401, 0.3 kg of violet No. 401, and 0.6 kg of orange No. 205 were mixed to prepare aqueous solution. Then, the aforementioned homogeneous dissolved material was added to the above-mentioned the aqueous solution with constant stirring and emulsified. After the emulsion was cooled down to the temperature of 45° C., 3 kg of benzyl alcohol, 5 kg of N-methl-2-pyrrolidone (NMP) were added, further, purified water (add water) was added so as to adjust the total weight to be 100 kg. Thus the acidic hair coloring material was prepared.

(Preparation of Decolorizing Agents)

Example 40

Preparation of No. 1 Agents

To 70 kg of initial purified water that was heated to the temperature of 80–85° C., 15 kg of the oiliness composition[1], that was heated to the temperature of 80–85° C. and dissolved homogeneously, was added, stirred and emulsified. After cooled down, 6.6 kg of MEA and 0.1 kg of disodium edetate were added. And further purified water (add water) was added so as to adjust the total weight to be 100 kg. Thus No. 1 agent was prepared.
1) ingredients (wt. %); oleyl alcohol (4), stearyl alcohol (41), lauryl alcohol (1), paraffin (5), dipropylene glycol (7), isopropyl myristate (11), hard lanolin, (7), hydrogenated oil (4), polyoxyethylene cetyl ether, (5), polyoxyethylene (25 EO) lauryl ether (2), octyldodecanol, (1), 70 wt. % cetyl trimethyl ammonium chloride (11), 60 wt. % stearyl trimethyl ammonium chroride (1).

Preparation of No. 2 Agent 60 kg of initial purified water and 0.1 kg of EDTA were mixed and heated to the temperature of 80–85° C. to prepare aqueous solution. On the other hand, 15 kg of the composition blended in hair coloring (Example 34), and 0.1 kg of phenacetium were mixed and heated to the temperature of 80–85° C., and then dissolved homogeneously. Then, the homogeneous dissolved material was added to the above-mentioned hot aqueous solution with constant stirring and emulsified.

After the emulsion was cooled down to the temperature of 65° C. with constant stirring, 17 kg of 35 wt. % hydrogen peroxide was added and mixed homogeneously. Further, after the homogeneous mixture was cooled down to the temperature of 45° C. with constant stirring, 0.25 kg of 85 wt. % phosphoric acid, 0.9 kg of dibasic sodium phosphate (12 hydrate) and finally, purified water (add water) was added so as to adjust the total weight to be 100 kg. Thus No. 2 agent was prepared.

(Preparation of Waving Agents)

Example 41
Preparation of No. 1 Agents 15 kg of the composition blended in waving agent (Example 34) was heated to the temperature of 80–85° C. and homogeneously dissolved. And this was added to 50 kg of initial purified water that was previously heated to 80–85° C., stirred and emulsified. Then the emulsion was cooled down to the temperature of 45° C., 13 kg of 50% ammonium thioglycolate, proper amount of strong ammonia solution and proper amount of ammonium bicarbonate were added to the emulsion Further, purified water (add water) was added so as to adjust the total weight to be 100 kg. Thus No. 1 agent was prepared.

Preparation of No. 2 Agent 15 kg of the composition blended in waving agent (Example 34) was heated to the temperature of 80–85° C. and homogeneously dissolved, and this was added to 50 kg of initial purified water, that was heated to the temperature of 80–85° C., and emulsified. Then the emulsion was cooled down to the temperature of 45° C., 8 kg of sodium bromate was added to the emulsion, further, purified water (add water) was added so as to adjust the total weight to be 100 kg. Thus No. 2 agent was prepared.

(Preparation of Cream Type Waving Agents)

Example 42
Preparation of No. 1 Agent

No. 1 agent was prepared by the same process as Example 41.

Preparation of No. 2 Agent 15 kg of composition blended in waving agent (Example 34), and 0.1 kg of phenacetium were mixed and heated to the temperature of 80–85° C. On the other hand, 60 kg of initial purified water and 0.1 kg of EDTA were mixed and heated to the temperature of 80–85° C. to prepare aqueous solution.

Then, the aforementioned homogeneous dissolved material was added to the above-mentioned hot aqueous solution with constant stirring and emulsified. After the emulsion was cooled down to the temperature of 65° C. with constant stirring, 5.7 kg of 35 wt. % hydrogen peroxide aqueous solution was added. Further, after the homogeneous mixture was cooled down to the temperature of 45° C. with constant stirring, 0.05 kg of 85 wt. % phosphoric acid and finally, purified water (add water) was added so as to adjust the total weight to be 100 kg. Thus No. 2 agent was prepared.

(Preparation of the Finishing Agents)

Example 43

40 kg of initial purified water, 0.1 kg of TEA, and 6 kg of kaolin were mixed and heated to the temperature of 80–85° C. to prepare aqueous solution. On the other hand, 18.5 kg of the composition blended in finishing agent (Example 32), and 9 kg of squalane were mixed and heated to the temperature of 80–85° C., After this mixture was dissolved homogeneously, 3 kg of methyl polysiloxane (100 cs) and 18 kg of 1,3-butylene glycol were added and dispersed homogeneously.

Then, the above-mentioned hot aqueous solution was added to the homogeneous dispersion with constant stirring and emulsified. After the emulsion was cooled down to the temperature of 45° C. with stirring, purified water (add water) was added so as to adjust the total weight to be 100 kg. Thus the finishing agent of the present invention was prepared.

Examples 44–46

Ingredients A shown in table 8 were heated to the temperature of 80–85° C. and dissolved homogeneously. Similarly, ingredients B shown in table 8 were heated to the temperature of 80–85° C. and dissolved homogeneously. Then, the heated ingredients A was added to the heated ingredients B with constant stirring and emulsified.

After the emulsion was cooled down to the temperature of 45° C. with stirring, the homogeneously mixed ingredients C was added to the emulsion. Further, after cooled down to the temperature of 40° C., the ingredients D was added. Thus, the finishing agent of the present invention (Examples 44–46) was prepared. The heating temperature, ingredients, contents (kg) are shown in Table 8.

TABLE 8

| | | Example | | |
|---|---|---|---|---|
| | | 44 | 45 | 46 |
| | | heating temp (° C.) | | |
| ingredient (kg) | | 80~85 | 80~85 | 80~85 |
| A | composition blended in finishing agent | Example 33 7 | Example 33 7 | Example 33 7 |
| | isocetyl isostearate | 2.5 | 2.5 | 2.5 |
| | isononyl isononanoate | 0.2 | — | — |
| | isopropyl myristate | — | 0.5 | — |
| | (adipic acid · 2-ethylhexanic acid · stearic acid) glyceril oligoester | — | — | 0.5 |
| | parabens | 0.15 | 0.15 | 0.15 |
| B | sodium cocoyl ethyl ester sulfonate | 0.3 | 0.3 | 0.3 |
| | purified water | 70 | 70 | 70 |
| | 2% xanthan gum aqueous solution | 5 | 5 | 5 |
| | 50% 2-amino-2-methyl1propanol aqueous solution | 0.35 | 0.35 | 0.35 |
| C | 3-methyl-1,3-butandiol | 2.5 | 2.5 | 2.5 |
| | glycerin | 2.5 | 2.5 | 2.5 |
| | purified water | remaining volume | remaining volume | remaining volume |

TABLE 8-continued

|  | | Example | | |
|---|---|---|---|---|
|  | | 44 | 45 | 46 |
|  | | | heating temp (° C.) | |
| ingredient (kg) | | 80~85 | 80~85 | 80~85 |
| D | 50% lactic acid aqueous solution | proper amount | proper amount | proper amount |
| total weight | | 100 | 100 | 100 |

Example 47

60 kg of initial purified water, 0.3 kg of TEA, and 0.3 kg of sodium tetradecen sulfonate were mixed and heated to the temperature of 80–85° C. to prepare aqueous solution. On the other hand, 14 kg of the composition blended in finishing (Example 33), 1 kg of behenyl alcohol, 5 kg of castor oil, 1 kg of methyl polysiloxane (5 cs) and 0.4 kg of parabens were mixed and heated to the temperature of 80–85° C. and dissolved homogeneously. Then, to this, 10 kg of pearl pigments was added and dispersed homogeneously.

Then, the above-mentioned hot aqueous solution was added to the homogeneous dispersion with constant stirring and emulsified. After the emulsion was cooled down to the temperature of 45° C. with stirring, 5 kg of concentrated glycerin, 5 kg of 1,3-butylene glycol were added, And further, purified water (add water) was added so as to adjust the total weight to be 100 kg. Thus the finishing agent of the present invention was prepared.

(The Organoleptic Tests About Hair Treating Effects of the Hair Treating Agents)

Hair treatings were carried out to 50 monitors by the following methods. And the results of the organoleptic tests about hair treating effects (i. e. feel when used) of the hair treating agents were obtained. The results of organoleptic tests were summarized in Table 9.

The Method for Hair Treating with Hair Conditioners

After ordinary shampoo, a specimen of each hair conditioners (Examples 35–37) was applied to hair and spread by combing, and then rinsed and dried using a dryer.

The Method for Hair Treating with Hair Colorings

No. 1 agents and No. 2 agents of the hair colorings (Example 38 and 40) were mixed (the wt. % ratio of No. 1 agents to No. 2 agents was 1:1). This mixture was applied to hair and left for 30 minutes. Then, the hair was rinsed and dried using a dryer.

In a Case of Acidic Hair Coloring Materials)

The acidic hair coloring materials (Example 39) was applied to hair and left for 15 minutes at 45° C. Then, the hair was rinsed and dried using a dryer.

The Method for Hair Treating with Waving Agents

In a Case of Straight Type Permanent Wave

No. 1 agents of the waving agents (Example 41 and 42) were coated to hair and spread by combing and the hair was formed to the straight shape, and the hair was left for 15 minutes. Then No. 2 agents was coated to hair and spread by combing and left for 10 minutes. Finally, the hair was rinsed and dried using a dryer.

The Method for Hair Treating with Finishing Agents

The finishing agents (Example 43–47) was coated to hair and spread. Further, after ordinary shampoo, removavility of color wax was examined by comparing treated hair with untreated hair.

TABLE 9

| feel when used | hair treating agent (Example) | | | | | | | | | | | | |
|---|---|---|---|---|---|---|---|---|---|---|---|---|---|
| | 35 | 36 | 37 | 38 | 39 | 40 | 41 | 42 | 43 | 44 | 45 | 46 | 47 |
| slippery feel | ⊚ | ○ | Δ | Δ | Δ | Δ | Δ | Δ | — | — | — | — | — |
| soft feel | ⊚ | Δ | Δ | ○ | ○ | ○ | ○ | ○ | Δ | Δ | ⊚ | ○ | ○ |
| moist feel | ⊚ | ⊚ | Δ | ○ | ○ | ○ | ○ | ○ | ○ | Δ | ○ | ⊚ | ○ |
| smooth feel | Δ | Δ | ⊚ | Δ | Δ | Δ | Δ | Δ | ○ | ○ | ○ | ○ | ○ |
| rustle feeling | Δ | ○ | ⊚ | Δ | Δ | Δ | Δ | Δ | Δ | ⊚ | Δ | Δ | ○ |
| slightly oily feel | ○ | ○ | ○ | ⊚ | ⊚ | ⊚ | ⊚ | ⊚ | ○ | ○ | ○ | Δ | Δ |
| well spread of cream | — | — | — | ○ | ○ | ○ | ○ | ○ | ⊚ | ○ | ○ | ○ | ○ |
| no stickiness | — | — | — | — | — | — | — | — | ⊚ | ⊚ | ⊚ | ⊚ | ⊚ |
| brightness of color developing | — | — | — | — | — | — | — | — | — | — | — | — | ⊚ |
| non congealing of hair top | — | — | — | — | — | — | — | — | ○ | ⊚ | ⊚ | ⊚ | ⊚ |
| removavility of color wax | — | — | — | — | — | — | — | — | — | — | — | — | ⊚ |

In Table 9, ⊚ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as slippery feel, soft feel, moist feel, smooth feel, rustle feeling, slightly oily feel, salt resistance of hair treating agents, prevention of loss of color after hair colorings, well spread of cream, no stickiness, brightness of color developing of color wax, non congealing of hair top, easy removing of wax by shampoo etc. Further, in the preparation process of hair treating agent since it is possible by using the compositions blended in a hair treating agents of the present invention to blend esters and alcohols etc. at a time, the production process may be remarkably simplified.

Example of the Third Embodiment

The third embodiment of the present invention is illustrated more concretely according to the Examples.
(Preparation of the Compositions Blended in Hair Treating Agents)

Examples 48–59

The amount (kg) shown in Table 10 and Table 11 of ingredients were poured into a vessel and mixed, and the mixture was heated to the temperature shown in Table 10 and Table 11, then stirred and dissolved completely. Thus, the compositions blended in a hair treating agents (Examples 4-859) of the present invention were prepared.

TABLE 10

| | Example | | | | | |
|---|---|---|---|---|---|---|
| | 48 | 49 | 50 | 51 | 52 | 53 |
| | heating temp (° C.) | | | | | |
| ingredient (kg) | 80 | 75 | 85 | 85 | 90 | 90 |
| glycelin fatty acid ester | — | 8[1] | — | — | — | — |
| lipophilic glyceryl monostearat | 11 | — | 30 | — | — | — |
| lipophilic glyceryl monooleate | — | — | — | — | — | — |
| pentaerithritol tetra-2-ethylhexanoate | — | — | — | — | 25 | — |
| isopropyl myristate | — | — | — | 5 | — | — |
| myristyl myristate | — | — | — | — | — | — |
| isopropyl palmitate | 11 | — | — | — | — | — |
| butyl stearate | — | — | — | — | — | — |
| di (2-ethylhexyl) succinate | — | — | — | — | — | 25 |
| diisobutyl adipate | 7 | — | — | — | — | — |
| myristyl alcohol | 21 | 20 | — | — | — | — |
| hexyldecanol | — | — | — | — | — | — |
| cetanol | — | — | — | — | — | — |
| oleyl alcohol | 3 | — | — | — | — | — |
| behenyl alcohol | — | 12 | 40 | — | — | — |
| lanolin alcohol | — | — | — | 10 | — | — |
| ethanol | — | 8 | — | — | — | — |
| benzyl alcohol | — | — | — | 2 | — | — |
| 1,3-butylene glycol | — | — | — | — | 9 | 8.8 |
| dipropylene glycol | 7 | — | — | — | — | — |
| polyoxyethylene lauryl ether | — | — | — | 10[3] | — | — |
| polyoxyethylene cetyl ether | — | — | — | — | 37.3[5] | 38[5] |
| polyoxyethylene hydrogenated castor oil | 1[10] | 8[11] | — | — | — | — |
| lauric acid diethanolamide | — | — | — | 8 | — | — |
| coconut fatty acid diethanolamide | — | — | — | — | — | — |
| dimethyl stearylamine | 11 | — | 20 | — | — | — |
| hydrogenated oil | 9 | — | — | — | — | — |
| mink oil | — | — | — | — | — | — |
| olive oil | 7 | — | — | — | — | — |
| castor oil | — | 23 | — | — | — | — |
| shea butter | — | 2 | — | — | — | — |
| sodium cetyl sulfate | — | — | — | — | — | — |
| sodium palmitoyl N-methyl taurate | — | — | — | — | — | — |
| sodium tetradecen sulfonate | — | — | — | — | — | — |
| sodium polyoxyethylene oleyl ether phosphate triethanolamine | — | — | — | 13 | — | — |
| N-cocoyl-L-glutamate[13] | — | — | — | — | — | — |
| α olefin oligomer | 5 | — | — | — | — | — |

TABLE 10-continued

| | Example | | | | | |
|---|---|---|---|---|---|---|
| | 48 | 49 | 50 | 51 | 52 | 53 |
| | heating temp (° C.) | | | | | |
| ingredient (kg) | 80 | 75 | 85 | 85 | 90 | 90 |
| squalane | — | — | — | — | 0.2 | 0.2 |
| microcrystalline wax | — | — | — | — | 5.5 | 5 |
| liquid petrolatum | — | — | — | 52 | — | — |
| ceresin | — | — | 10 | — | — | — |
| candelilla wax | — | — | — | — | 23 | 23 |
| beeswax | — | — | — | — | — | — |
| hydrochloric acid salt of N-[3-alkyl (12, 14)oxy-2-hydroxypropyl]- L-arginine | — | 5[12] | — | — | — | — |
| polyglyceryl diisostearate | — | 2 | — | — | — | — |
| lactic acid | 7 | — | — | — | — | — |
| methyl polysiloxane | — | — | — | — | — | — |
| stearamidopropyl dimethylamine | — | 12 | — | — | — | — |
| purified water | — | — | — | — | — | — |

TABLE 11

| | Example | | | | | |
|---|---|---|---|---|---|---|
| | 54 | 55 | 56 | 57 | 58 | 59 |
| | heating temp (° C.) | | | | | |
| ingredient (kg) | 80 | 70 | 85 | 85 | 80 | 80 |
| glycelin fatty acid ester | 10[2] | — | — | — | — | — |
| lipophilic glyceryl monostearat | — | — | — | — | — | 4 |
| lipophilic glyceryl monooleate | — | — | 4 | 4 | — | — |
| pentaerithritol tetra-2-ethylhexanoate | — | — | — | — | — | — |
| isopropyl myristate | — | — | 10 | 10 | — | 4 |
| myristyl myristate | — | — | — | — | 10 | — |
| isopropyl palmitate | — | 8 | — | — | — | — |
| butyl stearate | 5 | — | — | — | — | — |
| di (2-ethylhexyl) succinate | — | — | — | — | — | — |
| diisobutyl adipate | — | — | — | — | — | — |
| myristyl alcohol | — | — | — | — | — | — |
| hexyldecanol | 1 | — | 1 | 1 | — | 1 |
| cetanol | 54 | 60 | 57 | 56.5 | 65 | 50 |
| oleyl alcohol | — | — | — | — | — | — |
| behenyl alcohol | — | — | — | — | — | — |
| lanolin alcohol | — | — | — | — | — | — |
| ethanol | — | — | — | — | — | — |
| benzyl alcohol | — | — | — | — | — | — |
| 1,3-butylene glycol | — | — | — | — | — | — |
| dipropylene glycol | — | — | — | — | — | — |
| polyoxyethylene lauryl ether | — | — | 7[4] | 7[4] | — | — |
| polyoxyethylene cetyl ether | 5[3] | 15[6] | 8[7] | 8[7] | 20[8] | 5[9] |
| polyoxyethylene hydrogenated castor oil | — | — | — | — | — | — |
| lauric acid diethanolamide | — | — | — | — | — | — |
| coconut fatty acid diethanolamide | — | — | 3 | 3 | — | — |
| dimethyl stearylamine | — | — | — | — | — | — |
| hydrogenated oil | — | — | — | — | 5 | — |
| mink oil | 5 | — | — | — | — | — |
| olive oil | — | — | — | — | — | — |
| castor oil | — | — | — | — | — | — |
| shea butter | — | — | — | — | — | — |
| sodium cetyl sulfate | — | 7 | — | — | — | — |
| sodium palmitoyl N-methyl taurate | — | — | — | — | — | 5 |
| sodium tetradecen sulfonate | 10 | — | — | — | — | 5 |
| sodium polyoxyethylene oleyl ether phosphate triethanolamine | 10 | — | 10 | 10 | — | — |
| N-cocoyl-L-glutamate[13] | | | | | | |

TABLE 11-continued

| | Example | | | | | |
|---|---|---|---|---|---|---|
| | 54 | 55 | 56 | 57 | 58 | 59 |
| | heating temp (° C.) | | | | | |
| ingredient (kg) | 80 | 70 | 85 | 85 | 80 | 80 |
| α olefin oligomer | — | — | — | — | — | — |
| squalane | — | — | — | — | — | — |
| microcrystalline wax | — | — | — | — | — | — |
| liquid petrolatum | — | — | — | — | — | — |
| ceresin | — | — | — | — | — | — |
| candelilla wax | — | — | — | — | — | 8 |
| beeswax | — | 5 | — | — | — | 8 |
| hydrochloric acid salt of N-[3-alkyl (12, 14) oxy-2-hydroxypropyl]- L-arginine | — | — | — | — | — | — |
| polyglyceryl diisostearate | — | — | — | — | — | — |
| lactic acid | — | — | — | — | — | — |
| methyl polysiloxane | — | — | — | 0.5 | — | — |
| stearamidopropyl dimethylamine | — | — | — | — | — | — |
| purified water | — | 5 | — | — | — | 10 |

1)–13) in Tables 10 and Table 11 are indicating,
1) glyceryl mono, di and tristearate,
2) mono and diglyceryl oleate and stearate,
3) 7 EO,
4) 23 EO,
5) 5.5 EO+10 EO[weight ratio 1:2],
6) 5.5 EO+30 EO+40 EO[weight ratio 1:1:1],
7) 40 EO,
8) 5 EO+40 EO[weight ratio 5:15],
9) 13 EO,
10) 60 EO,
11) 25 EO,
12) solids contents (60 wt. %)+ethanol (20 wt. %)+water (20 wt. %),
13) containing 70 wt. % of water.

(Preparation of Hair Conditioners)

Examples 60 and 61

Initial purified water was heated to the temperature of 80–85° C. On the other hand, the composition blended in hair conditioner obtained above (Example 48), additive composition, and anionic surfactant derived from amino acid were mixed and heated to the temperature of 80–85° C., and then dissolved homogeneously.

The homogeneous dissolved material was added to the above-mentioned hot water with constant stirring and emulsified. Then the emulsion was cooled down to the temperature of 50° C. with constant stirring. Next, perfumes was added, then purified water (add water) was added so as to adjust the total weight to be 100 kg and then mixed homogeneously. Thus, the hair conditioners of the present invention (Examples 60 and 61) were prepared. The ingredients and contents (kg) are shown in Table 12.

Example 62

Initial purified water was heated to the temperature of 80–85° C. On the other hand, the compositions blended in hair conditioner obtained above (Example 48), phenoxyethanol, N-acyl glutamic acid ester were mixed and heated to the temperature of 80–85° C., and then dissolved homogeneously. The homogeneous dissolved material was added to the above-mentioned hot water with constant stirring and emulsified. Then the emulsion was cooled down to the temperature of 50° C. with constant stirring. Next, perfume was added, and further, purified water (add water) was added so as to adjust the total weight to be 100 kg and then mixed homogeneously. Thus, the hair conditioner of the present invention was prepared. The ingredients and contents (kg) are shown in Table 12.

Examples 63 and 64

Initial purified water, glycolic acid, and glutamic acid were mixed and heated to the temperature of 80–85° C. to prepare aqueous solution. On the other hand, the composition blended in hair conditioner obtained above (Example 49) was heated to the temperature of 80–85° C., and then dissolved homogeneously0.

The homogeneous dissolved material was added to the above-mentioned hot water with constant stirring and emulsified. Then the emulsion was cooled down to the temperature of 38° C. with constant stirring. Next, preservatives and perfumes etc. were added, and finally, purified water (add water) was added so as to adjust the total weight to be 100 kg and then mixed homogeneously. Thus, the hair conditioner of the present invention was prepared. The ingredients and contents (kg) are shown in Table 12.

Example 65

Initial purified water was heated to the temperature of 85–90° C. On the other hand, the composition blended in hair conditioner obtained above (Example 50) and lactic acid were mixed and heated to the temperature of 85–90° C., and then dissolved homogeneously. The homogeneous dissolved material was added to the above-mentioned hot water with constant stirring and emulsified. Then the emulsion was cooled down to the temperature of 50° C. with constant stirring. Next, perfume was added, and further, purified water (add water) was added so as to adjust the total weight to be 100 kg and then mixed homogeneously. Thus, the hair conditioner of the present invention was prepared. The ingredients and contents (kg) are shown in Table 12.

Examples 66 and 67

Initial purified water and TEA were mixed and heated to the temperature of 85–90° C. to prepare aqueous solution. On the other hand, the composition blended in hair conditioner obtained above (Example 53), stearyl alcohol, candelilla wax, methyl polysiloxane, isopropyl palmitate, dioctyl succinate, stearic acid and preservative were mixed and heated to the temperature of 85–90° C., and then dissolved homogeneously.

The homogeneous dissolved material was added to the above-mentioned hot water with constant stirring and emulsified. After the emulsion was cooled down to the temperature of 70° C. with constant stirring, PVP-VA copolymer was added and mixed homogeneously. After cooled to 50° C., perfumes and, if necessary, polyethylene glycol were added, and finally, purified water (add water) was added so as to adjust the total weight to be 100 kg and then mixed homogeneously. Thus, the hair conditioner (so called "non rinsing treatment") of the present invention was prepared. The ingredients and contents (kg) are shown in Table 12.

Example 68

Initial purified water and sodium hydroxide were mixed and heated to the temperature of 80–90° C. to prepare aqueous solution. On the other hand, the composition blended in hair conditioner obtained above (Example 53), dioctyl succinate, polyethylene glycol, and hydroxystearic acid were mixed and heated to the temperature of 85–90° C., and then dissolved homogeneously. The homogeneous dissolved material was added to the above-mentioned hot water with constant stirring and emulsified. Then the emulsion was cooled down to the temperature of 50–60° C. with constant stirring Next, PVP-VA copolymer, citric acid, pigments, and perfumes were added, and finally purified water (add water) was added so as to adjust the total weight to be 100 kg and then mixed homogeneously. Thus, the hair conditioner (so called "non rinsing treatment") of the present invention was prepared. The ingredients and contents (kg) are shown in Table 12.

Example 69

The composition blended in hair conditioner (Example 53), methyl polysiloxane, hydrogenated oil, and polypropylene glycol oligosuccinate were mixed and heated to the temperature of 85–90° C., and then dissolved homogeneously. Then, to the homogeneous dissolved material, 12.5 kg of purified water was added with constant stirring to prepare 100 kg of emulsion. Thus, the hair conditioner (so called "non rinsing treatment") of the present invention was prepared. The ingredients and contents (kg) are shown in Table 12.

3) ingredients (wt. %); dipentaerythritol fatty ester [the full esters prepared from dipentaerythritol and mixed fatty acid (12-hydroxystearic acid:stearic acid:rosin= 4:1.5:0.5)] (50), triglyceryl cocoate (30), isopropyl palmitate (10), diisobutyl adipate (10),
4) ingredients (wt. %); dimethylsiloxane methylstearoxysiloxane copolymer (50), diisopropyl adipate (25), ), diisobutyl adipate (25),
5) trade name "CAE" (Ajinomoto co.),
6) parabens,
7) average molecular weight 2 million,
8) 100 cs,
9) 20 cs,
10) 50 cs.

(Preparation of Oxidizing Hair Coloring Agents)

Examples 70 and 71

Preparation of No. 1 Agents

To initial purified water that was heated to the temperature of 80–85° C., dye intermediates (resorcinol, p-phenylene diamine, m-aminophenol, p-aminophenol), antioxidant, and, if necessary, EDTA, NMP were added to prepare aqueous solution.

On the other hand, the composition blended in hair coloring (Example 57 or 56) was dissolved homogeneously at the temperature of 80–85° C. Then, the homogeneous

TABLE 12

| | Example | | | | | | | | | |
|---|---|---|---|---|---|---|---|---|---|---|
| | 60 | 61 | 62 | 63 | 64 | 65 | 66 | 67 | 68 | 69 |
| | heating temp (° C.) | | | | | | | | | |
| ingredient (kg) | 80~85 | 80~85 | 80~85 | 80~85 | 80~85 | 85~88 | 80~85 | 80~85 | 80~90 | 80~90 |
| composition blended | Example 48 | Example 48 | Example 48 | Example 49 | Example 49 | Example 50 | Example 53 | Example 53 | Example 53 | Example 53 |
| in hair conditioner | 25 | 10 | 12 | 5 | 15 | 15 | 20 | 20 | 20 | 62.5 |
| initial purified water | 80 | 80 | 80 | 80 | 80 | 80 | 40 | 40 | 40 | — |
| addive composition | 1[3] | 0.5[4] | — | — | — | — | — | — | — | — |
| preservative | proper amount | proper amount | — | 0.2[5] | 0.2[5] | — | 0.15[6] | 0.15[6] | — | — |
| perfume | proper amount | proper amount | proper amount | proper amount | proper amount | proper amount | proper amount | proper amount | proper amount | — |
| pigment | — | — | — | — | — | — | — | — | proper amount | — |
| anionic surfactants derived from amino acid | 0.8 | 0.7 | — | — | — | — | — | — | — | — |
| phenoxyethanol | — | — | 1 | — | — | — | — | — | — | — |
| stearyl alcohol | — | — | — | — | — | — | 5 | 4 | — | — |
| polyethylene glycol | — | — | — | — | — | — | — | 0.2[7] | 0.5 | — |
| glycolic acid[1] | — | — | — | 0.3 | 0.9 | — | — | — | — | — |
| glutamic acid | — | — | — | 0.2 | 0.6 | — | — | — | — | — |
| stearic acid | — | — | — | — | — | — | 4 | 4 | — | — |
| hydroxystearic acid | — | — | — | — | — | — | — | — | 4 | — |
| 90% lactic acid | — | — | — | — | — | 1 | — | — | — | — |
| citric acid | — | — | — | — | — | — | — | — | 0.4 | — |
| candelilla wax | — | — | — | — | — | — | 5 | — | — | — |
| dimetyl polysiloxane | — | — | — | — | — | — | 5[8] | 7[9] | — | 10[10] |
| N-acyl glutamic acid ester | — | — | 1 | — | — | — | — | — | — | — |
| isopropyl palmitate | — | — | — | — | — | — | — | 4 | — | — |
| dioctyl succinate | — | — | — | — | — | — | 8 | 2 | 15 | — |
| polypropylene glycol oligosuccinate | — | — | — | — | — | — | — | — | — | 12.5 |
| TEA | — | — | — | — | — | — | 1.1 | 1.1 | — | — |
| sodium hydroxide | — | — | — | — | — | — | — | — | 0.3 | — |
| PVP-VA copolymer[2] | — | — | — | — | — | — | 1 | 2 | 1 | — |
| hydrogenated oil | — | — | — | — | — | — | — | — | — | 12.5 |

1)–10) in Tables 12 are indicating, 1) 70% contents,
2) containing 50% ethanol, dissolved material was added to the above-mentioned hot aqueous solution with constant stirring and emulsified. After the emulsion was cooled down to the temperature of 45–55° C. with constant stirring, additives, if necessary, such as MEA, EDTA, 60% 1-hydroxyethane-1,1-diphosphonic acid were added, and finally, purified water (add water) was added so as to adjust the total weight to be 100 kg. Thus No. 1 agent was prepared. The ingredients and contents (kg) are shown in Table 13.

Preparation of No. 2 Agents

The compositions blended in hair coloring (Example 58 or 56) was dissolved homogeneously at the temperature of 80–85° C. Then, the homogeneous dissolved material was added with constant stirring to initial purified water that was heated to the temperature of 80–85° C., and emulsified. After the emulsion was cooled down to the temperature of 45° C. with constant stirring, 60% 1-hydroxyethane-1,1-diphosphonic acid, dibasic sodium phosphate (12 hydrate) were added, and then 35 wt. % hydrogen peroxide aqueous solution was added. And finally, purified water (add water) was added so as to adjust the total weight to be 100 kg. Thus No. 2 agent was prepared. The ingredients and contents (kg) are shown in Table 13.

TABLE 13

| | Example | |
|---|---|---|
| blending component (kg) | 70 | 71 |
| No. 1 agent | | |
| composition blended in hair coloring | Example 57 25 | Example 56 20 |
| dye intermediate | proper amount | proper amount |
| antioxidant | 0.8[1)] | proper amount |
| MEA | proper amount | proper amount |
| EDTA | 0.2 | — |
| 60% hydroxyethane diphosphoric acid | — | 0.17 |
| NMP | 3 | — |
| initial purified water | 60 | 60 |
| No. 2 agent | | |
| composition blended in hair coloring | Example 58 5 | Example 56 5 |
| 60% hydroxyethane diphosphoric acid | 0.17 | 0.17 |
| dibasic sodium phosphate (12 hydrate) | 0.26 | 0.26 |
| 35% hydrogen peroxide aqueous solution | 16.9 | 16.9 |
| initial purified water | 60 | 60 |

1) in Tables 13 are indicating 50% ammonium thioglycolate.

(Preparation of Acidic Hair Coloring Materials)

Example 72

15 kg of the composition blended in hair coloring (Example 59), 3 kg of candelilla wax, 0.1 kg of parabens were mixed and heated to 80–85° C. and homogeneously dissolved. On the other hand, 50 kg of 1% xanthan gum aqueous solution, tar pigments (0.3 kg of black No. 401, 0.3 kg of violet No. 401, and 0.6 kg of orange No. 205) were heated to 80–85° C. to prepare aqueous solution. Then, the aforementioned homogeneous dissolved material was added to the above-mentioned the aqueous solution with constant stirring and emulsified.

After the emulsion was cooled down to the temperature of 40° C., 5 kg of benzyl alcohol, 2.5 kg of diethylene glycol monoethyl ether, 1 kg of phosphoric acid, 2 kg of 70% glycolic acid aqueous solution, 5 kg of 40% ammonium glycolate were added, further, purified water (add water) was added so as to adjust the total weight to be 100 kg. Thus the acidic hair coloring material was prepared.

(Preparation of Waving Agents)

Example 73

Preparation of No. 1 Agents

The composition blended in waving agent (Example 73) was heated to the temperature of 80–85° C. and homogeneously dissolved and added to initial purified water that was previously heated to 80–85° C., stirred and emulsified. Then the emulsion was cooled down to the temperature of 45° C., 50% ammonium thioglycolate, strong ammonia solution and ammonium bicarbonate were added to the emulsion, further, purified water (add water) was added so as to adjust the total weight to be 100 kg. Thus No. 1 agent was prepared. The ingredients and contents (kg) are shown in Table 14.

Preparation of No. 2 Agents

To lauryl trimethyl ammonium chloride and sodium bromate, purified water was added so as to adjust the total weight to be 100 kg. Thus, No. 2 agent was prepared. Ingredients and contents (kg) are shown in Table 14.

Example 74

Preparation of No. 1 Agents

No. 1 agent was prepared by the same process as Example 73 except that the composition blended in waving agent of Example 57 (15 wt. %) was used instead of Example 54 (10 wt. %). Ingredients and contents (kg) are shown in Table 14.

Preparation of No. 2 Agents

The composition blended in waving agent (Example 57) was heated to 80–85° C. and homogeneously dissolved, and added to initial purified water that was previously heated to 80–85° C., and then stirred and emulsified. After the emulsion was cooled down to the temperature of 45° C. with constant stirring, sodium bromate was added to the emulsion, further, purified water (add water) was added so as to adjust the total weight to be 100 kg. Thus No. 2 agent was prepared. Ingredients and contents (kg) are shown in Table 14.

TABLE 14

| | Example | |
|---|---|---|
| ingredient (kg) | 73 | 74 |
| No. 1 agent | | |
| composition blended in waving agent | Example 54 10 | Example 57 15 |
| 50% ammonium thioglycolate | 13 | 13 |
| strong ammonia solution | proper amount | proper amount |
| ammonium bicarbonate | proper amount | proper amount |
| initial purified water | 60 | 60 |
| No. 2 agent | | |
| composition blended in waving agent | — | Example 57 15 |
| sodium bromate | 8 | 8 |
| lauryl trimethyl ammonium chloride | 1 | — |
| initial purified water | — | 60 |

(Preparation of Finishing Agents)

Example 75

40 kg of initial purified water, 0.2 kg of high polymerized polyethylene glycol (average molecular weight 2 million), 1.1 kg of TEA were mixed and heated to the temperature of 85–90° C. to prepare aqueous solution. On the other hand, 20 kg of the composition blended in finishing agent (Example 52), 5 kg of stearyl alcohol, 5 kg of methyl polysiloxane (100 cs), 8 kg of pentaerithritol tetra-2- ethylhexanoate, 5 kg of candelilla wax, 4 kg of stearic acid, and proper amount of parabens were mixed and heated to the temperature of 85–90° C. and dissolved homogeneously.

Then, the homogeneous dissolved material was added to the above-mentioned hot aqueous solution with constant stirring and emulsified. After the emulsion was cooled down to the temperature of 80° C. with stirring, 3 kg of additive compositions[1] was added and mixed homogeneously. After cooled to 45° C., perfumes and purified water (add water) was added so as to adjust the total weight to be 100 kg. Thus the finishing agent of the present invention was prepared.

In a Case of Straight Type Permanent Wave

No. 1 agents of the waving agents (Example 74) were coated to hair and spread by combing and the hair was formed to the straight shape, and the hair was left for 10 minutes. Then No. 2 agents was coated to hair and spread by combing and left for 10 minutes. Finally, the hair was rinsed and dried using a dryer.

The Method for Hair Treating with Finishing Agents

The finishing agents (Example 75) was coated to hair and spread.

TABLE 15

| feel when used | hair treating agent (Example) | | | | | | | | | | | | | | | |
|---|---|---|---|---|---|---|---|---|---|---|---|---|---|---|---|---|
| | 60 | 61 | 62 | 63 | 64 | 65 | 66 | 67 | 68 | 69 | 70 | 71 | 72 | 73 | 74 | 75 |
| soft feel | Δ | ◎ | Δ | ◎ | ◎ | Δ | Δ | ◎ | Δ | Δ | Δ | Δ | ○ | ◎ | ○ | Δ |
| moist feel | ◎ | ○ | ○ | ◎ | ◎ | ◎ | Δ | ○ | ○ | ○ | Δ | Δ | ○ | ◎ | ◎ | ○ |
| slightly oily feel | ○ | ○ | ○ | ○ | ○ | Δ | Δ | ○ | ○ | ○ | ◎ | ◎ | ○ | ○ | ○ | ○ |
| luster | Δ | Δ | Δ | ◎ | ◎ | Δ | ◎ | ◎ | ◎ | ◎ | Δ | Δ | Δ | Δ | Δ | ◎ |
| rustle feeling | ○ | ○ | ○ | ◎ | ◎ | ○ | ◎ | ◎ | ◎ | ◎ | Δ | Δ | ○ | ○ | Δ | ◎ |
| smooth feel | Δ | ◎ | Δ | Δ | Δ | Δ | ○ | ○ | ○ | ○ | ◎ | ◎ | Δ | ◎ | ◎ | ○ |
| increased volume feel | — | — | — | — | — | — | ◎ | ◎ | ◎ | ◎ | — | — | — | — | — | ◎ |
| setting ability | — | — | — | — | — | — | ◎ | ◎ | ◎ | ◎ | — | — | ○ | ○ | ○ | — |
| smooth combing | Δ | Δ | Δ | Δ | Δ | Δ | ◎ | ◎ | ◎ | ◎ | ○ | ○ | ◎ | ○ | ○ | ○ |
| low irritation | ◎ | ◎ | ◎ | ◎ | ◎ | ◎ | — | — | — | — | Δ | Δ | ○ | ◎ | ◎ | ○ |
| well spread of cream | — | — | — | — | — | — | ○ | ○ | ○ | ○ | ◎ | ◎ | ◎ | ○ | ◎ | ◎ |
| no stickiness | — | — | — | — | — | — | ◎ | ◎ | ◎ | ◎ | — | — | — | — | — | ◎ |

1) ingredients (wt. %); polyvinylpyrrolidone (1.3), dipropylene glycol (12.5), ethanol (5), N-methacryloyl ethyl-N, N-dimethyl ammonium α-N-methyl carboxybetaine.alkyl methacrylate copolymer (50), purified water (31 2).

(The Organoleptic Tests About Hair Treating Effects of the Hair Treating Agents)

Hair treatments were carried out to 50 monitors by the following methods. And the results of the organoleptic tests about hair treating effects (i. e. feel when used) of the hair treating agents were obtained. The results of organoleptic tests were summarized in Table 15.

The Method for Hair Treating with Hair Conditioners

After ordinary shampoo, a specimen of each hair conditioners (Examples 60–65) was applied to hair and spread by combing, and then rinsed and dried using a dryer.

In a Case of so Called "non Rinsing Treatments"

By the same way to the hair treatments of finishing agents mentioned below, hair was treated using non rinsing treatments (Examples 66–69).

The Method for Hair Treating with Hair Colorings

No. 1 agents and No. 2 agents of the hair colorings (Example 70 and 71) were mixed (the wt. % ratio of No. 1 agents to No. 2 agents was 1:1). This mixture was applied to hair and left for 30 minutes. Then, the hair was rinsed and dried using a dryer.

In a Case of Acidic Hair Coloring Materials)

The acidic hair coloring materials (Example 72) was applied to hair and left for 15 minutes at 45° C. Then, the hair was rinsed and dried using a dryer.

The Method for Hair Treating with Waving Agents

In a Case of Curling Type Permanent Wave

No. 1 agents of the waving agents (Example 73) were coated to hair and spread by combing, and the hair was wound to a rod and heated for 7 minutes at room temperature. Then No. 2 agents was coated by an applicator and left for 7 minutes. After the rod was removed, the hair was rinsed and dried using a dryer.

In Table 15, ◎ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as soft feel, moist feel, slightly oily feel, luster, rustle feeling, smooth feel, natural hairline (increased volume feel), setting ability, smooth combing, low irritation, well spread of cream, no stickiness, salt resistance of hair treating agents etc. Further, in the preparation process of hair treating agent since it is possible by using the compositions blended in a hair treating agents of the present invention to blend esters, alcohols, nonionic surfactants and fatty acids etc. at a time, the production process may be remarkably simplified.

Example of the Fourth Embodiment

The fourth embodiment of the present invention is illustrated more concretely according to the Examples.

(Preparation of the Compositions Blended in Hair Treating Agents)

Examples 76–85

The amount (kg) shown in Table 16 and Table 17 of ingredients were poured into a vessel and mixed, and the mixture was heated to the temperature shown in Table 16 and Table 17, then stirred and dissolved completely. Thus, the compositions blended in a hair treating agents (Examples 76–85) of the present invention were prepared.

TABLE 16

| ingredient (kg) | Example 76 | 77 | 78 | 79 | 80 |
|---|---|---|---|---|---|
| heating temp (° C.) | 70 | 70 | 80 | 80 | 75 |
| mono and diglyceryl oleate and stearate | — | — | — | — | — |
| lipophilic glyceryl monostearate | — | — | 33 | — | — |
| glyceryl monooleate | — | 7 | — | — | — |
| isononyl isononanoate | — | — | — | 10 | — |
| isopropyl myristate | — | 5 | — | — | 6 |
| isopropyl palmitate | — | — | — | — | — |
| stearyl stearate | — | — | 10 | — | — |
| diisobutyl adipate | 7 | — | — | — | — |
| myristyl alcohol | 55 | — | — | — | — |
| hexyldecanol | 1 | 1 | — | — | — |
| cetanol | — | 51 | — | — | — |
| behenyl alcohol | 10 | — | 3 | — | — |
| arachyl alcohol | — | — | 5 | — | — |
| 1,3-butylene glycol | — | — | — | — | — |
| cetostearyl alcohol | — | — | — | 78 | 54 |
| polyoxyethylene lauryl ether[1] | — | — | — | — | — |
| polyoxyethylene cetyl ether | — | 5[4] | — | 8[5] | — |
| polyoxyethylene hydrogenated castor oil[2] | — | — | 17 | — | — |
| coconut fatty acid monoethanolamide | — | — | — | — | 12 |
| sorbitan monostearate | — | — | 7 | — | 4 |
| polyoxyethylene stearoxyl amide[3] | — | — | — | — | — |
| dimethyl stearylamine | 20 | — | — | — | — |
| lauric acid | — | 5 | — | — | — |
| myristic acid | 2 | — | — | — | — |
| stearic acid | — | — | 12 | 4 | 8 |
| oleic acidr | — | — | — | — | 4 |
| lanolin fatty acid | — | — | — | — | — |
| sodium tetradecen sulfonate | — | 8 | — | — | 8 |
| sodium palmitoyl N-methyl taulate | — | 2 | — | — | — |
| sulfated castor oil[8] | — | 10 | — | — | — |
| triethanolamine N-cocoyl-L-glutamate[9] | — | — | — | — | — |
| mink wax | — | — | — | — | — |
| shea butter | 5 | — | — | — | — |
| paraffin | — | — | — | — | — |
| liquid petrolatum | — | — | 13 | — | — |
| rice bran wax | — | — | — | — | — |
| methyl polysiloxane | — | — | — | — | — |
| polypropylene glycol oligosuccinate | — | 5 | — | — | — |
| purified water | — | 1 | — | — | 4 |

TABLE 17

| ingredient (kg) | Example 81 | 82 | 83 | 84 | 85 |
|---|---|---|---|---|---|
| heating temp (° C.) | 70 | 75 | 80 | 80 | 75 |
| mono and diglyceryl oleate and stearate | 4 | 4 | 4.3 | 4.3 | 5 |
| lipophilic glyceryl monostearate | — | — | — | — | — |
| glyceryl monooleate | — | — | — | — | — |
| isononyl isononanoate | — | — | — | — | — |
| isopropyl myristate | — | — | 8.6 | 8.7 | 10 |
| isopropyl palmitate | 8 | 8 | — | — | — |
| stearyl stearate | — | — | — | — | — |
| diisobutyl adipate | — | — | — | — | — |
| myristyl alcohol | — | — | — | — | — |
| hexyldecanol | — | — | — | — | — |
| cetanol | 47.5 | 48 | 44.5 | 44.8 | 52 |
| behenyl alcohol | — | — | — | — | — |
| arachyl alcohol | — | — | — | — | — |
| 1,3-butylene glycol | — | — | 2.9 | 2.9 | 3.5 |
| cetostearyl alcohol | — | — | — | — | — |
| polyoxyethylene lauryl ether[1] | 4 | 4 | — | — | — |
| polyoxyethylene cetyl ether | — | — | 6.8[6] | 6.8[6] | 1[7] |
| polyoxyethylene hydrogenated castor oil[2] | — | — | — | — | — |
| coconut fatty acid monoethanolamide | 10 | 10 | — | — | — |
| sorbitan monostearate | — | — | — | — | — |
| polyoxyethylene stearoxyl amide[3] | — | — | 2.9 | 2.9 | 3.5 |
| dimethyl stearylamine | — | — | — | — | — |
| lauric acid | — | — | — | — | — |
| myristic acid | — | — | — | — | — |
| stearic acid | 14 | 14 | — | — | — |
| oleic acidr | — | — | — | — | — |
| lanolin fatty acid | — | — | 2.9 | 2.9 | 3.5 |
| sodium tetradecen sulfonate | 8 | 8 | — | — | — |
| sodium palmitoyl N-methyl taulate | — | — | 8.6 | 8.7 | 10 |
| sulfated castor oil[8] | — | — | — | — | — |
| triethanolamine N-cocoyl-L-glutamate[9] | — | — | 2.9 | 2.9 | 3.5 |
| mink wax | — | — | 2.9 | 2.9 | — |
| shea butter | — | — | 2.9 | 2.9 | — |
| paraffin | — | — | 1.4 | 1.4 | 2 |
| liquid petrolatum | — | — | — | — | — |
| rice bran wax | — | — | 0.6 | — | — |
| methyl polysiloxane | 0.5 | 0.5 | — | — | — |
| polypropylene glycol oligosuccinate | — | — | — | — | — |
| purified water | 4 | 3.5 | 7.8 | 7.9 | 6 |

1)–9) in Table 16 and Table 17 are indicating, 1) 23 EO,
2) 30 EO,
3) 4 EO,
4) 7 EO,
5) 5 EO+40 EO (weight ratio 1:1),
6) 40 EO,
7) 25 EO,
8) containing 50 wt. % water,
9) containing 70 wt. % water.

(Preparation of Hair Conditioners)

Example 86–88

Initial purified water was heated to the temperature of 80–85° C. On the other hand, the compositions blended in hair conditioner obtained above (Example 76) was heated to the temperature of 80–85° C., and then additive composition, preservatives, lactic acid was added to this, and then dissolved homogeneously.

Then, the homogeneous dissolved material was added to the above-mentioned hot initial water with constant stirring and emulsified. After the emulsion was cooled down to the temperature of 50° C. with constant stirring, perfume was added. And finally, purified water (add water) was added so as to adjust the total weight to be 100 kg, and then dissolved homogeneously. Thus, the hair conditioners of the present invention (Example 86–88) were prepared. The ingredients and contents (kg) are shown in Table 18.

Example 89

To initial purified water, preservatives and lactic acid were added and heated to the temperature of 80–85° C. to prepare aqueous solution. On the other hand, to the composition blended in hair conditioner obtained above (Example 76), additive compositions was added and heated to the temperature of 80–85° C., and then dissolved homogeneously. Then, the homogeneous dissolved material was added to the above-mentioned hot aqueous solution with constant stirring and emulsified. After the emulsion was cooled down to the temperature of 50° C. with constant stirring, perfumes were added. And finally, purified water (add water) was added so as to adjust the total weight to be 100 kg, and then dissolved homogeneously. Thus, the hair conditioner of the present invention (Example 89) was prepared. The ingredients and contents (kg) are shown in Table 18.

Example 90

The composition blended in hair conditioner (Example 77), that was previously heated to the temperature of 80–85° C. and dissolved homogeneously, was added with constant stirring to initial purified water, that was previously heated to the temperature of 80–85° C., and emulsified. After the emulsion was cooled down to the temperature of 45° C. with constant stirring, lactic acid and additive compositions were added. And finally, purified water (add water) was added so as to adjust the total weight to be 100 kg, and dissolved homogeneously. Thus, the hair conditioner of the present invention (Example 90) was prepared. The ingredients and contents (kg) are shown in Table 18.

Examples 91–96

To initial water, xanthan gum was added and heated to the temperature of 83–88° C., and then pigments were dissolved to this to prepare aqueous solution. On the other hand, the composition blended in hair conditioner obtained above (Example 83 and 85) and preservatives were mixed and heated to the temperature of 83–88° C., and then dissolved homogeneously.

The homogeneous dissolved material was added to the above-mentioned hot water with constant stirring and emulsified. Then the emulsion was cooled down to the temperature of 48° C. with constant stirring. Next, additive compositions was added, then purified water (add water) was added so as to adjust the total weight to be 100 kg and then mixed homogeneously. Thus, the hair conditioners of the present invention (Examples 91–96) were prepared. The ingredients and contents (kg) are shown in Table 18 and Table 19.

TABLE 19

| | Example | | | | |
|---|---|---|---|---|---|
| | 92 | 93 | 94 | 95 | 96 |
| | heating temp (° C.) | | | | |
| ingredient (kg) | 83~88 | 83~88 | 83~88 | 83~88 | 83~88 |
| composition blended in hair conditioner | Example 83 15 | Example 83 15 | Example 85 15 | Example 85 15 | Example 85 15 |
| initial water | 70 | 70 | 70 | 70 | 70 |
| additive composition | 5[6] | 5[6] | 5[6] | 5[6] | 5[6] |
| preservative | 0.15[7] | 0.15[7] | 0.15[7] | 0.15[7] | 0.15[7] |
| perfume | — | — | — | — | — |
| pigment | 0.05[9] | 0.0504[10] | 0.05[8] | 0.05[9] | 0.0504[10] |
| lactic acid | — | — | — | — | — |
| xanthan gum | 0.2 | 0.2 | 0.2 | 0.2 | 0.2 |

1)–10) in Table 18 and Table 19 are indicating,
1) ingredients (wt. %); propylene glycol dicaprate (75), caprylic capric acid triglyceride (12.5), polyoxypropylene (52 PO) butyl ether (12.5),
2) trade name "CAE" (Ajinomoto co.),
3) ingredients (wt. %); dimethylsiloxane·methylstearoxysiloxane copolymer (50), diisopropyl adipate (25), ), diisobutyl adipate (25),
4) ingredients (wt. %); shea butter (45), rice germ oil (45), 2-hexyldecyl isostearate (10),
5) trade name, "MERQUAT 100" (CALGON CORPORATION),
6) ingredients (wt. %); NMP (38), benzyl alcohol (20), polyoxypropylene methylglucoside ether (20), phosphoric acid (8), tartaric acid (8), water (6),
7) parabens,
8) orange No. 205,
9) orange No. 205 (0.029 kg)+violet No. 401 (0.011 kg)+black No. 401 (0.01 kg),
10) red No. 106 (0.0008 kg)+orange No. 205 (0.016 kg)+blue No. 1 (0.0016 kg)+violet No. 401 (0.016 kg)+black No. 401 (0.016 kg).

(Preparation of Oxidizing Hair Coloring Agents)

Example 97 and 98

Preparation of No. 1 Agents

To initial purified water that was heated to the temperature of 80–85° C., dye intermediates (resorcinol, phenylene

TABLE 18

| | Example | | | | | |
|---|---|---|---|---|---|---|
| | 86 | 87 | 88 | 89 | 90 | 91 |
| | heating temp (° C.) | | | | | |
| ingredient (kg) | 80~85 | 80~85 | 80~85 | 80~85 | 80~85 | 83~88 |
| composition blended in hair conditioner | Example 76 12 | Example 76 12 | Example 76 10 | Example 76 12 | Example 77 10 | Example 83 15 |
| initial water | 80 | 80 | 80 | 80 | 70 | 70 |
| additive composition | 1[1] | 1[3] | — | 2[4] | 0.25[5] | 5[6] |
| preservative | 0.2[2] | 0.2[2] | 0.2[2] | 0.2[2] | — | 0.15 [7] |
| perfume | proper amount | proper amount | proper amount | proper amount | — | — |
| pigment | — | — | — | — | — | 0.05[8] |
| lactic acid | 0.8 | 0.8 | 0.6 | 0.8 | 0.8 | — |
| xanthan gum | — | — | — | — | — | 0.2 | diamine, m-aminophenol, p-aminophenol), antioxidant, and, if necessary, NMP were added to prepare aqueous solution. On the other hand, cetanol was added to the composition blended in hair coloring (Example 80), and then dissolved homogeneously at the temperature of 80–85° C. Then, the homogeneous dissolved material was added to the above-mentioned hot aqueous solution with constant stirring and emulsified.

After the emulsion was cooled down to the temperature of 50–55° C. with constant stirring, additives, if necessary, such as MEA, strong ammonium solution, EDTA, 60% 1-hydroxyethane-1,1-diphosphonic acid were added, and finally, purified water (add water) was added so as to adjust the total weight to be 100 kg. Thus No. 1 agent was prepared. The ingredients and contents (kg) are shown in Table 20.

Preparation of No. 2 Agents

The composition blended in hair coloring (Example 83) was dissolved homogeneously at the temperature of 80–85° C. Then, the homogeneous dissolved material was added with constant stirring to initial purified water that was heated to the temperature of 80–85° C., and emulsified. After the emulsion was cooled down to the temperature of 45° C. with constant stirring, 60% 1-hydroxyethane-1,1-diphosphonic acid, dibasic sodium phosphate (12 hydrate) were added, and then 35 wt. % hydrogen peroxide aqueous solution was added. And finally, purified water (add water) was added so as to adjust the total weight to be 100 kg. Thus No. 2 agent was prepared. The ingredients and contents (kg) are shown in Table 20.

TABLE 20

| ingredient (kg) | Example 97 | Example 98 |
| --- | --- | --- |
| No. 1 agent | | |
| composition blended in hair coloring | Example 80 20 | Example 80 20 |
| cetanol | 5 | 5 |
| dye intermediate | proper amount | proper amount |
| antioxidant | proper amount | proper amount |
| MEA | proper amount | — |
| strong ammonia solution | — | 4 |
| EDTA | 0.2 | — |
| 60% hydroxyethane diphosphoric acid | — | 0.17 |
| NMP | 4 | — |
| initial water | 50 | 50 |
| No. 2 agent | | |
| composition blended in hair coloring | Example 83 10 | Example 83 10 |
| 60% hydroxyethane diphosphoric acid | 0.17 | 0.17 |
| dibasic sodium phosphate (12 hydrate) | 0.26 | 0.26 |
| 35% hydrogen peroxide | 17 | 16.5 |
| initial water | 70 | 60 |

(Preparation of Acidic Hair Coloring Materials)

Example 99

4 kg of additive compositions, which was the same one that are indicated as "1)" in Table 18, was added to 15 kg of the composition blended in hair coloring (Example 83), and this mixture was dissolved at 82–87° C. homogeneously. On the other hand, tar pigments (0.5 kg of orange No. 205, 0.3 kg of violet No. 401, and 0.3 kg of black No. 401,) and 0.2 kg of xanthan gum were added to about 60 kg of initial purified water and heated to 82–87° C. to prepare aqueous solution.

Then, the aforementioned homogeneous dissolved material was added to the above-mentioned hot aqueous solution with constant stirring and emulsified. After the emulsion was cooled down to the temperature of 50° C., 8 kg of additive compositions, which was the same one that are indicated as "6)" in Table 18, 5 kg of benzyl alcohol, 0.15 kg of parabens, perfumes were added, further, purified water (add water) was added so as to adjust the total weight to be 100 kg. Thus the acidic hair coloring material was prepared.

(Preparation of Waving Agents)

Example 100

Preparation of No. 1 Agent

The composition blended in waving agent (Example 83) was heated to the temperature of 80–85° C. and homogeneously dissolved and added to initial purified water that was previously heated to 80–85° C., stirred and emulsified. Then the emulsion was cooled down to the temperature of 45° C., 50% ammonium thioglycolate, strong ammonia solution and ammonium bicarbonate were added to the emulsion, further, purified water (add water) was added so as to adjust the total weight to be 100 kg. Thus No. 1 agent was prepared. The ingredients and contents (kg) are shown in Table 21.

Preparation of No. 2 Agents

The composition blended in waving agent (Example 83) was heated to the temperature of 80–85° C. and homogeneously dissolved, and then added to initial purified water that was previously heated to 80–85° C., stirred and emulsified. Then the emulsion was cooled down to the temperature of 45° C., sodium bromide was added to the emulsion, further, purified water (add water) was added so as to adjust the total weight to be 100 kg. Thus No. 2 agent was prepared. The ingredients and contents (kg) are shown in Table 21.

Example 101

Preparation of No. 1 Agents

No. 1 agent was prepared by the same process as Example 100.

Preparation of No. 2 Agents

To sodium bromate and lauryl trimethyl ammonium chloride, purified water was added so as to adjust the total weight to be 100 kg, and then mixed with stirring to prepare aqueous solution. Ingredients and contents (kg) are shown in Table 21.

TABLE 21

| ingredient (kg) | Example 100 | Example 101 |
| --- | --- | --- |
| No. 1 agent | | |
| composition blended in waving agent | Example 83 15 | Example 83 15 |
| 50% ammonium thioglycolate | 13 | 13 |
| strong ammonia solution | proper amount | proper amount |
| ammonium bicarbonate | proper amount | proper amount |
| initial water | 50 | 50 |
| No. 2 agent | | |
| composition blended in waving agent | Example 83 15 | — |
| sodium bromate | 8 | 8 |
| lauryl trimethyl ammonium chloride | — | 1 |
| initial water | 60 | — |

(Preparation of Finishing Agents)

Examples 102–104

To initial purified water, sodium hydroxide was added and heated to the temperature of 90–95° C. On the other hand, to the composition blended in finishing agent (Example 78) that was heated to the temperature of 90–95° C. and then dissolved homogeneously, polyoxyethylene hydrogenated castor oil, polyoxyethlene wax, dipropylene glycol (or propylene glycol), and parabens were added. Next methyl polysiloxane and isononyl isononanoate were added and dispersed.

Then, the dispersion was added to the above-mentioned alkaline aqueous solution with constant stirring and emulsified. After the emulsion was cooled down to the temperature of 45° C. with constant stirring, perfumes was added. And finally, purified water (add water) was added so as to adjust the total weight to be 100 kg, and then dissolved homogeneously. Thus, the finishing agent of the present invention was prepared. The ingredients and contents (kg) are shown in Table 22.

Example 105

To initial purified water, sodium hydroxide was added and heated to the temperature of 83–86° C. On the other hand, the composition blended in finishing agent Example 79) was heated to the temperature of 83–86° C. and then dissolved homogeneously, and then added to the above-mentioned alkaline aqueous solution with constant stirring and emulsified.

After the emulsion was cooled down to the temperature of 45° C. with constant stirring, purified water (add water) was added so as to adjust the total weight to be 100 kg, and then dissolved homogeneously. Thus, the finishing agent of the present invention was prepared. The ingredients and contents (kg) are shown in Table 22.

1)–6) in Tables 22 are indicating,
1) 10,000 cs,
2) 50% contents,
3) 25 EO,
4) 20 EO,
5) 30% contents,
6) 10% contents, (Preparation of the Compositions Blended in Hair Treating Agents)

Example 106

11.67 kg of lipophilic glyceryl monostearate, 8.75 kg of cetanol, 8.33 kg of behenyl alcohol, 18.75 kg of dipropylene glycol, 16.67 kg of polyoxyethylene (6 EO) cetyl ether, 2.08 kg of polyoxyethylene (40 EO) cetyl ether, 13.33 kg of stearic acid and 20.42 kg of candelilla wax were poured into a vessel and mixed, and the mixture was heated to the temperature of 80° C. and then stirred and dissolved completely. Thus, the compositions blended in a hair treating agent of the present invention was prepared.

(Preparation of Finishing Agents)

Examples 107–110

Initial purified water and TEA were mixed and heated to the temperature of 80–85° C. to prepare aqueous solution. On the other hand, the composition blended in finishing agent (Example 106), parabens (methyl parahydroxybenzoate, and/or propyl parahydroxybenzoate), and, if necessary, methyl polysiloxane, methylphenyl polysiloxane were mixed and heated to the temperature of 80–85° C., and then dissolved homogeneously.

The homogeneous dissolved material was added to the above-mentioned hot aqueous solution with constant stirring and emulsified. Then the emulsion was cooled down to the temperature of 45° C. with constant stirring. Next, proper amount of perfumes were added, and finally purified water (add water) was added so as to adjust the total weight to be 100 kg and then mixed homogeneously. Thus, the finishing agents of the present invention (Examples 107–110) were prepared. The ingredients and contents (kg) are shown in Table 23.

TABLE 22

| | Example | | | |
|---|---|---|---|---|
| ingredient (kg) | 102 | 103 | 104 | 105 |
| composition blended in finishing agent | Example 78 28 | Example 78 29.5 | Example 78 30 | Example 79 10 |
| polyoxyethylene hydrogenated castor oil | 1[3] | 0.5[3] | 0.5[4] | — |
| polyethylene wax | 3 | 4 | 4 | — |
| dipropylene glycol | 15 | 15 | — | — |
| propylene glycol | — | — | 15 | — |
| parabens | 0.15 | 0.15 | 0.4 | — |
| methyl polysiloxane[1] | 2.4 | 2.5 | 2 | — |
| isononyl isononanoate | 3 | 2 | 2.5 | — |
| sodium hydroxide | 1.2[5] | 1.2[5] | 1.2[5] | 0.6[6] |
| lactic acid[2] | 2 | 2 | 4 | — |
| perfume | proper amount | proper amount | proper amount | — |
| initial water | 40 | 40 | 40 | 70 |

TABLE 23

| ingredient (kg) | Example | | | |
|---|---|---|---|---|
| | 107 | 108 | 109 | 110 |
| composition blended in finishing agent | Example106 24 | Example106 24 | Example106 24 | Example106 24 |
| methyl polysiloxane | — | 1[1)] | 2[1)] | 3[3)] |
| methylphenyl polysiloxane | — | 3[2)] | 2[2)] | 1[3)] |
| TEA | 0.4 | 0.4 | 0.4 | 0.4 |
| methyl parahydroxybenzoate | 0.2 | 0.2 | 0.2 | 0.2 |
| propyl parahydroxybenzoate | 0.1 | 0.1 | 0.1 | 0.1 |
| perfume | proper amount | proper amount | proper amount | proper amount |
| initial water | 70 | 70 | 70 | 70 |

1)–3) in Tables 23 are indicating,
1) 20 cs,
2) 14 cs,
3) 1000 cs.

(The Organoleptic Tests About Hair Treating Effects of the Hair Treating Agents)

Hair treatings were carried out to 50 monitors by the following methods. And the results of the organoleptic tests about hair treating effects (i. e. feel when used) of the hair treating agents were obtained. The results of organoleptic tests were summarized in Table 24.

The Method for Hair Treating with Hair Conditioners

After ordinary shampoo, a specimen of each hair conditioners Examples 86–90) was applied to hair and spread by combing, and then rinsed and dried using a dryer.

In a Case of Colorings Rinses

After shampoo, a specimen of each hair conditioners (Examples 91–96) was applied to hair and then rinsed and dried using a dryer. Further, this treatment was repeated several times.

The Method for Hair Treating with Hair Colorings

No. 1 agents and No. 2 agents of the hair colorings (Example 97 and 98) were mixed (the wt. % ratio of No. 1 agents to No. 2 agents was 1:1). This mixture was applied to hair and left for 30 minutes at room temperature. Then, the hair was rinsed and dried using a dryer.

In a Case of Acidic Hair Coloring Materials

The acidic hair coloring materials (Example 99) was applied to hair and left for 15 minutes at 45° C. Then, the hair was rinsed. After shampoo, the hair was rinsed and dried using a dryer.

The Method for Hair Treating with Waving Agents

In a Case of Straight Type Permanent Wave

No. 1 agents of the waving agents Example 100) were coated to hair and spread by combing and the hair was formed to the straight shape. Then, the hair was left for 10 minutes. After that, No. 2 agents was coated to hair and spread by combing. Finally, rinsed and dried using a dryer.

In a Case of Curling Type Permanent Wave

No. 1 agents of the waving agents (Example 101) was coated to hair and spread by combing, and the hair was wound to a rod and left for 7 minutes at room temperature. Then No. 2 agents was coated by an applicator and left for 7 minutes. Repeatedly, No. 2 agents was coated by an applicator and left for 7 minutes. Next, the rod was removed, and the hair was rinsed and dried using a dryer.

The Method for Hair Treating with Finishing Agents

The finishing agents (Example 102–105, 107–110) was coated to hair and spread.

TABLE 24

| hair treating agent (Example) | feel when used | | | | | | | | | | |
|---|---|---|---|---|---|---|---|---|---|---|---|
| | slippery feel | soft feel | moist feel | smooth combing | rustle feeling | setting ability | well spread of cream | no liquid dropping | free of stickiness | less occurrence of flaking | vanishing ability |
| 86 | ⊚ | ⊚ | ⊚ | ○ | Δ | — | ○ | — | — | — | — |
| 87 | ⊚ | ⊚ | ○ | ○ | ⊚ | — | ○ | — | — | — | — |
| 88 | ⊚ | ⊚ | ○ | ○ | ○ | — | ○ | — | — | — | — |
| 89 | ⊚ | ⊚ | ⊚ | ○ | Δ | — | ○ | — | — | — | — |
| 90 | ○ | Δ | ○ | ○ | ○ | — | ○ | — | — | — | — |
| 91 | Δ | ○ | ○ | Δ | Δ | — | Δ | — | — | — | — |
| 92 | Δ | ○ | ○ | Δ | Δ | — | Δ | — | — | — | — |
| 93 | Δ | ○ | ○ | Δ | Δ | — | Δ | — | — | — | — |
| 94 | Δ | ○ | ○ | ○ | Δ | — | Δ | — | — | — | — |
| 95 | Δ | ○ | ○ | ○ | Δ | — | Δ | — | — | — | — |
| 96 | Δ | ○ | ○ | ○ | Δ | — | Δ | — | — | — | — |
| 97 | Δ | Δ | ○ | ○ | ○ | — | ○ | ⊚ | — | — | — |
| 98 | Δ | Δ | ○ | ○ | ○ | — | ○ | ⊚ | — | — | — |
| 99 | Δ | ○ | Δ | ⊚ | Δ | — | ⊚ | ⊚ | — | — | — |
| 100 | Δ | ○ | ○ | Δ | Δ | ○ | ○ | ⊚ | — | — | — |
| 101 | Δ | ○ | ○ | Δ | Δ | ○ | ○ | ⊚ | — | — | — |
| 102 | — | Δ | ○ | ○ | Δ | ⊚ | ⊚ | — | ⊚ | — | — |
| 103 | — | Δ | ○ | ○ | Δ | ⊚ | ⊚ | — | ⊚ | — | — |
| 104 | — | Δ | ○ | ○ | Δ | ⊚ | ⊚ | — | ⊚ | — | — |
| 105 | — | Δ | Δ | ○ | Δ | ○ | ○ | — | ○ | — | — |
| 107 | — | Δ | ○ | Δ | ○ | ⊚ | ⊚ | — | ○ | ○ | Δ |
| 108 | — | Δ | ⊚ | Δ | ○ | ⊚ | ⊚ | — | ○ | ⊚ | ⊚ |
| 109 | — | Δ | ⊚ | Δ | ○ | ⊚ | ⊚ | — | ○ | ⊚ | ⊚ |
| 110 | — | Δ | ⊚ | Δ | ○ | ⊚ | ⊚ | — | ○ | ⊚ | ⊚ |

In Table 24, ⊚ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as slippery feel, soft feel, moist feel, smooth combing, rustle feeling, setting ability, well spread of cream, no liquid dropping, no flafing, vanishing ability etc. Further, in the preparation process of hair treating agent since it is possible by using the compositions blended in a hair treating agents of the present invention to blend esters, alcohols, nonionic surfactants and fatty acids etc. at a time, the production process may be remarkably simplified.

Example of the Fifth Embodiment

The fifth embodiment of the present invention is illustrated more concretely according to the Examples.

(Preparation of the Compositions Blended in Hair Treating Agents)

Examples 111–130

The amounts (kg) shown in Tables 25–27 of ingredients were poured into a vessel and mixed, and the mixture was heated to the temperature shown in Tables 25–27, then stirred and dissolved completely. Thus, the compositions blended in a hair treating agents (Examples 111–130) of the present invention were prepared.

TABLE 25

| | Examplele | | | | | | |
|---|---|---|---|---|---|---|---|
| | 111 | 112 | 113 | 114 | 115 | 116 | 117 |
| | heating temp (° C.) | | | | | | |
| ingredient (kg) | 80 | 90 | 80 | 85 | 85 | 80 | 85 |
| ethylene glycol monostearate | — | — | — | — | — | 1.1 | — |
| ethylene glycol distearate | — | — | — | — | — | 4 | — |
| polyethylene glycol distearate[1] | — | — | — | — | — | — | — |
| neopentyl glycol dicaprate | — | — | — | 5 | — | — | — |
| lipophilic glyceryl monostearate | — | 5 | — | — | 7 | 7 | 5.5 |
| lipophilic glyceryl monooleate | — | — | — | — | — | — | 3.5 |
| cetyl octanoate | — | — | 13 | — | — | — | — |
| hexyl laurate | — | — | — | — | — | — | — |
| isopropyl myristate | 17 | — | 14 | 10 | — | — | 3.5 |
| isopropyl palmitate | 17 | — | — | — | — | — | — |
| diisopropyl adipate | — | — | — | — | — | — | 1.5 |
| cetyl lactate | — | — | — | 10 | — | — | — |
| lanolin fatty acid isopropyl ester | — | — | — | — | — | — | — |
| cetanol | 17 | — | 21 | 37 | 51 | 45 | 42 |
| stearyl alcohol | — | — | — | — | — | — | — |
| oleyl alcohol | 8 | — | — | — | 10 | — | — |
| octyldodecanol | — | 15 | 12 | — | — | — | — |
| behenyl alcohol | — | — | — | — | — | — | — |
| 1,3-butylene glycol | — | — | — | — | — | 7 | — |
| dipropylene glycol | — | — | — | — | — | — | 13.5 |
| glycerin | — | — | — | 21 | — | — | — |
| cetostearyl alcohol | — | 45 | — | — | — | — | — |
| lanolin alcohol | — | — | — | — | — | — | — |
| phytosterol | — | 2.2 | — | — | — | — | — |
| lauryl trimethyl ammonium bromide[2] | — | 5 | — | — | — | — | — |
| stearyl trimethyl ammonium chroride | — | — | 15[7] | 11[7] | — | 4[7] | 3.5[7] |
| cetyl trimethyl ammonium chloride[3] | — | — | — | — | — | — | — |
| cetyl trimethyl ammonium bromide[3] | 21 | — | — | — | — | — | — |
| behenyl trimethyl ammonium chloride[4] | — | 15 | — | 6 | 22 | 15 | 13.5 |
| lanolin | 4 | — | 17 | — | — | — | — |
| hard lanolin | — | — | — | — | — | — | — |
| hydrogenated oil | — | 10.5 | — | — | — | — | — |
| mink oil | — | — | — | — | — | — | — |
| olive oil | — | — | — | — | 10 | — | 10 |
| hydrogenated jojoba oil | — | — | — | — | — | — | — |
| hydrogenated castor oil | — | — | — | — | — | — | — |
| safflower oil | — | — | — | — | — | 12 | — |
| stearic acid | — | — | — | — | — | — | — |
| isostearic acid | — | — | — | — | — | — | — |
| vegetable squalane | — | 2.2 | — | — | — | — | — |
| paraffin | — | — | — | — | — | 4 | 3.5 |
| liquid petrolatum | — | — | — | — | — | — | — |
| vaseline | — | — | — | — | — | — | — |
| carnauba wax | — | — | — | — | — | — | — |
| beeswax | 8 | — | — | — | — | — | — |
| stearyl dimethyl glycine[5] | — | — | 2.95 | — | — | — | — |
| disodium edetate | — | — | 0.05 | — | — | — | — |
| γ-orizanol | — | 0.1 | — | — | — | — | — |
| dibutylhydroxytoluene | — | — | — | — | — | 0.1 | — |
| polyoxypropylene butyl ether[6] | 8 | — | 5 | — | — | — | — |
| methylphenyl polysiloxane | — | — | — | — | — | 0.8 | — |

TABLE 26

| ingredient (kg) | Example 118 | 119 | 120 | 121 | 122 | 123 | 124 |
|---|---|---|---|---|---|---|---|
| heating temp (° C.) | 80 | 80 | 80 | 80 | 80 | 80 | 80 |
| ethylene glycol monostearate | — | — | — | — | — | — | — |
| ethylene glycol distearate | — | — | — | — | — | — | — |
| polyethylene glycol distearate[1] | — | — | — | — | — | — | — |
| neopentyl glycol dicaprate | — | — | — | — | — | — | — |
| lipophilic glyceryl monostearate | — | 7 | — | 3 | 4 | 50 | 19 |
| lipophilic glyceryl monooleate | — | — | — | — | — | — | — |
| cetyl octanoate | — | — | — | — | — | — | — |
| hexyl laurate | — | — | — | — | — | — | 9 |
| isopropyl myristate | 6 | 3 | 28.65 | 26.95 | 24.95 | — | — |
| isopropyl palmitate | 2 | 5 | — | — | — | — | — |
| diisopropyl adipate | — | 3 | — | — | — | — | — |
| cetyl lactate | — | — | — | — | — | — | — |
| lanolin fatty acid isopropyl ester | — | — | — | — | — | — | — |
| cetanol | 35 | 19 | 15 | 20 | 12 | — | — |
| stearyl alcohol | — | — | — | — | 10 | 18 | 15 |
| oleyl alcohol | — | 5 | — | 4 | 4 | — | — |
| octyldodecanol | — | — | — | — | — | — | — |
| behenyl alcohol | 10 | — | — | — | — | — | — |
| 1,3-butylene glycol | — | — | — | — | — | — | — |
| dipropylene glycol | — | 9 | — | — | — | — | — |
| glycerin | — | — | — | — | — | — | — |
| cetostearyl alcohol | — | — | — | — | — | — | — |
| lanolin alcohol | — | — | 0.3 | — | — | — | — |
| phytosterol | — | — | — | — | — | — | — |
| lauryl trimethyl ammonium bromide[2] | — | — | — | — | — | — | — |
| stearyl trimethyl ammonium chloride | 46[7] | — | — | — | — | — | 15[7] |
| cetyl trimethyl ammonium chloride[3] | — | 9 | — | 26 | 19 | 32 | 35 |
| cetyl trimethyl ammonium bromide[3] | — | 3 | 24 | — | — | — | — |
| behenyl trimethyl ammonium chloride[4] | — | — | — | — | 6 | — | — |
| lanolin | — | — | — | 2 | 2 | — | — |
| hard lanolin | — | — | — | — | — | — | — |
| hydrogenated oil | — | 17 | 2 | 2 | — | — | — |
| mink oil | 1 | — | — | — | — | — | — |
| olive oil | — | — | 4 | 3 | 4 | — | — |
| hydrogenated jojoba oil | — | — | — | — | — | — | — |
| hydrogenated castor oil | — | — | — | — | — | — | — |
| safflower oil | — | — | — | — | — | — | — |
| stearic acid | — | — | 5 | — | — | — | 4 |
| isostearic acid | — | — | — | — | — | — | — |
| vegetable squalane | — | — | — | — | — | — | — |
| paraffin | — | 17 | — | — | — | — | — |
| liquid petrolatum | — | 3 | — | — | — | — | — |
| vaseline | — | — | 7 | 5 | 6 | — | — |
| carnauba wax | — | — | — | — | — | — | — |
| beeswax | — | — | — | — | — | — | 3 |
| stearyl dimethyl glycine[5] | — | — | — | — | — | — | — |
| disodium edetate | — | — | 0.05 | 0.05 | 0.05 | — | — |
| γ-orizanol | — | — | — | — | — | — | — |
| dibutylhydroxytoluene | — | — | — | — | — | — | — |
| polyoxypropylene butyl ether[6] | — | — | 14 | 8 | 8 | — | — |
| methylphenyl polysiloxane | — | — | — | — | — | — | — |

TABLE 27

| ingredient (kg) | Example 125 | 126 | 127 | 128 | 129 | 130 |
|---|---|---|---|---|---|---|
| heating temp (° C.) | 80 | 85 | 85 | 85 | 85 | 80 |
| ethylene glycol monostearate | — | — | — | — | — | — |
| ethylene glycol distearate | — | — | — | — | — | — |
| polyethylene glycol distearate[1] | — | — | — | — | — | 24 |
| neopentyl glycol dicaprate | — | — | — | — | — | — |
| lipophilic glyceryl monostearate | 17 | 13 | 5 | 6 | 7 | — |
| lipophilic glyceryl monooleate | — | — | — | — | — | — |
| cetyl octanoate | — | — | — | — | — | — |
| hexyl laurate | — | — | — | — | — | — |
| isopropyl myristate | 9 | 14 | — | — | 5 | — |
| isopropyl palmitate | — | — | — | 1 | — | — |
| diisopropyl adipate | — | — | — | — | — | — |
| cetyl lactate | — | — | — | — | — | — |

TABLE 27-continued

| ingredient (kg) | Examplele | | | | | |
|---|---|---|---|---|---|---|
| | 125 | 126 | 127 | 128 | 129 | 130 |
| | heating temp (° C.) | | | | | |
| | 80 | 85 | 85 | 85 | 85 | 80 |
| lanolin fatty acid isopropyl ester | — | — | — | 8 | — | — |
| cetanol | — | 30 | 60 | — | — | — |
| stearyl alcohol | 35 | — | — | — | — | 5 |
| oleyl alcohol | — | — | — | — | — | — |
| octyldodecanol | — | — | — | — | — | — |
| behenyl alcohol | — | — | — | 24 | — | 17 |
| 1,3-butylene glycol | — | — | — | — | — | — |
| dipropylene glycol | — | — | — | — | — | — |
| glycerin | — | — | — | — | — | — |
| cetostearyl alcohol | — | — | — | 24 | 52 | — |
| lanolin alcohol | — | — | — | — | — | — |
| phytosterol | — | — | — | — | — | — |
| lauryl trimethyl ammonium bromide[2] | — | — | — | — | — | — |
| stearyl trimethyl ammonium chroride | — | — | 26[7] | 26[7] | 28[3] | — |
| cetyl trimethyl ammonium chloride[3] | 35 | 16 | 3 | — | — | 15 |
| cetyl trimethyl ammonium bromide[3] | — | — | — | — | — | — |
| behenyl trimethyl ammonium chloride[4] | — | 10 | — | 8 | — | — |
| lanolin | — | — | 1 | — | — | — |
| hard lanolin | 3.95 | — | — | — | — | — |
| hydrogenated oil | — | — | — | — | — | — |
| mink oil | — | — | — | — | — | — |
| olive oil | — | 10 | — | — | 5 | — |
| hydrogenated jojoba oil | — | — | — | 3 | — | — |
| hydrogenated castor oil | — | — | — | — | 3 | — |
| safflower oil | — | — | — | — | — | — |
| stearic acid | — | — | — | — | — | — |
| isostearic acid | — | — | — | — | — | 39 |
| vegetable squalane | — | — | — | — | — | — |
| paraffin | — | — | — | — | — | — |
| liquid petrolatum | — | — | — | — | — | — |
| vaseline | — | — | — | — | — | — |
| carnauba wax | — | 7 | — | — | — | — |
| beeswax | — | — | 5 | — | — | — |
| stearyl dimethyl glycine[5] | — | — | — | — | — | — |
| disodium edetate | 0.05 | — | — | — | — | — |
| γ-orizanol | — | — | — | — | — | — |
| dibutylhydroxytoluene | — | — | — | — | — | — |
| polyoxypropylene butyl ether[6] | — | — | — | — | — | — |
| methylphenyl polysiloxane | — | — | — | — | — | — |

1)–7) in Table 2527 are indicating, 1) 8 EO,
2) containing 32 wt. % of water+18 wt. % of IPA (isopropanol),
3) containing 30 wt. % of ethanol,
4) containing 20 wt. % of IPA,
5) 26 wt. % aqueous solution,
6) 40 PO,
7) containing 40 wt. % of IPA.

(Preparation of Hair Conditioners)

Examples 131–145

Initial purified water was heated to the temperature shown in Table 28 and Table 29. Next, glycerin, disodium edetate. if necessary, was added to this, and dissolved. On the other hand, the composition blended in hair conditioner obtained above (Examples 111, 114–117, 119, 121, 122, 126–128) was heated to the temperature shown in Table 28 and Table 29 and then dissolved homogeneously. Further, to this, additive composition, parabens and dibutylhydroxytoluene, if necessary, were added to prepare homogeneous dissolved material.

The homogeneous dissolved material was added to the above-mentioned hot water (or hot aqueous solution) with constant stirring and emulsified. Then the emulsion was cooled down to the temperature of 40–55° C. with constant stirring. Then, additives, if necessary, such as perfumes, PPT, pigments, PCA soda, citric acid, pH adjustor were added, then purified water (add water) was added so as to adjust the total weight to be 100 kg and then mixed homogeneously. Thus, the hair conditioners of the present invention (Examples 131–145) were prepared. The ingredients and contents (kg) are shown in Table 28 and Table 29.

TABLE 28

| ingredient (kg) | Examplele | | | | | | | |
|---|---|---|---|---|---|---|---|---|
| | 131 | 132 | 133 | 134 | 135 | 136 | 137 | 138 |
| | heating temp (° C.) | | | | | | | |
| | 80~85 | 85~90 | 85~90 | 83~86 | 83~86 | 83~86 | 83~86 | 83~86 |
| composition blended in hair conditioner | Example 111 24 | Example 114 15 | Example 114 15 | Example 115 15 | Example 116 14 | Example 117 15 | Example 117 12 | Example 119 7 |
| initial purified water | 60 | 80 | 80 | 80 | 80 | 70 | 70 | 60 |
| additive composition | — | 1.5[1] | 1.5[2] | — | — | — | — | 0.5[4] |
| parabens | 0.15 | 0.2 | 0.2 | 0.2 | — | 0.15 | 0.15 | 0.15 |
| perfume | proper amount | proper amount | proper amount | proper amount | proper amount | proper amount | proper amount | proper amount |
| PPT | — | — | — | — | — | 3.3[3] | proper amount | 3 |
| pigment | — | — | — | — | — | — | — | — |
| glycerin | — | — | — | 3 | — | 2 | 2 | — |
| PCA soda | — | — | — | — | — | — | 3 | — |

TABLE 28-continued

| | Examplele | | | | | | | |
|---|---|---|---|---|---|---|---|---|
| | 131 | 132 | 133 | 134 | 135 | 136 | 137 | 138 |
| | | | | heating temp (° C.) | | | | |
| ingredient (kg) | 80~85 | 85~90 | 85~90 | 83~86 | 83~86 | 83~86 | 83~86 | 83~86 |
| dibutylhydroxytoluene | — | — | — | — | 0.04 | — | — | — |
| disodium edetate | — | — | — | — | 0.1 | — | — | — |
| lactic acid | — | 0.1 | 0.1 | — | — | — | — | — |
| citric acid | — | — | — | — | 0.04 | — | — | — |
| pH adjustor | — | — | — | — | — | — | — | — |
| usefull aqueous material | — | — | — | — | — | — | — | proper amount |

TABLE 29

| | Examplele | | | | | | |
|---|---|---|---|---|---|---|---|
| | 139 | 140 | 141 | 142 | 143 | 144 | 145 |
| | | | | heating temp (°C) | | | |
| ingredient (kg) | 83~86 | 85~90 | 85~90 | 80~85 | 80~85 | 82~85 | 83~88 |
| composition blended in hair conditioner | Example 119 14 | Example 121 10 | Example 122 10 | Example 126 8 | Example 126 12 | Example 127 10 | Example128 10 |
| initial purified water | 70 | 80 | 80 | 60 | 70 | 80 | 80 |
| additive composition | 0.5[4] | — | — | — | — | — | — |
| parabens | 0.15 | — | — | 0.15 | 0.15 | — | 0.15 |
| perfume | proper amount | proper amount | proper amount | proper amount | proper amount | proper amount | proper amount |
| PPT | 6 | proper amount | proper amount | — | — | — | — |
| pigment | — | — | — | proper amount | proper amount | proper amount | — |
| glycerin | — | — | — | — | — | — | — |
| PCA soda | — | — | — | 10 | 3 | — | — |
| dibutylhydroxytoluene | — | — | — | — | — | — | — |
| disodium edetate | — | — | — | — | — | — | — |
| lactic acid | — | — | — | — | — | — | — |
| citric acid | — | 0.2 | 0.2 | — | — | — | 0.2 |
| pH adjustor | — | proper amount | proper amount | — | — | — | — |
| usefull aqueous material | proper amount | — | — | — | — | — | — |

1)–4) in Table 28 and Table 29 are indicating,
1) ingredients (wt. %); dipentaerythritol fatty ester [the full esters prepared from dipentaerythritol and mixed fatty acid (12-hydroxystearic acid:stearic acid:rosin= 4:1.5:0.5)] (50), triglyceryl cocoate (30), isopropyl palmitate (10), diisobutyl adipate (10),
2) ingredients (wt. %); dimethylsiloxane·methylstearoxysiloxane copolymer (50), diisopropyl adipate (25), ), isoobutyl adipate (25),
3) hydrolyzed animal protein aqueous solution (30 wt. %),
4) animal fats and oils, (Preparation of Oxidizing Hair Coloring Agents)

Examples 146 and 147

Preparation of No. 1 Agents

To initial purified water that was heated to the temperature of 80–85° C., dye intermediates (resorcinol, p-phenylene diamine, m-aminophenol, p-aminophenol), antioxidant, and, if necessary, NMP were added to prepare aqueous solution.

On the other hand, to the composition blended in hair coloring (Example 118), polyoxyethylene cetyl ether and cetanol were added and heated to the temperature of 80–85° C., and then dissolved homogeneously. Then, the homogeneous dissolved material was added to the above-mentioned hot aqueous solution with constant stirring and emulsified.

After the emulsion was cooled down to the temperature of 50–55° C. with constant stirring, additives, if necessary, such as MEA, strong ammonium solution, EDTA, 60% 1-hydroxyethane-1,1-diphosphonic acid were added, and finally, purified water (add water) was added so as to adjust the total weight to be 100 kg. Thus No. 1 agent was prepared. The ingredients and contents (kg) are shown in Table 30.

Preparation of No. 2 Agents

Polyoxyethylene cetyl ether and cetanol were added to the composition blended in hair coloring (Example 118) and dissolved homogeneously at 80–85° C. Then, the homogeneous dissolved material was added with constant stirring to initial purified water that was heated to the temperature of 80–85° C., and then emulsified.

Then the emulsion was cooled down to the temperature of 45° C. with constant stirring, 60% hydroxyethane diphosphonic acid, dibasic sodium phosphate (12 hydrate) were added, further 35 wt. % hydrogen peroxide aqueous solution was added. Finally, purified water (add water) was added so as to adjust the total weight to be 100 kg. Thus No. 2 agent was prepared. Ingredients and contents (kg) are shown in Table 30.

TABLE 30

| ingredient (kg) | Examplele 146 | Examplele 147 |
|---|---|---|
| No. 1 agent | | |
| composition blended in hair coloring | Example 118 16 | Example 118 16 |
| polyoxyethylene cetyl ether[1] | 1 | 1 |
| cetanol | 3 | 3 |
| initial purified water | 50 | 50 |
| dye intermediate | proper amount | proper amount |
| antioxidant | proper amount | proper amount |
| NMP | 4 | — |
| MEA | proper amount | — |
| strong ammonia solution | — | 4 |
| EDTA | 0.2 | — |
| 60% hydroxyethane diphosphoric acid | — | 0.17 |
| No. 2 agent | | |
| composition blended in hair coloring | Example 118 16 | Example 118 16 |
| polyoxyethylene cetyl ether[1] | 1 | 1 |
| cetanol | 3 | 3 |
| initial purified water | 70 | 60 |
| 60% hydroxyethane diphosphoric acid | 0.17 | 0.17 |
| dibasic sodium phosphate (12 hydrate) | 0.26 | 0.26 |
| 35% hydrogen peroxide | 17 | 16.5 |

1) in Table 30 are indicating 40 EO.
(Preparation of Cationic Waving Agents)

Example 148

Preparation of No. 1 Agents

Polyoxyethylene cetyl ether and cetanol were added to the composition blended in waving agent (Example 118) and dissolved homogeneously at 80–85° C. Then, the homogeneous dissolved material was added with constant stirring to initial purified water that was heated to the temperature of 80–85° C., and then emulsified. Then the emulsion was cooled down to the temperature of 45° C. with constant stirring, 50% ammonium thioglycolate, strong ammonia solution and ammonium bicarbonate were added, further purified water (add water) was added so as to adjust the total weight to be 100 kg. Thus No. 1 agent was prepared. Ingredients and contents (kg) are shown in Table 31.

Preparation of No. 2 agents

Polyoxyethylene cetyl ether and cetanol were added to the composition blended in waving agent (Example 118) and dissolved homogeneously at 80–85° C. Then, the homogeneous dissolved material was added with constant stirring to initial purified water that was heated to the temperature of 80–85° C., and then emulsified. Then the emulsion was cooled down to the temperature of 45° C. with constant stirring, sodium bromate was added, further purified water (add water) was added so as to adjust the total weight to be 100 kg. Thus No. 2 agent was prepared. Ingredients and contents (kg) are shown in Table 31.

Example 149

Preparation of No. 1 Agent

No. 1 agents was prepared by the same process as Example 148.

Preparation of No. 2 Agent

To sodium bromate and lauryl trimethyl ammonium chloride, purified water was added so as to adjust the total weight to be 100 kg, and then mixed with stirring to prepare aqueous solution. Ingredients and contents (kg) are shown in Table 31.

TABLE 31

| ingredient (kg) | Examplele 148 | Examplele 149 |
|---|---|---|
| No. 1 agent | | |
| composition blended in waving agent | Example 118 16 | Example 118 16 |
| polyoxyethylene cetyl ether[1] | 1 | 1 |
| cetanol | 3 | 3 |
| initial purified water | 50 | 50 |
| 50% ammonium thioglycolate | 13 | 13 |
| strong ammonia solution | proper amount | proper amount |
| ammonium bicarbonate | proper amount | proper amount |
| No. 2 agent | | |
| composition blended in waving agent | Example 118 16 | — |
| polyoxyethylene cetyl ether[1] | 1 | — |
| cetanol | 3 | — |
| sodium bromate | 8 | 8 |
| lauryl trimethyl ammonium chloride | — | 1 |
| initial purified water | 60 | — |

1) in Table 31 are indicating 40 EO.
(Preparation of Finishing Agents)

Example 150

About 95 kg of initial purified water was heated to the temperature of 83–86° C. On the other hand, to 5 kg of the composition blended in finishing agent (Example 125), proper amount of parabens were added and heated to the temperature of 83–86° C., and then dissolved homogeneously. Then, the homogeneous dissolved material was added to the above-mentioned hot water with constant stirring, and then emulsified.

After the emulsion was cooled down to the temperature of 45–50° C. with constant stirring, purified water (add water) was added so as to adjust the total weight to be 100 kg. Thus, the finishing agent of the present invention was prepared.
(Preparation of Color Fixing Agent)

Example 151

About 55 kg of initial purified water was heated to the temperature of 80–85° C. On the other hand, to 15 kg of the composition blended in color fixing agent (Example 115) and 0.1 kg of parabens were mixed and heated to the temperature of 80–85° C., and then dissolved homogeneously. Then, the homogeneous dissolved material was added to the above-mentioned hot water with constant stirring, and then emulsified.

After the emulsion was cooled down to the temperature of about 50° C. with constant stirring, aqueous compositions (25 kg of purified water, 2 kg of "HAIRROL TC1000" [trade name, Sanyo-Kasei co.], 0.4 kg of 85% phosphoric acid, 1 kg of 70% glycolic acid), and perfumes was added, and finally, purified water (add water) was added so as to adjust the total weight to be 100 kg. Thus, the color fixing agent of the present invention was prepared.
(The Organoleptic Tests About Hair Treating Effects of the Hair Treating Agents)

Hair treatings were carried out to 50 monitors by the following methods. And the results of the organoleptic tests about hair treating effects (i. e. feel when used) of the hair treating agents were obtained. The results of organoleptic tests were summarized in Table 32.

The Method for Hair Treating with Hair Conditioners

After ordinary shampoo, a specimen of each hair conditioners (Examples 131–145) was applied to hair and spread by combing, and then rinsed and dried using a dryer.

The Method for Hair Treating with Hair Colorings

No. 1 agents and No. 2 agents of the hair colorings (Example 146 and 147) were mixed (the wt. % ratio of No. 1 agents to No. 2 agents was 1:1). This mixture was applied to hair and left for 30 minutes at room temperature. Then, the hair was rinsed and dried using a dryer.

The Method for Hair Treating with Waving Agents

In a Case of Straight Type Permanent Wave

No. 1 agents of the waving agents (Example 148) were coated to hair and spread by combing and the hair was formed to the straight shape. Then, the hair was left for 10 minutes. After that, No. 2 agents was coated to hair and spread by combing, further left for 10 minutes. Finally, rinsed and dried using a dryer.

In a Case of Curling Type Permanent Wave

No. 1 agents of the waving agents (Example 149) was coated to hair and spread by combing, and the hair was wound to a rod and left for 7 minutes at room temperature. Then No. 2 agents was coated by an applicator and left for 7 minutes. Repeatedly, No. 2 agents was coated by an applicator and left for 7 minutes. Next, the rod was removed, and the hair was rinsed and dried using a dryer.

The Method for Hair Treating with Finishing Agents

The finishing agents (Example 150) was coated to hair and spread.

The Method for Hair Treating with Color Fixing Agents

Hair colorings on the market was coated to hair and spread by combing. Next, the hair was left for 15 minutes at 45° C., and then rinsed and dried using a dryer. Then, hair treating with the color fixing agents (Example 151) was carried out by the same way to hair treating with an ordinary rinses. In the treating, the hair was rinsed and dried using a dryer after coated with the color fixing agents.

In Table 32, ⊚ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as supple, slightly oily feel, soft feel, moist feel, no tangle and no squeak, smooth feel (smooth combing,), wet feel, rustle feeling, keeping ability of hair styling, preventive ability for fading dye, Further, in the preparation process of hair treating agent since it is possible by using the compositions blended in a hair treating agents of the present invention to blend esters, alcohols, and cationic surfactants at a time, the production process may be remarkably simplified.

Example of the Sixth Embodiment

The sixth embodiment of the present invention is illustrated more concretely according to the Examples.

(Preparation of the Compositions Blended in Hair Treating Agents)

Examples 152–165

The amount (kg) shown in Table 33 and Table 34 of ingredients were poured into a vessel and mixed, and the mixture was heated to the temperature shown in Table 33, then stirred and dissolved completely. Thus, the compositions blended in a hair treating agents (Examples 152–165) of the present invention were prepared.

TABLE 32

| hair treating agent (Ex) | feel when used | | | | | | | | | | |
|---|---|---|---|---|---|---|---|---|---|---|---|
| | supple | slightly oily feel | soft feel | moist feel | smooth combing | no tangles and no squeak | smooth feel | moisture | rustle feeling | keeping ability of hair styling | prevention of dye decolorization |
| 131 | ⊚ | Δ | ⊚ | ⊚ | ○ | ⊚ | Δ | ⊚ | Δ | — | — |
| 132 | ⊚ | Δ | ⊚ | ⊚ | ○ | ○ | ○ | ⊚ | Δ | — | — |
| 133 | ⊚ | Δ | ⊚ | ⊚ | ○ | ⊚ | ⊚ | ⊚ | Δ | — | — |
| 134 | ⊚ | ⊚ | ○ | ⊚ | ○ | ○ | Δ | Δ | Δ | — | — |
| 135 | ○ | Δ | Δ | ⊚ | ○ | ○ | ○ | Δ | ⊚ | — | — |
| 136 | ⊚ | ⊚ | ⊚ | ⊚ | Δ | Δ | Δ | ○ | Δ | — | — |
| 137 | ⊚ | ⊚ | ⊚ | ⊚ | Δ | Δ | Δ | ○ | Δ | — | — |
| 138 | ⊚ | Δ | ⊚ | ⊚ | ○ | ⊚ | ○ | ⊚ | Δ | — | — |
| 139 | ⊚ | Δ | ⊚ | ⊚ | ○ | ⊚ | ○ | ⊚ | Δ | — | — |
| 140 | ⊚ | ○ | ○ | ⊚ | ⊚ | ○ | Δ | ⊚ | Δ | — | — |
| 141 | ⊚ | ○ | ○ | ⊚ | ⊚ | ○ | Δ | ⊚ | Δ | — | — |
| 142 | Δ | Δ | ⊚ | ⊚ | ○ | ⊚ | ⊚ | ○ | ⊚ | — | — |
| 143 | Δ | Δ | ⊚ | ⊚ | ○ | ○ | ⊚ | ○ | ⊚ | — | — |
| 144 | ⊚ | Δ | ○ | ○ | ⊚ | ○ | ○ | ○ | ⊚ | — | — |
| 145 | ○ | ○ | ⊚ | ⊚ | ○ | ○ | ⊚ | ⊚ | ⊚ | — | — |
| 146 | Δ | Δ | ○ | Δ | ○ | ⊚ | Δ | Δ | ○ | — | — |
| 147 | Δ | Δ | ○ | Δ | ○ | ⊚ | Δ | Δ | ○ | — | — |
| 148 | Δ | Δ | ○ | Δ | ○ | ⊚ | Δ | Δ | ○ | — | — |
| 149 | Δ | Δ | ○ | Δ | ○ | ⊚ | Δ | Δ | ○ | — | — |
| 150 | ○ | ⊚ | ○ | ⊚ | Δ | Δ | Δ | ○ | ○ | ⊚ | — |
| 151 | ○ | ⊚ | Δ | Δ | ○ | ○ | ○ | Δ | ○ | — | ⊚ |

TABLE 33

| | Example |
|---|---|
| | 152 | 153 | 154 | 155 | 156 | 157 | 158 | 159 | 160 | 161 | 162 | 163 | 164 | 165 |
| | heating temp (° C.) |
| ingredient (kg) | 85 | 85 | 80 | 85 | 70 | 85 | 85 | 80 | 85 | 80 | 80 | 80 | 80 | 90 |
| polyethylene glycol distearate | — | — | — | — | — | 6 | — | — | — | — | — | — | — | — |
| mono and diglyceryl oleate and stearate | — | — | — | — | — | — | — | — | — | — | — | — | 8 | — |
| lipophilic glyceryl monostearate | 1 | 5 | 10 | — | 14 | — | 9.7 | — | 10 | — | — | — | — | — |
| glyceryl cocoate | — | — | — | — | — | — | — | — | — | — | — | 4 | — | — |
| dipentaerythritol fatty acid ester[1] | — | — | — | — | — | 4 | — | — | — | — | — | — | — | — |
| hexyl laurate | — | — | — | — | 14 | — | — | — | — | — | — | — | — | — |
| isopropyl myristate | 6 | — | — | 15 | — | 6 | — | 10 | 10 | — | — | — | 5 | 6 |
| isopropyl palmitate | — | — | — | — | — | — | — | — | — | — | — | 13 | — | — |
| butyl stearate | — | — | — | — | — | — | — | — | — | — | 5 | — | — | — |
| octyl palmitate | — | — | — | — | — | — | — | — | — | — | — | 8 | — | — |
| diisostearyl malate | 1 | — | — | — | — | — | — | — | — | — | — | — | — | — |
| diisopropyl adipate | — | — | — | — | — | — | — | 5 | — | — | — | — | — | — |
| lauryl alcohol | — | — | — | — | — | — | — | 5 | — | — | — | — | — | — |
| isopropanol | — | — | — | — | — | — | 1.4 | — | — | — | — | — | — | — |
| cetanol | 34 | 30 | 50 | 31 | — | — | 9.7 | 61 | 39 | 60 | 33 | 50 | — | 18 |
| stearyl alcohol | — | 22 | — | — | 27 | — | — | — | — | — | — | — | — | — |
| oleyl alcohol | — | — | — | — | 1 | 0.4 | — | — | — | — | — | — | — | — |
| octyldodecanol | 21 | — | — | — | — | — | — | — | — | — | — | — | — | — |
| behenyl alcohol | — | 2 | — | — | — | — | — | — | — | — | — | — | — | — |
| side chain higher fatty alcohols (C32·C36) | — | — | — | — | — | — | 0.9 | — | — | — | — | — | — | — |
| propylene glycol | — | — | — | — | — | 13 | — | — | — | — | — | 4 | — | — |
| dipropylene glycol | — | — | — | — | — | — | 15.5 | — | — | — | — | — | — | — |
| 1,3-butylene glycol | — | — | — | — | — | — | 0.2 | — | — | — | — | — | — | — |
| glycerin | — | — | — | — | — | — | — | — | — | — | — | 17 | — | — |
| cetostearyl alcohol | — | — | — | — | — | — | — | — | — | — | — | — | 48 | — |
| lanolin alcohol | — | — | — | 0.1 | — | — | — | — | — | — | — | — | — | — |

TABLE 34

| | Example |
|---|---|
| ingredient (kg) | 152 | 153 | 154 | 155 | 156 | 157 | 158 | 159 | 160 | 161 | 162 | 163 | 164 | 165 |
| stearyl trimethyl ammonium chloride | — | 5[12] | — | 5[12] | — | — | — | — | — | — | 18[12] | 13[13] | — | — |
| cetyl trimethyl ammonium chloride[2] | 23 | 18 | — | — | 39 | — | — | 20 | 34 | 15 | — | — | 30 | 25 |
| cetyl trimethyl ammonium bromide[2] | — | — | — | — | — | 4 | — | — | — | — | — | — | — | — |
| behenyl trimethyl ammonium chloride[3] | — | — | — | — | — | — | — | — | 5 | — | — | — | — | — |
| distearyl dimethyl ammonium chloride[4] | — | — | — | 30.4 | — | — | — | — | — | — | — | — | — | — |
| dipolyoxyethylene oleyl methyl ammonium chloride[5],[18] | — | — | — | — | — | — | — | 5 | — | — | — | — | 5 | — |
| benzalkonium chloride[6] | — | — | 30 | — | — | — | — | — | — | — | — | — | — | — |
| cetyl pyridinium chloride[7] | — | — | — | — | — | — | 1.6 | — | — | — | — | — | — | — |
| polyoxyethylene lauryl ether[8] | — | — | — | — | — | — | — | 4 | — | 5 | — | — | — | — |
| polyoxyethylene cetyl ether | — | — | 5[14] | — | 2[15] | — | — | 2[14] | — | 17[15] | 13[15] | — | 18[16] |
| polyoxyethylene oleyl ether | 3[17] | — | — | 18[18] | — | — | 38.9[18] | — | — | — | — | — | 2[14] | — |
| polyoxyethylene nonylphenyl ether[9] | — | — | — | — | — | 28 | — | — | — | — | — | — | — | — |
| polyoxyethylene castor oil[10] | — | — | — | — | — | 11 | — | — | — | — | — | — | — | — |
| polyoxyethylene hydrogenated castor oil[11] | — | — | — | — | — | 17 | — | — | — | — | — | — | — | — |
| stearic acid monoethanolamide | — | — | — | 0.5 | — | — | — | — | — | — | — | — | — | — |
| coconut fatty acid monoethanolamide | — | 2 | — | — | — | — | — | — | — | — | — | — | 2 | — |
| sorbitan trioleate | — | — | — | — | — | 6 | — | — | — | — | — | — | — | — |
| dimethyl stearylamine | — | — | — | — | — | — | 5.8 | — | — | — | — | — | — | — |
| paraffin | — | — | 5 | — | — | — | 8.9 | — | — | 5 | 2 | 4 | — | 3 |
| liquid petrolatum | — | — | — | — | — | — | 0.9 | — | — | — | — | — | — | — |
| light liquid isoparaffin | — | — | — | — | — | — | — | — | — | — | — | 4 | — | — |
| ceresin | — | 15 | — | — | — | — | — | — | — | — | — | — | — | — |
| α-olefin oligomer | 1 | — | — | — | — | — | — | — | — | — | — | — | — | — |
| sodium lauryl sulfate | 3 | — | — | — | — | — | — | — | — | — | — | — | — | — |
| stearic acid | — | — | — | — | 4 | — | — | — | — | — | — | — | — | — |

TABLE 34-continued

| ingredient (kg) | Examplele | | | | | | | | | | | | | |
|---|---|---|---|---|---|---|---|---|---|---|---|---|---|---|
| | 152 | 153 | 154 | 155 | 156 | 157 | 158 | 159 | 160 | 161 | 162 | 163 | 164 | 165 |
| hard lanolin fatty acid | — | — | — | — | — | — | — | — | — | — | — | — | — | 30 |
| carnauba wax | — | 1 | — | — | — | — | — | — | — | — | — | — | — | — |
| lactic acid | — | — | — | — | — | — | 5.3 | — | — | — | — | — | — | — |
| methylphenyl polysiloxane | — | — | — | — | — | 4 | — | — | — | — | — | — | — | — |
| purified water | 7 | — | — | — | — | — | 0.8 | — | — | — | — | — | — | — |

1)–18) in Table 33 or Table 34 are indicating,
1) full esters prepared from dipentaerythritol and mixed fatty acid (12-hydroxystearic acid:stearic acid:rosin=4:15:0.5),
2) containing 30 wt % ethanol,
3) containing 20 wt. % IPA (isopropanol),
4) containing 25 wt. % mixture of IPA and water,
5) containing 25 wt. % IPA,
6) 50 wt. % aqueous solution,
7) containing 60 wt. % mixture of IPA and water,
8) 23 EO,
9) 3 EO,
10) 10 EO,
11) 20 EO,
12) containing 40 wt. % IPA,
13) containing 30 wt. % IPA,
14) 30 EO,
15) 40 EO,
16) 5 EO,
17) 8 EO,
18) 2 EO.

(Preparation of Hair Conditioners)

Examples 166–176

According to the ingredients and contents shown in Table 35 and Table 36, hair conditioners were prepared by following methods.

Initial purified water was heated to the temperature of 83–86° C. (Examples 166, 173–176) or 87–91° C. (Examples 167–172). And to this, glycerin, if necessary, was added and dissolved to prepare aqueous solution.

On the other hand, the composition blended in hair conditioner obtained above (examples 152, 153, 155, or 156) was heated to the temperature 83–86° C. (Examples 166, 169–176) or 87–91° C. (Examples 167, 168), and then dissolved homogeneously. Further, to this, silicones (or in Example 170 and 172, additive compositions instead of silicones), parabens and 1,3-butylene glycol, if necessary, were added and dissolved homogeneously.

The homogeneous dissolved material was added to the above-mentioned hot water with constant stirring and emulsified. Then the emulsion was cooled down to the temperature of 50° C. with constant stirring. And, additives, if necessary, PPT, perfumes, cationized cellulose, pigments, additive compositions (Example 176) were added. Finally, purified water (add water) was added so as to adjust the total weight to be 100 kg and then mixed homogeneously. Thus, the hair conditioners of the present invention (Examples 166–176) were prepared.

Example 177

After the composition blended in hair conditioner (Example 157) was heated to the temperature 85° C., and then dissolved homogeneously, additive compositions, isopropyl myristate, propylene glycol, proper amount of parabens, proper amount of perfumes were added and dissolved homogeneously, Finally, purified water (add water) was added so as to adjust the total weight to be 100 kg and then mixed homogeneously. Thus, the hair conditioner of the present invention was prepared. Ingredients and contents (kg) are shown in Table 36.

Example 178

After the composition blended in hair conditioner (Example 157) was heated to the temperature 85° C. and then dissolved homogeneously, lanolin amidopropyl ethyl dimethyl ammonium ethylsulfate, proper amount of parabens and proper amount of perfumes were added and dissolved homogeneously, Finally, purified water (add water) was added so as to adjust the total weight to be 100 kg and then mixed homogeneously. Thus, the hair conditioner of the present invention was prepared. Ingredients and contents (kg) are shown in Table 36.

Example 179

The compositions blended in hair conditioners (Example 158), that was heated to the temperature 83–86° C., was added with stirring to initial purified water that was previously heated to the temperature 83–86° C., and then emulsified. Then the emulsion was cooled down below the temperature of 40° C. with constant stirring, another additives shown in Table 36 were added, and then further, purified water (add water) was added so as to adjust the total weight to be 100 kg. Thus, the hair conditioner of the present invention was prepared. Ingredients and contents (kg) are shown in Table 36.

TABLE 35

| ingredient (kg) | Example 152 | | | | | | |
|---|---|---|---|---|---|---|---|
| | 166 | 167 | 168 | 169 | 170 | 171 | 172 |
| composition blended in hair conditioner | Example 152<br>15 | Example 153<br>6 | Example 153<br>15 | Example 153<br>6 | Example 153<br>6 | Example 153<br>15 | Example 153<br>15 |
| initial purified water | 60 | 40 | 40 | 40 | 40 | 40 | 40 |

TABLE 35-continued

| | Example 152 | | | | | | |
|---|---|---|---|---|---|---|---|
| ingredient (kg) | 166 | 167 | 168 | 169 | 170 | 171 | 172 |
| propylene glycol | — | — | — | — | — | — | — |
| 1,3-butylene glycol | — | — | — | — | — | — | — |
| glycerin | — | 2 | 2 | 2 | 2 | 2 | 2 |
| additive composition | — | — | — | — | 0.3[1)] | — | 1[1)] |
| parabens | 0.15 | — | — | 0.15 | 0.15 | 0.15 | 0.15 |
| PPT | — | — | — | proper amount | proper amount | proper amount | proper amount |
| pigment | — | — | — | — | — | — | — |
| perfume | — | proper amount | proper amount | proper amount | proper amount | proper amount | proper amount |
| methyl polysiloxane | — | — | — | 0.3 | — | 1 | — |
| malic acid | — | — | — | — | — | — | — |
| isopropyl myristate | — | — | — | — | — | — | — |
| cationized cellulose | — | — | — | — | — | — | — |
| lanolin amidopropyl ethyl dimethyl ammonium ethylsulfate | — | — | — | — | — | — | — |
| 1% NaCl solution | — | — | — | — | — | — | — |
| silk protein | — | — | — | — | — | — | — |

TABLE 36

| | Examplele | | | | | | |
|---|---|---|---|---|---|---|---|
| ingredient (kg) | 173 | 174 | 175 | 176 | 177 | 178 | 179 |
| composition blended in hair conditioner | Example 155 | Example 155 | Example 155 | Example 156 | Example 157 | Example 157 | Example 158 |
| | 10 | 20 | 16 | 14 | 20 | 35 | 25 |
| initial purified water | 70 | 70 | 70 | 70 | — | — | 75 |
| propylene glycol | — | — | — | — | 1 | — | — |
| 1,3-butylene glycol | 3 | 1 | 1 | — | — | — | — |
| glycerin | — | — | — | — | — | — | — |
| additive composition | — | — | — | 7[2)] | 5[3)] | — | — |
| parabens | 0.15 | 0.15 | 0.15 | 0.15 | 0.15 | 0.15 | — |
| PPT | — | — | — | — | — | — | — |
| pigment | proper amount | proper amount | — | — | — | — | — |
| perfume | proper amount | proper amount | proper amount | proper amount | proper amount | proper amount | — |
| methyl polysiloxane | — | — | — | — | — | — | — |
| malic acid | — | 0.5 | 0.5 | — | — | — | — |
| isopropyl myristate | — | — | — | — | 3.2 | — | — |
| cationized cellulose | 0.4 | — | — | — | — | — | — |
| lanolin amidopropyl ethyl dimethyl ammonium ethylsulfate | — | — | — | — | — | 3[4)] | — |
| 1% NaCl solution | — | — | — | — | — | — | 1 |
| silk protein | — | — | — | — | — | — | proper amount |

1)–4) in Table 35 and Table 36 are indicating, 1) ingredients (wt. %); dimethylsiloxane-methylstearoxysiloxane copolymer (50), diisopropyl adipate (25), ), diisobutyl adipate (25), 2) ingredients (wt. %); 50% cetyl trimethyl ammonium chloride (14), carboxyvinylpolymer (1.5), citric acid (2), methyl parahydroxybenzoate (0.1), propyl parahydroxybenzoate (0.1), ethanol (2), purified water (80.3), 3) ingredients (wt. %); polyoxyethylene nonylphenyl ether, (40), polyoxyethylene hydrogenated castor oil (25), polyoxyethylene glyceryl oleate (8), sorbitan trioleate, (8), polyethylene glycol distearate (8), methylphenyl polysiloxane (6.5), 35% cethyl trimethyl ammonium saccarinate solution (4.5), 4) containing 50 wt. % dipropylene glycol.

(Preparation of Oxidizing Hair Coloring Agents)

Examples 180–183
Preparation of No. 1 Agents

To initial purified water that was heated to the temperature of 83–86° C., NMP (N-methl-2-pyrrolidone), dye intermediates (resorcinol, p-phenylene diamine, m-aminophenol, p-aminophenol) and antioxidant were added, and mixed homogeneously. To this, the composition blended in hair coloring (Example 161–164) that was dissolved at the temperature of 83–86° C. was added with stirring and emulsified. After the emulsion was cooled down to the temperature of 45° C. with stirring, alkaline agents (MEA, strong ammonium solution etc.), sequestering agent (EDTA, 1-hydroxyethane-1,1-diphosphonic acid) were added, and finally, purified water (add water) was added so as to adjust the total weight to be 100 kg. Thus No. 1 agent was prepared. The ingredients and contents (kg) are shown in Table 37.

Preparation of No. 2 Agents

The composition blended in hair coloring (Example 161–164), that was heated to the temperature of 80–85° C.

and then dissolved homogeneously, was added with stirring to initial purified water that was heated to the temperature of 80–85° C., and emulsified. After the emulsion was cooled down to the temperature of 45° C. with constant stirring, 60% 1-hydroxyethane-1,1-diphosphonic acid, dibasic sodium phosphate (12 hydrate) were added. Further, 35 wt. % hydrogen peroxide solution was added. Finally, purified water (add water) was added so as to adjust the total weight to be 100 kg. Thus No. 2 agent was prepared. The ingredients and contents (kg) are shown in Table 37.

Preparation of No. 2 Agents

The composition blended in waving agent (Examples 159–161), that was dissolved homogeneously at the temperature 80–85° C., was added with stirring to initial purified water that was previously heated to the temperature 80–85° C., and then emulsified. After the emulsion was cooled down to the temperature of 45° C., sodium bromate was added, and then further, purified water (add water) was added so as to adjust the total weight to be 100 kg. Thus, the No. 2 agent of the present invention was prepared. Ingredients and contents (kg) are shown in Table 38.

TABLE 37

| | Examplele | | | |
|---|---|---|---|---|
| ingredient (kg) | 180 | 181 | 182 | 183 |
| No. 1 agent | | | | |
| composition blended in hair coloring | Example 161 20 | Example 162 20 | Example 163 20 | Example 164 25 |
| dye intermediate | proper amount | proper amount | proper amount | proper amount |
| antioxidant | proper amount | proper amount | proper amount | proper amount |
| MEA | proper amount | — | — | proper amount |
| strong ammonia solution | — | 4 | 4 | — |
| EDTA | 0.2 | — | — | 0.2 |
| 60% hydroxyethane diphosphoric acid | — | 0.17 | 0.17 | — |
| NMP | 4 | — | — | — |
| initial purified water | 50 | 50 | 50 | 50 |
| No. 2 agent | | | | |
| composition blended in hair coloring | Example 161 3 | Example 162 3 | Example 163 3 | Example 164 3 |
| 60% hydroxyethane diphosphoric acid | 0.17 | 0.17 | 0.17 | 0.17 |
| dibasic sodium phosphate (12 hydrate) | 0.26 | 0.26 | 0.26 | 0.26 |
| 35% hydrogen peroxide | 17 | 16.5 | 16.5 | 16.5 |
| initial purified water | 70 | 60 | 60 | 60 |

(Preparation of Cationic Waving Agents)

Examples 184–186

Preparation of No. 1 Agents

The composition blended in waving agent (Example 159–161), that was dissolved homogeneously at the temperature 80–85° C., was added with stirring to initial purified water that was previously heated to the temperature 80–85° C., and then emulsified. Then the emulsion was cooled down to the temperature of 45° C., 50% ammonium thioglycolate or 40% diammonium dithiodiglycolate, strong ammonia solution, dibasic sodium phosphate and ammonium bicarbonate were added. Finally, purified water (add water) was added so as to adjust the total weight to be 100 kg. Thus No. 1 agent was prepared. Ingredients and contents (kg) are shown in Table 38.

Example 187

Preparation of No. 1 Agents

No. 1 agents was prepared by the same process as Example 185 except that the composition blended in waving agent of Example 159 (10 wt. %) was used instead of Example 160 (12 wt. %). Ingredients and contents (kg) are shown in Table 38.

Preparation of No. 2 Agents

To lauryl trimethyl ammonium chloride and sodium bromate, purified water was added so as to adjust the total weight to be 100 kg. Thus, No. 2 agent was prepared. Ingredients and contents (kg) are shown in Table 38.

TABLE 38

| | Examplele | | | |
|---|---|---|---|---|
| ingredient (kg) | 184 | 185 | 186 | 187 |
| No. 1 agent | | | | |
| composition blended in waving agent | Example 159 12 | Example 160 12 | Example 161 15 | Example 159 1 |
| 50% ammonium thioglycolate | 14 | 13 | 13 | 13 |
| 40% diammonium dithiodiglycolate | 2 | — | — | — |
| strong ammonia solution | 2.4 | proper amount | proper amount | proper amount |
| dibasic sodium phosphate (12 hydrate) | 1.8 | — | — | — |
| ammonium bicarbonate | — | proper amount | proper amount | proper amount |
| initial purified water | 50 | 50 | 50 | 50 |

TABLE 38-continued

| | Examplele | | | |
|---|---|---|---|---|
| ingredient (kg) | 184 | 185 | 186 | 187 |
| No. 2 agent | | | | |
| composition blended in waving agent | Example 159 12 | Example 160 12 | Example 161 15 | — |
| sodium bromate | 8 | 8 | 8 | 8 |
| lauryl trimethyl ammonium chloride | — | — | — | 1 |
| initial purified water | 60 | 60 | 60 | — |

(Preparation of Finishing Agents)

Example 188

About 85 kg of initial purified water was heated to the temperature of 83–86° C. On the other hand, to 5 kg of the composition blended in finishing agent (Example 161), proper amount of parabens were added and heated to the temperature of 83–86° C., and then dissolved homogeneously. Then, the homogeneous dissolved material was added to the above-mentioned hot water with constant stirring, and then emulsified. After the emulsion was cooled down to the temperature of 45–50° C. with constant stirring, purified water (add water) was added so as to adjust the total weight to be 100 kg. Thus, the finishing agent of the present invention was prepared.

(Preparation of Color Fixing Agent)

Example 189

About 55 kg of initial purified water was heated to the temperature of 83–86° C. On the other hand, 15 kg of the composition blended in color fixing agent (Example 154) and 0.1 kg of parabens were mixed and heated to the temperature of 80–85° C., and then dissolved homogeneously. Next, the homogeneous dissolved material was added to the above-mentioned hot water with constant stirring, and then emulsified. After the emulsion was cooled down to the temperature of about 50° C. with constant stirring, aqueous composition (25 kg of purified water, 2 kg of cationized polymer of tannic acid [trade name, "HAIR-ROL TC1000", Sanyo-Kasei co.], 0.4 kg of 85% phosphoric acid, 1 kg of 70% glycolic acid) and perfumes were added, and finally purified water (add water) was added so as to adjust the total weight to be 100 kg. Thus, the color fixing agent of the present invention was prepared.

(Preparation of the Composition Blended in Hair Treating Agent)

Example 190

62 kg of Cetanol, 2 kg of polyoxyethylene oleyl ether, 11 kg of lipophilic glyceryl monostearate, 25 kg of stearyl trimethyl ammonium chloride (in which 40 wt. % IPA was contained) were mixed, and heated to the temperature of about 80–85° C., then stirred and dissolved homogeneously. Thus, the composition blended in a hair treating agent of the present invention was prepared.

(The Organoleptic Tests About Hair Treating Effects of the Hair Treating Agents)

Hair treatments were carried out to 50 monitors by the following methods. And the results of the organoleptic tests about hair treating effects (i. e. feel when used) of the hair treating agents were obtained. The results of organoleptic tests were summarized in Table 39.

The Method for Hair Treating with Hair Conditioners

After ordinary shampoo, a specimen of each hair conditioners (Examples 166–179) was applied to hair and spread by combing, and then rinsed and dried using a dryer.

The Method for Hair Treating with Hair Colorings

No. 1 agents and No. 2 agents of the hair colorings (Example 180–183) were mixed (the wt. % ratio of No. 1 agents to No. 2 agents was 1:1). This mixture was applied to hair and left for 30 minutes at room temperature. Then, the hair was rinsed and dried using a dryer.

The Method for Hair Treating with Waving Agents

In a Case of Straight Type Permanent Wave

No. 1 agents of the waving agents (examples 184–186) were coated to hair and spread by combing and the hair was formed to the straight shape. Then, the hair was left for 10 minutes. After that, No. 2 agents was coated to hair and spread by combing, and then left for 10 minutes, and finally, rinsed and dried using a dryer.

In a Case of Curling Type Permanent Wave

No. 1 agents of the waving agents (Example 182) was coated to hair and spread by combing, and the hair was wound to a rod and left for 7 minutes at room temperature. Then No. 2 agents was coated by an applicator and left for 7 minutes. Repeatedly, No. 2 agents was coated by an applicator and left for 7 minutes. Next, the rod was removed, and the hair was rinsed and dried using a dryer.

The Method for Hair Treating with Finishing Agents

The finishing agent (Example 188) was coated to hair and spread.

The Method for Hair Treating with Finishing Agents

The finishing agents (Example 150) was coated to hair and spread.

The Method for Hair Treating with Color Fixing Agents

Hair colorings on the market was coated to hair and spread by combing. Next, the hair was left for 15 minutes at 45° C., and then rinsed and dried using a dryer. Then, hair treating with the color fixing agents (Example 189) was carried out by the same way to the hair treating with an ordinary rinses. In the treating, the hair was rinsed and dried using a dryer after coated with the color fixing agents.

TABLE 39

| hair treating agent (Example) | supple | slippery feel | soft feel | moist feel | no tangles and no squeak | smooth feel | rustle feeling | keeping ability of hair styling | prevention of dye decolorization |
|---|---|---|---|---|---|---|---|---|---|
| 166 | ⊚ | ○ | ⊚ | ⊚ | ⊚ | ⊚ | ○ | — | — |
| 167 | ○ | ○ | Δ | ○ | ⊚ | ⊚ | ⊚ | — | — |
| 168 | ○ | ○ | Δ | ○ | ⊚ | ⊚ | ⊚ | — | — |
| 169 | ○ | ○ | Δ | ○ | ⊚ | ⊚ | ○ | — | — |
| 170 | ○ | ○ | ○ | ○ | ⊚ | ⊚ | ○ | — | — |
| 171 | ○ | ○ | Δ | ○ | ⊚ | ⊚ | ○ | — | — |
| 172 | ○ | ○ | ○ | ○ | ⊚ | ⊚ | ○ | — | — |
| 173 | ⊚ | ⊚ | ⊚ | ⊚ | ⊚ | ○ | ⊚ | — | — |
| 174 | ⊚ | ⊚ | ⊚ | ⊚ | ⊚ | ○ | ⊚ | — | — |
| 175 | ⊚ | ⊚ | ⊚ | ⊚ | ⊚ | ○ | ○ | — | — |
| 176 | ○ | ⊚ | ⊚ | ⊚ | ⊚ | ⊚ | ○ | — | — |
| 177 | Δ | ○ | ⊚ | Δ | ○ | ⊚ | ○ | — | — |
| 178 | Δ | ○ | ⊚ | Δ | ○ | ○ | ○ | — | — |
| 179 | ○ | ⊚ | Δ | ○ | ⊚ | ⊚ | ○ | — | — |
| 180 | ○ | Δ | ⊚ | ⊚ | ○ | ○ | ○ | — | — |
| 181 | Δ | Δ | ○ | ⊚ | Δ | Δ | ○ | — | — |
| 182 | Δ | Δ | ○ | ○ | Δ | Δ | ○ | — | — |
| 183 | ○ | ○ | ⊚ | ⊚ | ○ | ○ | ○ | — | — |
| 184 | ⊚ | Δ | ⊚ | ⊚ | ⊚ | ⊚ | ○ | — | — |
| 185 | ⊚ | Δ | ⊚ | ⊚ | ⊚ | ○ | ○ | — | — |
| 186 | ⊚ | Δ | ⊚ | ⊚ | ⊚ | ○ | ○ | — | — |
| 187 | ⊚ | Δ | ⊚ | ⊚ | ⊚ | ○ | ○ | — | — |
| 188 | ⊚ | ○ | ⊚ | ⊚ | ⊚ | ⊚ | ○ | ⊚ | — |
| 189 | Δ | ○ | Δ | ○ | ○ | ⊚ | ○ | — | ⊚ |

In Table 32, ⊚ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as supple, slippery, soft feel, moist feel, no tangle and no squeak, smooth feel (smooth combing), rustle feeling, keeping ability of hair styling, preventive ability for fading dye. Further, in the preparation process of hair treating agent since it is possible by using the compositions blended in a hair treating agents of the present invention to blend esters, alcohols, and cationic surfactants at a time, the production process may be remarkably simplified.

Example of the Seventh Embodiment (Preparation of the Compositions Blended in Hair Treating Agents)

Examples 191–208

The amount (kg) shown in Table 40 and Table 41 of ingredients were poured into a vessel, and mixed, and then the mixture was heated to 80–85° C., stirred and dissolved completely to prepare the compositions blended in a hair treating agents (Examples 191–208).

TABLE 40

| ingredient (kg) | Examplele | | | | | | | | |
|---|---|---|---|---|---|---|---|---|---|
| | 191 | 192 | 193 | 194 | 195 | 196 | 197 | 198 | 199 |
| glyceryl fatty acid ester | — | — | — | — | — | — | — | 1[11] | — |
| lipophilic glyceryl monostearate | 3 | — | — | 3 | — | 1 | — | — | 4 |
| butyl stearate | — | — | — | — | — | — | — | — | — |
| isopropyl palmitate | — | — | — | — | — | — | — | — | 10 |
| isopropyl myristate | 35 | 34 | 35 | 32 | 28 | 32 | 33 | 32 | 10 |
| lanolin fatty acid octyldodecyl ester | — | — | — | — | — | — | — | — | — |
| octyl hydroxystearate | — | — | — | — | — | — | — | — | — |
| oleyl alcohol | 12 | 17 | 12 | 17 | 10 | 9 | 9 | 10 | 10 |
| octyldodecanol | — | — | — | — | — | — | — | — | 5 |
| dipropylene glycol | — | — | — | — | — | — | — | — | — |
| stearyl alcohol | — | — | — | — | — | — | — | — | — |
| cetanol | 19 | 17 | 18 | 18 | 25 | 19 | 21 | 21 | 22 |
| lauryl alcohol | — | — | — | — | — | — | — | — | — |
| cetyl trimethyl ammonium chloride | 9[4] | — | — | 15[4] | — | — | — | — | — |
| stearyl trimethyl ammonium chloride[1] | — | — | — | — | — | — | — | — | — |
| behenyl trimethyl ammonium chloride[2] | 3 | — | — | 3 | — | — | — | — | 5 |

TABLE 40-continued

| ingredient (kg) | Examplele | | | | | | | | |
|---|---|---|---|---|---|---|---|---|---|
| | 191 | 192 | 193 | 194 | 195 | 196 | 197 | 198 | 199 |
| lanolin amidopropyl ethyl dimethyl ammonium ethylsulfate[3] | — | — | — | — | — | — | — | — | — |
| cetyl trimethyl ammonium bromide[4] | — | 17 | 12 | — | 17 | 17 | 16 | 14.99 | 15 |
| polyoxyethylene lanolin[5] | — | — | — | — | — | — | 1 | — | — |
| polyoxyethylene oleyl ether[6] | 1 | 2.6 | — | 1 | 2.1 | — | — | — | — |
| polyoxyethylene cetyl ether | 1[14] | 2.7[14] | 7.2[14] | 1[14] | 3.7[14] | 4.7[14] | 3.9[14] | 4.7[14] | 3.9[14] |
| polyoxyethylene lauryl ether | — | — | — | — | — | — | — | — | — |
| polyoxyethylene stearyl ether | — | — | — | — | — | — | — | — | — |
| olive oil | — | — | — | — | — | 1 | 1 | 1 | — |
| hydrogenated oil | — | — | — | — | — | — | — | 1[16] | — |
| mink oil | — | — | — | — | — | — | — | — | — |
| lanolin | 6 | 5 | 6 | 5 | 5 | 4 | 4 | 4 | 5 |
| hard lanolin | — | — | — | — | — | — | — | — | — |
| stearic acid | — | — | — | — | — | — | — | — | 1 |
| liquid petrolatum | — | — | — | — | — | — | — | — | — |
| vaseline | — | — | — | — | — | 2 | 2 | 2 | — |
| paraffine | — | — | — | — | — | — | — | — | — |
| stearyl dimethyl glycine[9] | 10.95 | 4.98 | 9.95 | 5 | 8 | 6.99 | 6 | 6 | 6 |
| lauryl dimethyl glycine[9] | — | — | — | — | — | — | — | — | — |
| disodium edetate | 0.05 | 0.02 | 0.05 | — | — | 0.01 | — | 0.01 | — |
| polyoxypropylene butyl ether | — | — | — | — | — | 3 | 3 | 2 | 3 |
| methyl polysiloxane | — | — | — | — | — | — | — | — | — |

TABLE 41

| ingredient (kg) | Examplele | | | | | | | | |
|---|---|---|---|---|---|---|---|---|---|
| | 200 | 201 | 202 | 203 | 204 | 205 | 206 | 207 | 208 |
| glyceryl fatty acid ester | — | — | 8[12] | — | — | — | — | — | — |
| lipophilic glyceryl monostearate | — | — | — | — | 10 | — | 8 | 7 | 7 |
| butyl stearate | — | — | 5 | — | 5 | — | — | — | — |
| isopropyl palmitate | — | — | — | — | — | — | — | — | — |
| isopropyl myristate | 25 | 25 | — | 6 | — | 11 | 7 | — | 11 |
| lanolin fatty acid octyldodecyl ester | — | — | — | — | — | — | — | 5 | — |
| octyl hydroxystearate | — | — | — | — | — | — | — | 5 | — |
| oleyl alcohol | 11 | 10 | — | — | — | 4 | 4 | — | 3 |
| octyldodecanol | — | — | — | — | — | 1 | 1 | — | 1 |
| dipropylene glycol | — | — | 5 | — | — | 7 | 7.8 | 7 | 7 |
| stearyl alcohol | — | — | 45 | — | 20 | 41 | — | — | — |
| cetanol | 22 | 20 | — | 30 | — | — | 19 | 23 | 19 |
| lauryl alcohol | — | — | — | — | — | 1 | — | — | — |
| cetyl trimethyl ammonium chloride | 11.5[4] | — | — | 25[4] | 30[13] | 11[4] | — | — | — |
| stearyl trimethyl ammonium chloride[1] | — | — | 25 | — | — | 1 | — | — | — |
| behenyl trimethyl ammonium chloride[2] | 4 | — | — | 5 | — | — | 2 | 17 | 15 |
| lanolin amidopropyl ethyl dimethyl ammonium ethylsulfate[3] | — | — | 5 | — | 5 | — | — | — | — |
| cetyl trimethyl ammonium bromide[4] | — | 20 | — | — | — | — | 13 | — | 2 |
| polyoxyethylene lanolin[5] | — | — | — | — | — | — | — | — | — |
| polyoxyethylene oleyl ether[6] | 0.8 | — | — | — | 10 | — | — | — | — |
| polyoxyethylene cetyl ether | 1.1[14] | 1.7[14] | — | 2.1[14] | 5 | 5.5[15] | 1.1[15] | 4.3[15] | 4.2[15] |
| polyoxyethylene lauryl ether | — | — | 2 | — | — | 1.8 | — | — | — |
| polyoxyethylene stearyl ether | — | — | — | — | — | — | 3.8 | — | — |
| olive oil | — | — | — | — | — | — | — | — | — |
| hydrogenated oil | — | — | — | — | — | 4[17] | 15[17] | 16[17] | 14[17] |
| mink oil | — | — | 5 | — | 5 | — | — | — | — |
| lanolin | 7 | 6 | — | 13 | — | — | — | — | — |
| hard lanolin | — | — | — | — | — | 7 | — | — | — |
| stearic acid | — | — | — | 3 | — | — | — | — | — |
| liquid petrolatum | 13 | 13 | — | 16 | — | — | 3 | — | 3 |
| vaseline | — | — | — | — | — | — | — | — | — |
| paraffine | — | — | — | — | — | 5 | 15 | 16 | 14 |
| stearyl dimethyl glycine[9] | 5 | 5 | — | — | — | — | — | — | — |
| lauryl dimethyl glycine[9] | — | — | — | — | 10 | — | — | — | — |
| disodium edetate | | | | | | | | | |

TABLE 41-continued

| | Examplele | | | | | | | | |
|---|---|---|---|---|---|---|---|---|---|
| ingredient (kg) | 200 | 201 | 202 | 203 | 204 | 205 | 206 | 207 | 208 |
| polyoxypropylene butyl ether | — | — | — | — | — | — | — | — | — |
| methyl polysiloxane | — | — | — | — | — | — | 0.2 | — | — |

1)–15)in Tables 40 and 41 were indicating,
1)containing 40 wt. % of IPA (isopropanol),
2)containing 20 wt. % IPA,
3)containing 50 wt. % of dipropylene glycol,
4)containing 30 wt. % of ethanol,
5)15EO,
6)6EO,
7)23EO,
8)13EO,
9)26 wt. % aqueous solution,
10)40PO,
11)glyceryl monomyristate,
12)mixture of mono and diglyceryl oleate and stearate,
13)containing 35 wt. % of IPA + 15 wt. % of purified water,
14)7EO,
15)40EO,
16)hydrogenated palm oil fatty acid triglyceride,
17)hydrogenated tallow fatty acid triglyceride.

(Preparation of Hair Conditioners)

Examples 209–214

Initial purified water was heated to the temperature of 83–86° C. On the other hand, the composition blended in hair conditioner obtained above (Examples 191, 193, 198, 200, 202 or 203) was heated to the temperature of 83–86° C. and dissolved homogeneously and added to the above-mentioned hot water with constant stirring and emulsified. Then the emulsion was cooled down to the temperature of 45–50° C. with constant stirring, additives shown in Table 42 were added. Finally, purified water (add water) was added so as to adjust the total weight to be 100 kg. Thus, the hair conditioners of the present invention (Examples 209–214) were prepared. The ingredients and contents (kg) were shown in Table 42.

C. was added, stirred and emulsified. Then the emulsion was cooled down to the temperature of 50–55° C. with constant stirring, 8 kg of hydrochloric acid- MEA solution, 0.2 kg of EDTA and a proper amount of MEA were added, further purified water (add water) was added so as to adjust the total weight to be 100 kg. Thus No. 1 agent was prepared.

Preparation of No. 2 Agent 70 kg of initial purified water was heated to the temperature of 80–85° C., then 10 kg of the composition blended in hair coloring (Example 205) that was dissolved homogeneously at the temperature of 80–85° C. was added, stirred and emulsified. After the emulsion was cooled down to the temperature of 45° C. with constant stirring, 0.17 kg of 60% hydroxyethane diphosphonic acid and 0.26 kg of dibasic sodium phosphate (12 hydrate) were added. Next, 16.9 kg of 35 wt. % hydrogen peroxide was added. Finally, purified water (add water) was added so as to adjust the total weight to be 100 kg. Thus No. 2 agent was prepared.

TABLE 42

| | Examplele | | | | | |
|---|---|---|---|---|---|---|
| ingredient (kg) | 209 | 210 | 211 | 212 | 213 | 214 |
| composition blended in hair conditioner | Example 191 25 | Example 193 25 | Example 198 25 | Example 200 25 | Example 202 8 | Example 203 10 |
| initial purified water | about 70 | about 70 | about 70 | about 70 | about 80 | about 80 |
| oiliness material | proper amount | proper amount | proper amount | proper amount | — | — |
| PPT | proper amount | — | — | proper amount | — | proper amount |
| parabens | proper amount | proper amount | proper amount | proper amount | proper amount | proper amount |
| perfume | proper amount | proper amount | proper amount | proper amount | proper amount | proper amount |

(Preparation of Oxidizing Hair Coloring Agents)

Example 215
Preparation of No. 1 Agent 50 kg of initial purified water was heated to the temperature of 80–85° C., then 0.5 kg of anhydrous sodium sulfite, 3.0 kg of propylene glycol and a proper amount of dye intermediates (resorcinol and p-phenylene diamine, m-aminophenol, p-aminophenol) were added and mixed homogeneously. To the obtained mixture, 25 kg of the composition blended in hair coloring (Example 205) that was dissolved homogeneously at the temperature of 80–85°

(Preparation of Decolorizing Agent)

Example 216
Preparation of No. 1 Agent 70 kg of initial purified water was heated to the temperature of 80–85° C., then 15 kg of the composition blended in hair coloring (Example 205) that was dissolved homogeneously at the temperature of 80–85° C. was added to the hot water, stirred and emulsified. After cooled, 6.6 kg of MEA and 0.1 kg of disodium edetate were added, further purified water (add water) was added so as to adjust the total weight to be 100 kg. Thus No. 1 agent was prepared.

Preparation of No. 2 Agents

To 70 kg of initial purified water that was heated to the temperature of 80–85° C., 10 kg of the composition blended in hair coloring (Example 205) that was dissolved homogeneously at the temperature of 80–85° C. was added, stirred and emulsified. Then the emulsion was cooled down to the temperature of 45° C. with constant stirring, 0.17 kg of 60% hydroxyethane diphosphonic acid and 0.26 kg of dibasic sodium phosphate (12 hydrate) were added. Further, 16.9 kg of 35 wt. % hydrogen peroxide was added. Finally, purified water (add water) was added so as to adjust the total weight to be 100 kg. Thus No. 2 agent was prepared.
(Preparation of Acidic Hair Coloring Material)

Example 217

20 kg of the composition blended in hair coloring (Example 206) was homogeneously dissolved at 80–85° C. and added to 1 kg of Red No. 227 that was previously dissolved in a proper amount of initial purified water heated to 80–85° C., and emulsified. After the emulsion was cooled down to the temperature of 45° C. with constant stirring, 3 kg of benzyl alcohol, 5 kg of N-methl-2-pyrrolidone and 1 kg of glycolic acid were added, further, purified water (add water) was added so as to adjust the total weight to be 100 kg. Thus the acidic hair coloring material was prepared.
(Preparation of Cationic Waving Agent)

Example 218

Preparation of No. 1 Agents

The composition blended in waving agent (Example 205) was homogeneously dissolved at 80–85° C. and added to initial purified water that was previously heated to 80–85° C., stirred and emulsified. After the emulsion was cooled down to the temperature of 45° C. with constant stirring, 50% ammonium thioglycolate, strong ammonia solution and ammonium bicarbonate were added to the emulsion, further, purified water (add water) was added so as to adjust the total weight to be 100 kg. Thus No. 1 agent was prepared. ingredients and contents (kg) were shown in Table 43.
Preparation of No. 2 Agent The composition blended in waving agent (Example 205 or 206) was homogeneously dissolved at 80–85° C. and added to initial purified water that was previously heated to 80–85° C., stirred and emulsified. After the emulsion was cooled down to the temperature of 45° C. with constant stirring, sodium bromate was added to the emulsion. Further, purified water (add water) was added so as to adjust the total weight to be 100 kg. Thus No. 2 agent was prepared. ingredients and contents (kg) were shown in Table 43.

Example 219

Preparation of No. 1 Agent

No. 1 agents was prepared according to the formulations as shown in Table 43 by the same process as Example 218 except that the composition blended in waving agent of Example 206 was used instead of Example 205.
Preparation of No. 2 Agent The composition blended in waving agent (Example 206) was homogeneously dissolved at 80–85° C. and added to initial purified water that was previously heated to 80–85° C., stirred and emulsified. After the emulsion was cooled down to the temperature of 45° C. with constant stirring, other ingredients shown in Table 43 were added to the emulsion, further, purified water (add water) was added so as to adjust the total weight to be 100 kg. Thus No. 1 agent was prepared. Ingredients and contents (kg) were shown in Table 43.

Example 220

Preparation of No. 1 Agents

No. 1 agents was prepared by the same process as process as Example 219.
Preparation of No. 2 Agent To lauryl trimethyl ammonium chloride and sodium bromate, purified water was added so as to adjust the total weight to be 100 kg. And No. 2 agent was prepared. Ingredients and contents (kg) were shown in Table 43.
(Preparation of Curling Cream Type Waving Agent)

Example 221

Preparation of No. 1 Agent

The composition blended in waving agents (Example 206) was homogeneously dissolved at 80–85° C. and added to initial purified water that was previously heated to 80–85° C., stirred and emulsified. After the emulsion was cooled down to the temperature of 45° C. with constant stirring, aqueous solution of anhydrous sodium sulfite and MEA were added to the emulsion, further, purified water (add water) was added so as to adjust the total weight to be 100 kg. Thus No. 1 agent of curling cream type waving agent was prepared. Ingredients and contents (kg) were shown in Table 43.
Preparation of No. 2 Agent Purified water was added to 1 kg of citric acid so as to adjust the total weight to be 100 kg. Thus, No. 2 agent was prepared.

Example 222

Preparation of No. 1 Agent

By the same process as Example 221 except using Example 205 instead of Example 206, No. 1 agent of curling cream type waving agent was prepared. Ingredients and contents (kg) were shown in Table 43.
Preparation of No. 2 Agents No. 2 agent was prepared by the same process as Example 221.

TABLE 43

| | Examplele | | | | |
|---|---|---|---|---|---|
| ingredient (kg) | 218 | 219 | 220 | 221 | 222 |
| No. 1 agent | | | | | |
| composition blended in waving agent | Example 205 16 | Example 206 15 | Example 206 15 | Example 206 10 | Example 205 10 |
| 50% ammonium thioglycolate | 13.5 | 13 | 13 | — | — |
| strong ammonia solution | proper amount | proper amount | proper amount | — | — |
| ammonium bicarbonate | proper amount | proper amount | proper amount | — | — |
| anhydrous sodium sulfite | — | — | — | 4 | 4 |

TABLE 43-continued

| ingredient (kg) | Examplele | | | | |
|---|---|---|---|---|---|
| | 218 | 219 | 220 | 221 | 222 |
| monoethanolamine | — | — | — | 2.5 | 2.5 |
| initial purified water | 50 | 50 | 50 | 50 | 50 |
| No. 2 agent | | | | | |
| composition blended in waving agent | Example 205 16 | Example 206 15 | — | — | — |
| lauryl trimethyl ammonium chloride | — | — | 1 | — | — |
| citric acid | — | — | — | 1 | 1 |
| sodium bromate | 8 | — | 8 | — | — |
| 35% hydrogen peroxide aqueous solution | — | 6 | — | — | — |
| 60% hydroxyethane diphosphoric acid | — | 0.17 | — | — | — |
| dibasic sodium phosphate (12 hydrate) | — | 0.26 | — | — | — |
| initial purified water | about 55 | about 55 | — | — | — |

(Preparation of the Finishing Agent)

Example 223

85 kg of initial purified water was heated to the temperature of 83–86° C. On the other hand, 5 kg of the composition blended in finishing agent (Example 206) was heated to the temperature of 83–86° C., and dissolved homogeneously. This was added to the above-mentioned hot water with constant stirring and emulsified. After the emulsion was cooled down to the temperature of 45–50° C. with constant stirring, a proper amount of parabens were added. Finally, purified water(add water) was added so as to adjust the total weight to be 100 kg. Thus, the composition blended in finishing agent was prepared.

(The Organoleptic Tests About Hair Treating Effects of the Hair Treating Agents)

Hair treatments were carried out to 50 monitors by the following methods. And the results of the organoleptic tests about hair treating effects (i. e. feel when used) of the hair treating agents were obtained. The results of organoleptic tests were summarized in Table 44.

The Method for Hair Treating with Hair Conditioners

After ordinary shampoo, a specimen of each hair conditioners (examples 209–214) was applied to hair and spread by combing. Then, the hair was rinsed and dried using a dryer.

The Method for Hair Treating with Hair Colorings

The No. 1 and No. 2 agents of Example 215 were mixed by the ratio of 1:1 (weight ratio) and coated to hair. Left for 30 minutes at the room temperature, then the hair was rinsed and dried using a dryer.

The Method for Hair Treating with Waving Agents

In a Case of Straight Type Permanent Wave

No. 1 agents of the waving agents Examples 218 and 219) were coated to hair and spread by combing and the hair was formed to the straight shape. Then, the hair was left for 10 minutes. After that, No. 2 agents was coated to hair and spread by combing. Finally, the hair was rinsed and dried using a dryer.

In a Case of Curling Type Permanent Wave

No. 1 agents of the waving agents Example 221) were coated to hair and spread by combing, and the hair was wound to a rod and heated for 7 minutes at 45° C. Then No. 2 agents was coated by an applicator and left for 7 minutes. After the rod was removed, the hair was rinsed and dried using a dryer.

The Method for Hair Treating with Finishing Agents

The finishing agents (Example 223) were coated to hair and spread.

TABLE 44

| hair treating agent (Example) | feel when used | | | | | | |
|---|---|---|---|---|---|---|---|
| | supple | slightly oily feel | soft feel | moist feel | no tangles and no squeak | smooth feel | keeping ability of hair styling |
| 209 | ⊙ | ⊙ | ○ | ○ | ⊙ | ○ | ○ |
| 210 | ⊙ | ⊙ | ⊙ | ○ | ⊙ | ○ | ○ |
| 211 | ⊙ | ⊙ | ○ | ⊙ | ⊙ | ○ | ○ |
| 212 | ○ | ○ | ○ | ⊙ | ⊙ | ○ | ○ |
| 213 | ○ | ○ | ⊙ | ⊙ | ⊙ | ○ | ○ |
| 214 | ⊙ | ⊙ | ○ | ○ | ⊙ | ○ | ○ |
| 215 | ○ | ⊙ | ⊙ | ○ | Δ | ○ | ○ |
| 218 | ○ | ⊙ | ○ | ○ | Δ | ○ | ○ |
| 219 | ○ | ⊙ | ○ | ○ | Δ | ○ | ○ |
| 221 | ○ | ○ | ○ | ○ | Δ | ○ | ○ |
| 223 | ○ | ⊙ | ○ | ○ | ○ | ○ | ⊙ |

In Table 44, ⊙ indicates "very good", ○ indicates "good" and Δ indicates "normal".

As clearly understood from the results of the above-mentioned examples, the compositions blended in hair treating agents of the present embodiment is prepared by selecting and combining adequately the ingredients which are cheap and easy to purchase so as to display an excellent hair treating effect. Therefore, the compositions blended in hair treating agents of the present invention may be produced by lower cost and easily.

Since the hair treating agents of the present embodiment is prepared using above-mentioned compositions blended in hair treating agents of the present invention, the cost for production is low, further, has an excellent hair treating effects such as such as supple, slightly oily feel (luster), soft feel, moist feel, no tangle and no squeak, smooth feel (smooth combing), keeping ability of hair styling. Further, in the preparation process of hair treating agent since it is possible to blend fatty esters, alcohols, cationic surfactants, nonionic surfactants, and fats and oils at a time, the production process may be remarkably simplified.

What is claimed is:

1. A composition blended in a hair treating agent, comprising:

propylene glycol dicaprate,
caprylic capric acid triglyceride and
polyoxypropylene butyl ether.

2. A composition blended in a hair treating agent, comprising:

diisopropyl adipate,
diisobutyl adipate and
dimethylsiloxane·methylstearoxysiloxane copolymer.

3. A composition blended in a hair treating agent, comprising:

isopropyl linoleate,
polyoxyethylene oleyl ether,
sorbitan monooleate,
safflower oil,
sorbic acid,
oleic acid,
phosphoric acid,
sodium hydroxide,
liquid petrolatum and
water.

4. A composition blended in a hair treating agent, comprising:

isopropyl linoleate,
polyoxyethylene oleyl ether,
sorbitan monooleate,
avocado oil,
safflower oil,
sorbic acid,
oleic acid,
phosphoric acid,
sodium hydroxide,
liquid petrolatum and
water.

5. A composition blended in a hair treating agent, comprising:

dipentaerythritol fatty acid ester,
polyoxyethylene oleyl ether,
sorbitan sesquioleate,
sorbitan trioleate,
meadowfoam oil,
sorbic acid,
oleic acid,
phosphoric acid,
sodium hydroxide,
liquid petrolatum and
water.

6. A composition blended in a hair treating agent, comprising:

lipophilic glyceryl monostearate,
isopropyl palmitate,
diisobutyl adipate,
myristyl alcohol,
oleyl alcohol,
dipropylene glycol,
polyoxyethylene hydrogenated castor oil,
dimethyl stearylamine,
hydrogenated oil,
olive oil,
α-olefin oligomer and
lactic acid.

7. A composition blended in a hair treating agent, comprising:

glycelin fatty acid ester,
myristyl alcohol,
behenyl alcohol,
ethanol,
polyoxyethylene hydrogenated castor oil,
castor oil,
shear butter,
hydrochloric acid salt of N-[3-alkyl(12,14)oxy-2-hydroxypropyl]-L-arginine,
polyglyceryl diisostearate and
stearamidopropyl dimethylamine.

8. A composition blended in a hair treating agent, comprising:

pentaerythritol tetra-2-ethylhexanoate,
1,3-butylene glycol,
polyoxyethylene cetyl ether,
squalane,
microcrystalline wax and
candelilla wax.

9. A composition blended in a hair treating agent, comprising:

di(2-ethylhexyl)succinate,
1,3-butylene glycol,
polyoxyethylene cetyl ether,
squalane,
microcrystalline wax and
candelilla wax.

10. A composition blended in a hair treating agent, comprising:

isopropyl palmitate,
cetanol,
polyoxyethylene cetyl ether,
sodium cetyl sulfate,
beeswax and
purified water.

11. A composition blended in a hair treating agent, comprising:

lipophilic glyceryl monooleate,
isopropyl myristate,
hexyldecanol,
cetanol,
polyoxyethylene lauryl ether, polyoxyethylene cetyl ether,
coconut fatty acid diethanolamide and
triethanolamine N-cocoyl-L-glutamate.

12. A composition blended in a hair treating agent, comprising:
    lipophilic glyceryl monooleate,
    isopropyl myristate,
    hexyldecanol,
    cetanol,
    polyoxyethylene lauryl ether,
    polyoxyethylene cetyl ether,
    coconut fatty acid diethanolamide and
    triethanolamine N-cocoyl-L-glutamate and
    methyl polysiloxane.

13. A composition blended in a hair treating agent, comprising:
    myristyl myristate,
    cetanol,
    polyoxyethylene cetyl ether, and
    hydrogenated oil.

14. A composition blended in a hair treating agent, comprising:
    lipophilic glyceryl monostearate,
    isopropyl myristate,
    hexyldecanol,
    cetanol,
    polyoxyethylene cetyl ether,
    sodium palmitoyl N-methyl taurate,
    sodium tetradecen sulfonate,
    candelilla wax,
    beeswax and
    purified water.

15. A composition blended in a hair treating agent, comprising:
    diisobutyl adipate,
    myristyl alcohol,
    hexyldecanol,
    behenyl alcohol,
    dimethyl stearylamine,
    myristic acid and
    shea butter.

16. A composition blended in a hair treating agent, comprising:
    glyceryl monooleate,
    isopropyl myristate,
    hexyldecanol,
    cetanol,
    polyoxyethylene cetyl ether,
    lauric acid,
    sodium tetradecen sulfonate,
    sodium palmitoyl N-methyl taulate,
    sulfated castor oil,
    polypropylene glycol oligosuccinate and
    purified water.

17. A composition blended in a hair treating agent, comprising:
    lipophilic glyceryl monostearate,
    stearyl stearate,
    behenyl alcohol,
    arachyl alcohol,
    polyoxyethylene hydrogenated castor oil,
    sorbitan monostearate,
    stearic acid and
    liquid petrolatum.

18. A composition blended in a hair treating agent, comprising:
    mono and diglyceryl oleate and stearate,
    isopropyl myristate,
    cetanol,
    1,3-butylene glycol,
    polyoxyethylene cetyl ether,
    polyoxyethylene stearoxyl amide,
    lanolin fatty acid,
    sodium palmitoyl N-methyl taulate,
    triethanolamine N-cocoyl-L-glutamate,
    paraffin and
    purified water.

19. A composition blended in a hair treating agent, comprising:
    lipophilic glyceryl monostearate,
    cetanol,
    oleyl alcohol,
    behenyl trimethyl ammonium chloride and
    olive oil.

20. A composition blended in a hair treating agent, comprising:
    lipophilic glyceryl monostearate,
    cetanol,
    stearyl alcohol,
    behenyl alcohol,
    stearyl trimethyl ammonium chloride,
    cetyl trimethyl ammonium chloride,
    coconut fatty acid monoethanolamide,
    ceresin and
    carnauba wax.

21. A composition blended in a hair treating agent, comprising:
    diisopropyl adipate,
    lauryl alcohol,
    cetanol,
    cetyl trimethyl ammonium chloride,
    dipolyoxyethylene oleyl methyl ammonium chloride and
    polyoxyethylene lauryl ether.

22. A composition blended in a hair treating agent, comprising:
    lipophilic glyceryl monostearate,
    isopropyl myristate,
    cetanol,
    cetyl trimethyl ammonium chloride,
    behenyl trimethyl ammonium chloride and
    polyoxyethylene cetyl ether.

23. A composition blended in a hair treating agent, comprising:
    isopropyl myristate,
    butyl stearate,
    cetanol, cetyl trimethyl ammonium chloride,
polyoxyethylene lauryl ether and
paraffin.

24. A composition blended in a hair treating agent, comprising:
isopropyl palmitate,
cetanol,
glycerin,
stearyl trimethyl ammonium chloride,
polyoxyethylene cetyl ether and
paraffin.

25. A composition blended in a hair treating agent, comprising:
glyceryl cocoate,
octyl palmitate,
cetanol,
propylene glycol,
stearyl trimethyl ammonium chloride,
polyoxyethylene cetyl ether,
paraffin and
light liquid isoparaffin.

26. A composition blended in a hair treating agent, comprising:
mono and diglyceryl oleate and stearate,
isopropyl myristate,
cetostearyl alcohol,
cetyl trimethyl ammonium chloride,
dipolyoxyethylene oleyl methyl ammonium chloride,
polyoxyethylene oleyl ether and
coconut fatty acid monoethanolamide.

27. A composition blended in a hair treating agent, comprising:
isopropyl myristate,
oleyl alcohol,
cetanol,
cetyl trimethyl ammonium chloride,
behenyl trimethyl ammonium chloride,
polyoxyethylene oleyl ether,
polyoxyethylene cetyl ether,
lanolin,
liquid petrolatum and
stearyl dimethyl glycine.

28. A composition blended in a hair treating agent, comprising:
isopropyl myristate,
oleyl alcohol,
cetanol,
cetyl trimethyl ammonium bromide,
polyoxyethylene cetyl ether,
lanolin,
liquid petrolatum and
stearyl dimethyl glycine.

29. A composition blended in a hair treating agent, comprising:
isopropyl myristate,
oleyl alcohol,
octyldodecanol,
dipropylene glycol,
stearyl alcohol,
lauryl alcohol,
cetyl trimethyl ammonium chloride,
stearyl trimethyl ammonium chloride,
polyoxyethylene cetyl ether,
polyoxyethylene lauryl ether,
hydrogenated oil,
hard lanolin and
paraffin.

30. A composition blended in a hair treating agent, comprising:
lipophilic glyceryl monostearate,
isopropyl myristate,
oleyl alcohol,
octyldodecanol,
dipropylene glycol,
cetanol,
behenyl trimethyl ammonium chloride,
cetyl trimethyl ammonium bromide,
polyoxyethylene cetyl ether,
polyoxyethylene stearyl ether,
hydrogenated oil,
liquid petrolatum,
paraffin and
methyl polysiloxane.

* * * * *